(12) United States Patent
Johnson et al.

(10) Patent No.: US 8,637,491 B2
(45) Date of Patent: Jan. 28, 2014

(54) THIENO-PYRIDINE DERIVATIVES AS MEK INHIBITORS

(75) Inventors: James Andrew Johnson, Slough (GB); Daniel Christopher Brookings, Slough (GB); Barry John Langham, Slough (GB); Judi Charlotte Neuss, Slough (GB); Joanna Rachel Thorne, Slough (GB)

(73) Assignee: UCB Pharma S.A., Brussels (BE)

( * ) Notice: Subject to any disclaimer, the term of this patent is extended or adjusted under 35 U.S.C. 154(b) by 420 days.

(21) Appl. No.: 12/971,590

(22) Filed: Dec. 17, 2010

(65) Prior Publication Data

US 2011/0172191 A1 Jul. 14, 2011

Related U.S. Application Data

(63) Continuation of application No. PCT/GB2009/001504, filed on Jun. 12, 2009.

(30) Foreign Application Priority Data

Jun. 19, 2008 (GB) .................................. 0811304.5

(51) Int. Cl.
*A61K 31/675* (2006.01)
*C07D 491/02* (2006.01)

(52) U.S. Cl.
USPC ........................................... 514/81; 546/113

(58) Field of Classification Search
None
See application file for complete search history.

(56) References Cited

U.S. PATENT DOCUMENTS

| | | |
|---|---|---|
| 2003/0220365 A1 | 11/2003 | Stewart |
| 2004/0138251 A1 | 7/2004 | Boschelli |
| 2005/0049276 A1 | 3/2005 | Kaufman |
| 2005/0227959 A1 | 10/2005 | Yoshida |
| 2007/0049603 A1 | 3/2007 | Miknis |
| 2009/0149437 A1 | 6/2009 | Hutchings |
| 2009/0264411 A1 | 10/2009 | Laing |
| 2010/0179124 A1 | 7/2010 | Johnson |
| 2011/0021558 A1 | 1/2011 | Brookings |

FOREIGN PATENT DOCUMENTS

| | | |
|---|---|---|
| WO | 02/06213 | 1/2002 |
| WO | 03/077855 | 9/2003 |
| WO | 03/077914 | 9/2003 |
| WO | 04/000846 | 12/2003 |
| WO | 2004/113347 | 12/2004 |
| WO | 2004/113348 | 12/2004 |
| WO | 2005/009975 | 2/2005 |
| WO | 2005/023251 | 3/2005 |
| WO | 2005/023759 | 3/2005 |
| WO | 2005/023818 | 3/2005 |
| WO | 2005/051300 | 6/2005 |
| WO | 2005/051906 | 6/2005 |
| WO | 2007/044515 | 4/2007 |
| WO | 2007/088345 | 8/2007 |
| WO | 2007/120101 | 10/2007 |
| WO | 2008/020206 | 2/2008 |

OTHER PUBLICATIONS

Morissette et al., High-throughput crystallization: polymorphs, salts, co-crystals and solvates of pharmaceutical solids, Advanced Drug Delivery Reviews 2004, 56, 275-300.*
Hamdi et al., Solvates of indomethacin. Journal of Thermal Analysis and Calorimetry 2004, 76, 985-1001.*
Bremner, D.H. et al,: "The Synthesis of Thienopyridines from ortho-Halogenated Pyridine Derivatives; Part 2" Synthesis, 1997, pp. 949-952.
Bremner, D.H. et al.: "The Synthesis of Thienopyridines from ortho-Halogenated Pyridine Derivatives; Part 3" Sythesis, 1998, pp. 1095-1097.
Byrn et al., Solid-State Chemistry of Drugs, $2^{nd}$ Ed., SSCI, Inc., West Lafayette, IN, Ch. 11, 1991, pp. 233-247.
Erian, Ayman Wahba et al: "An Easy Direct Conversion of Pyridine- and Pyrimidine-Thiones into Multi-Fused Heterocyclic Compounds" Bulletin of the Chemical Society of Japan, 71(10), 1998, pp. 2387-2391.
Klemm L. H. et al., "Chemistry of Thienopyridines. XVII. Direct Halogenation of Thieno [2,3-b] pyridine (1)," *Journal of Heterocyclic Chemistry*, 1974, pp. 205-209.
West, Anthon R., Solid State Chemistry and its Applications, Wiley, New York, 1988, pp. 358 & 365.
Wermuth, Camille G. "Molecular Variation Based on Isosteric Replacements" in Chapter 13, The Practice of Medicinal Chemistry, Academic, 1996, pp. 203-237.
Hamdouchi et. al. "Structure-based design of a new class of highly selective aminoimidazo [1, 2-a] pyridine-based inhibitors of cyclin dependent kinases" Bioorganic & Medical Chemistry Letters 15, 2005 pp. 1943-1947.
Written Opinion of the International Searching Authority published Jul. 31, 2008 for PCT/GB2007/000310 filed Jan. 30, 2007.
Written Opinion of the International Searching Authority published Feb. 15, 2009 for PCT/GB2007/003114 filed Aug. 15, 2007.
Written Opinion of the International Searching Authority published Jan. 23, 2010 for PCT/GB2008/002430 filed Jul. 16, 2008.
Written Opinion of the International Searching Authority published Jul. 21, 2010 for PCT/GB2009/000144 filed Jan. 20, 2009.
Written Opinion of the International Searching Authority published Dec. 19, 2010 for PCT/GB2009/001504 filed Jun. 12, 2009.
International Search Report mailed Jun. 14, 2007 for PCT/GB2007/000310 filed Jan. 30, 2007.

(Continued)

*Primary Examiner* — Jason M Nolan
*Assistant Examiner* — Ana Z Muresan
(74) *Attorney, Agent, or Firm* — Feldman Gale, P.A.

(57) ABSTRACT

A series of thieno[2,3-b]pyridine derivatives, attached at the 2-position to a substituted anilino moiety, which are substituted in the 3-position by a carbonyl group linked to a pyrrolidin-1-yl ring which in turn forms part of a heteroatom-containing fused bicyclic ring system, being selective inhibitors of human MEK (MAPKK) enzymes, are accordingly of benefit in medicine, for example in the treatment of inflammatory, autoimmune, cardiovascular, proliferative (including oncological) and nociceptive conditions.

21 Claims, No Drawings

(56) References Cited

OTHER PUBLICATIONS

International Search Report mailed Feb. 29, 2008 for PCT/GB2007/003114 filed Aug. 15, 2007.
International Search Report mailed Aug. 28, 2008 for PCT/GB2008/002430 filed Jul. 16, 2008.
International Search Report mailed May 27, 2009 for PCT/GB2009/000144 filed Jan. 20, 2009.
International Search Report mailed Aug. 8, 2009 for PCT/GB2009/001504 filed Jun. 12, 2009.
International Preliminary Report on Patentability issued Aug. 5, 2008 for PCT/GB2007/000310 filed Jan. 30, 2007.
International Preliminary Report on Patentability issued Feb. 17, 2009 for PCT/GB2007/003114 filed Aug. 15, 2007.
International Preliminary Report on Patentability issued Jan. 26, 2010 PCT/GB2008/002430 filed Jul. 16, 2008.
International Preliminary Report on Patentability issued Jul. 27, 2010 for PCT/GB2009/000144 filed Jan. 20, 2009.
International Preliminary Report on Patentability issued Dec. 21, 2010 for PCT/GB2009/001504 filed Jun. 12, 2009.

* cited by examiner

THIENO-PYRIDINE DERIVATIVES AS MEK INHIBITORS

CROSS-REFERENCE TO RELATED APPLICATIONS

The present application is a continuation of International Application No.: PCT/GB2009/001504, filed Jun. 12, 2009, which claims priority under 119(a-d) to Great Britain Application No. GB 0811304.5, filed Jun. 19, 2008, each of which is hereby incorporated herein by reference in their entireties.

The present invention relates to a class of thieno-pyridine derivatives and to their use in therapy. More particularly, the invention is concerned with thieno[2,3-b]pyridine derivatives which are substituted in the 2-position by a substituted anilino moiety. These compounds are selective inhibitors of MEK (MAPKK) enzymes, and are accordingly of benefit as pharmaceutical agents, especially in the treatment of adverse inflammatory, autoimmune, cardiovascular, proliferative (including oncological) and nociceptive conditions.

MEK enzymes are implicated in a variety of physiological and pathological functions that are believed to be operative in a range of human diseases. These functions are summarised in paragraphs [0004] and [0005] of US 2005/0049276 A1.

The compounds of use in the present invention, being potent and selective MEK inhibitors, are therefore beneficial in the treatment and/or prevention of various human ailments. These include autoimmune and inflammatory disorders such as rheumatoid arthritis, osteoarthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); proliferative disorders such as restenosis, and oncological conditions including leukaemia, glioblastoma, lymphoma, melanoma, and human cancers of the liver, bone, skin, brain, pancreas, lung, breast, stomach, colon, rectum, prostate, ovary and cervix; and pain and nociceptive disorders, including chronic pain and neuropathic pain.

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human MEK enzymes.

MEK inhibitors based on a fused bicyclic aromatic ring system attached to a substituted anilino moiety are known from the art, such as from WO 2007/088345.

Nowhere in the prior art, however, is there the precise disclosure of a class of thieno[2,3-b]pyridine derivatives, attached at the 2-position to a substituted anilino moiety, which are substituted in the 3-position by a carbonyl group linked to a pyrrolidin-1-yl ring which in turn forms part of a heteroatom-containing fused bicyclic ring system. It has now been found that such compounds are particularly valuable as selective inhibitors of MEK enzymes.

The compounds of the present invention are potent and selective MEK inhibitors having a binding affinity ($IC_{50}$) for the human MEK1 and/or MEK2 enzyme of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human MEK1 and/or MEK2 enzyme relative to other human kinases.

The compounds of the present invention possess high potency, and interesting pharmacokinetic properties owing to their improved solubility and clearance.

The present invention provides a compound of formula (I), or a pharmaceutically acceptable salt, solvate or N-oxide thereof:

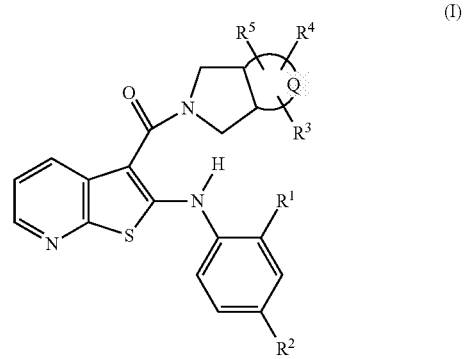

(I)

wherein

Q represents the residue of a three-, four-, five- or six-membered heterocyclic ring optionally containing one or two double bonds, wherein the heterocyclic ring comprises one, two or three heteroatoms independently selected from oxygen, sulphur, nitrogen and phosphorus;

$R^1$ represents hydrogen, halogen, cyano, nitro, $C_{1-6}$ alkyl, trifluoromethyl, $C_{1-6}$ alkoxy, trifluoromethoxy, $C_{1-6}$ alkylthio, $C_{1-6}$ alkylsulphinyl or $C_{1-6}$ alkylsulphonyl;

$R^2$ represents halogen, nitro, cyano, $C_{1-6}$ alkyl, $C_{2-6}$ alkynyl, hydroxy($C_{1-6}$)alkyl or formyl;

$R^3$ and $R^4$, where present, independently represent hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, nitro($C_{1-6}$)alkyl, halogen, cyano, trifluoromethyl, aryl, aryl($C_{1-6}$)alkyl, $C_{3-7}$ heterocycloalkyl($C_{1-6}$)alkyl, heteroaryl, heteroaryl($C_{1-6}$)alkyl, oxo, thioxo, imino, $C_{2-6}$ alkylcarbonyl, carboxy, $C_{2-6}$ alkoxycarbonyl, amino, $C_{1-6}$ alkylamino, di($C_{1-6}$)alkylamino, bis[hydroxy($C_{1-6}$)alkyl]-amino, $C_{1-6}$ alkylamino($C_{1-6}$)alkylamino, $C_{3-7}$ cycloalkylamino, arylamino, heteroarylamino, $C_{2-6}$ alkylcarbonylamino, $C_{2-6}$ alkoxycarbonylamino, ($C_{2-6}$)alkoxycarbonyl($C_{1-6}$)alkylamino, [($C_{2-6}$) alkoxycarbonyl][($C_{1-6}$)alkyl]amino, bis[($C_{2-6}$) alkoxycarbonyl($C_{1-6}$)alkyl]amino, $C_{2-6}$ alkoxycarbonylamino($C_{1-6}$)alkyl or aminocarbonyl; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents independently selected from $C_{1-6}$ alkyl, hydroxy and amino; and $R^5$, where present, represents hydrogen or $C_{1-6}$ alkyl.

The present invention also provides a compound of formula (I) as depicted above, or a pharmaceutically acceptable salt, solvate or N-oxide thereof, wherein Q represents the residue of a three-, four-, five- or six-membered heterocyclic ring optionally containing a double bond, wherein the heterocyclic ring comprises one, two or three heteroatoms independently selected from oxygen, sulphur, nitrogen and phosphorus;

$R^3$ and $R^4$, where present, independently represent hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, nitro($C_{1-6}$) alkyl, halogen, cyano, trifluoromethyl, aryl, aryl($C_{1-6}$)alkyl, heteroaryl, heteroaryl($C_{1-6}$)alkyl, oxo, thioxo, $C_{2-6}$ alkylcarbonyl, carboxy, $C_{2-6}$ alkoxycarbonyl, amino, $C_{1-6}$ alkylamino, di($C_{1-6}$)alkylamino, bis[hydroxy($C_{1-6}$)alkyl]amino, $C_{1-6}$ alkylamino($C_{1-6}$)alkylamino, $C_{3-7}$ cycloalkylamino, arylamino, heteroarylamino, $C_{2-6}$ alkylcarbonylamino, $C_{2-6}$ alkoxycarbonylamino, ($C_{2-6}$)alkoxycarbonyl($C_{1-6}$)alkylamino, [($C_{2-6}$)alkoxycarbonyl][($C_{1-6}$)alkyl]amino, bis[($C_{2-6}$)alkoxycarbonyl($C_{1-6}$)alkyl]amino, $C_{2-6}$ alkoxycarbonylamino($C_{1-6}$)alkyl or aminocarbonyl; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents independently selected from $C_{1-6}$ alkyl, hydroxy and amino; and $R^1$, $R^2$ and $R^5$ are as defined above.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkynyl groups include ethynyl and prop-2-yn-1-yl.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, pyridinyl, quinolinyl, isoquinolinyl, pyridazinyl, pyrimidinyl, pyrazinyl and triazinyl groups.

The term "halogen" as used herein is intended to include fluorine, chlorine, bromine and iodine atoms.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

Suitable values of $R^1$ include hydrogen, halogen and $C_{1-6}$ alkyl. In one embodiment, $R^1$ represents hydrogen. In a particular embodiment, $R^1$ represents halogen, especially fluoro or chloro. In another embodiment, $R^1$ represents $C_{1-6}$ alkyl, especially methyl.

Suitably, $R^1$ represents halogen. In a particular embodiment, $R^1$ is fluoro. In another embodiment, $R^1$ is chloro.

Suitably, $R^2$ represents halogen, nitro, cyano, $C_{2-6}$ alkynyl, hydroxy($C_{1-6}$)alkyl or formyl. Typically, $R^2$ represents halogen, nitro, hydroxy($C_{1-6}$)alkyl or formyl.

In one embodiment, $R^2$ represents halogen, especially bromo or iodo, particularly iodo. In another embodiment, $R^2$ represents nitro. In another embodiment, $R^2$ represents cyano. In another embodiment, $R^2$ represents $C_{1-6}$ alkyl, especially methyl. In another embodiment, $R^2$ represents $C_{2-6}$ alkynyl, especially ethynyl. In a further embodiment, $R^2$ represents hydroxy($C_{1-6}$)alkyl, especially hydroxymethyl. In an additional embodiment, $R^2$ represents formyl.

In one embodiment, the heterocyclic ring of which Q is the residue is a three-membered heterocyclic ring. In another embodiment, the heterocyclic ring of which Q is the residue is a four-membered heterocyclic ring. In a further embodiment, the heterocyclic ring of which Q is the residue is a fivemembered heterocyclic ring. In an additional embodiment, the heterocyclic ring of which Q is the residue is a six-membered heterocyclic ring.

The heterocyclic ring of which Q is the residue will typically be a four-, five- or six-membered heterocyclic ring. The heterocyclic ring of which Q is the residue will suitably be a five- or six-membered heterocyclic ring.

In one embodiment, the heterocyclic ring of which Q is the residue is fully saturated, i.e. there is no double bond contained within the ring. In another embodiment, the heterocyclic ring of which Q is the residue is unsaturated, i.e. the ring contains one or two double bonds. In one aspect of that embodiment, the heterocyclic ring of which Q is the residue contains one double bond within the ring. In another aspect of that embodiment, the heterocyclic ring of which Q is the residue contains two double bonds within the ring.

Ideally, Q represents the residue of a three-, four-, five- or six-membered heterocyclic ring optionally containing a double bond, wherein the heterocyclic ring comprises one, two or three heteroatoms independently selected from oxygen, sulphur, nitrogen and phosphorus.

Typically, Q represents the residue of a four-, five- or six-membered heterocyclic ring optionally containing a double bond, wherein the heterocyclic ring comprises one, two or three heteroatoms independently selected from oxygen, sulphur, nitrogen and phosphorus.

Suitably, Q represents the residue of a five- or six-membered heterocyclic ring optionally containing a double bond, wherein the heterocyclic ring comprises one, two or three heteroatoms independently selected from oxygen, sulphur, nitrogen and phosphorus.

Typical heterocyclic rings of which Q is the residue include azetidinyl, tetrahydrofuryl, tetrahydrothienyl, pyrrolidinyl, dioxolanyl, oxazolidinyl, isoxazolidinyl, thiazolidinyl, isothiazolidinyl, imidazolidinyl, dioxaphospholanyl, oxathiazolidinyl, oxadiazolidinyl, oxaphosphazolidinyl, thiadiazolidinyl, phosphadiazolidinyl, oxazolinyl, isoxazolinyl, thiazolinyl, isothiazolinyl, imidazolinyl, triazolinyl, piperidinyl, tetrahydrooxazinyl, tetrahydrothiazinyl, hexahydropyridazinyl, hexahydropyrimidinyl, piperazinyl, tetrahydropyridinyl and tetrahydropyrimidinyl. An additional ring is imidazolyl.

Particular heterocyclic rings of which Q is the residue include azetidinyl, pyrrolidinyl, dioxolanyl, oxazolidinyl, thiazolidinyl, imidazolidinyl, dioxaphospholanyl, oxazolinyl, thiazolinyl, imidazolinyl, imidazolyl, piperidinyl and tetrahydrooxazinyl.

Suitable heterocyclic rings of which Q is the residue include azetidinyl, pyrrolidinyl, dioxolanyl, oxazolidinyl, imidazolidinyl, dioxaphospholanyl, oxazolinyl, thiazolinyl, imidazolinyl and tetrahydrooxazinyl.

Depending upon the nature of the heterocyclic ring of which Q is the residue, it may not be possible to accommodate all three substituents $R^3$, $R^4$ and $R^5$ around this ring. Thus, for certain values of Q, it will be appreciated that the substituent designated $R^5$ will be absent; and likewise, for certain other values of Q, it will be appreciated that the substituents designated $R^4$ and $R^5$ will both be absent. Moreover, for certain particular values of Q, it will be appreciated that the substituents designated $R^3$, $R^4$ and $R^5$ will all be absent.

General values of $R^3$ and/or $R^4$ include hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, nitro($C_{1-6}$)alkyl, halogen, cyano, trifluoromethyl, aryl, aryl($C_{1-6}$)alkyl, heteroaryl, heteroaryl($C_{1-6}$)alkyl, oxo, thioxo, $C_{2-6}$ alkylcarbonyl, carboxy, $C_{2-6}$ alkoxycarbonyl, amino, $C_{1-6}$ alkylamino, di($C_{1-6}$)alkylamino, bis[hydroxy($C_{1-6}$)alkyl]amino, $C_{1-6}$ alkylamino($C_{1-6}$)alkylamino, $C_{3-7}$ cycloalkylamino, arylamino, heteroarylamino, $C_{2-6}$ alkylcarbonylamino, $C_{2-6}$ alkoxycarbonylamino, ($C_{2-6}$)alkoxycarbonyl($C_{1-6}$)alkylamino, [($C_{2-6}$)alkoxycarbonyl][($C_{1-6}$)alkyl]amino, bis[($C_{2-6}$)alkoxycarbonyl($C_{1-6}$)alkyl]amino, $C_{2-6}$ alkoxycarbonylamino($C_{1-6}$)alkyl and aminocarbonyl.

Typical values of $R^3$ and/or $R^4$ include hydrogen, $C_{1-6}$ alkyl, $C_{1-6}$ alkoxy($C_{1-6}$)-alkyl, hydroxy, hydroxy($C_{1-6}$)alkyl, amino($C_{1-6}$)alkyl, aryl, aryl($C_{1-6}$)alkyl, heteroaryl, heteroaryl($C_{1-6}$)alkyl, oxo, thioxo, $C_{2-6}$ alkoxycarbonyl, amino, $C_{1-6}$ alkylamino, di($C_{1-6}$)alkylamino, $C_{3-7}$ cycloalkylamino, $C_{2-6}$ alkylcarbonylamino, $C_{2-6}$ alkoxycarbonylamino, ($C_{2-6}$) alkoxycarbonyl($C_{1-6}$)alkylamino, bis[($C_{2-6}$)alkoxycarbonyl ($C_{1-6}$)alkyl]amino, $C_{2-6}$ alkoxycarbonylamino($C_{1-6}$)alkyl and aminocarbonyl.

Favoured values of $R^3$ and/or $R^4$ include hydrogen, $C_{1-6}$ alkyl, hydroxy, aryl, $C_{3-7}$ heterocycloalkyl($C_{1-6}$)alkyl, oxo, thioxo, imino, $C_{2-6}$ alkylcarbonyl, $C_{2-6}$ alkoxycarbonyl, amino, $C_{1-6}$ alkylamino and $C_{3-7}$ cycloalkylamino.

Suitable values of $R^3$ and/or $R^4$ include hydrogen, $C_{1-6}$ alkyl, hydroxy, aryl, oxo, thioxo, amino and $C_{3-7}$ cycloalkylamino.

Particular values of $R^3$ and/or $R^4$ include hydrogen, methyl, ethyl, isopropyl, methoxy, isopropoxy, methylaminoethoxy, methoxymethyl, methylthio, ethylthio, methylsulphonyl, hydroxy, hydroxymethyl, hydroxyethyl, aminomethyl, nitromethyl, fluoro, chloro, bromo, cyano, trifluoromethyl, phenyl, benzyl, imidazolyl, imidazolylmethyl, oxo, thioxo, acetyl, carboxy, methoxycarbonyl, ethoxycarbonyl, tert-butoxycarbonyl, amino, methylamino, ethylamino, dimethylamino, bis[hydroxyethyl]-amino, ethylaminoethylamino, cyclopropylamino, phenylamino, pyridinylamino, acetylamino, tert-butoxycarbonylamino, methoxycarbonylethylamino, (tert-butoxycarbonyl)(methyl)amino, bis(ethoxycarbonylmethyl)amino, tert-butoxycarbonylamino-methyl and aminocarbonyl. Additional values include tert-butyl, imino and morpholinylmethyl.

Favourably, $R^3$ represents hydrogen, methyl, isopropyl, tert-butyl, hydroxy, phenyl, morpholinylmethyl, oxo, thioxo, imino, acetyl, tert-butoxycarbonyl, amino, methylamino, ethylamino or cyclopropylamino.

Suitably, $R^3$ represents hydrogen, methyl, hydroxy, phenyl, oxo, thioxo, amino or cyclopropylamino.

Favourably, $R^4$ represents hydrogen, methyl, hydroxy or oxo.

Suitably, $R^4$ represents hydrogen, methyl or hydroxy.

Alternatively, $R^3$ and $R^4$ may together form an optionally substituted spiro linkage. Thus, $R^3$ and $R^4$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents independently selected from $C_{1-6}$ alkyl, hydroxy and amino. In this context, $R^3$ and $R^4$, when taken together with the carbon atom to which they are both attached, may suitably represent an optionally substituted cyclopentyl, cyclohexyl, pyrrolidine or piperidine ring. In particular, $R^3$ and $R^4$, when taken together with the carbon atom to which they are both attached, may suitably represent an optionally substituted piperidine ring.

In a particular embodiment, $R^5$ represents hydrogen. In another embodiment, $R^5$ represents $C_{1-6}$ alkyl, especially methyl.

Particular sub-classes of compounds in accordance with the present invention are represented by the compounds of formula (IA), (IB), (IC), (ID), (IE), (IF), (IG), (IH), (IJ), (IK), (IL), (IM), (IN) and (IP):
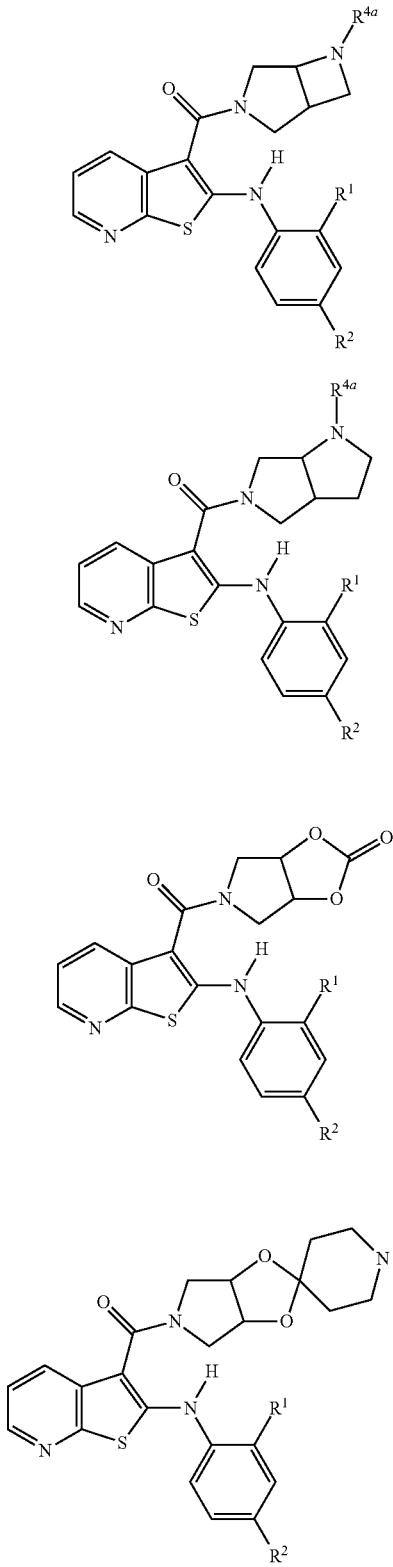
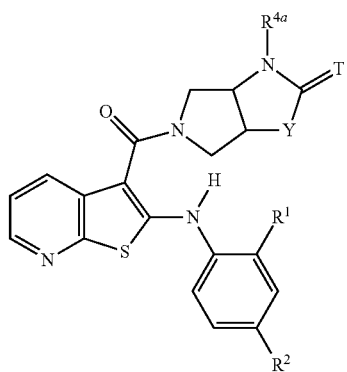
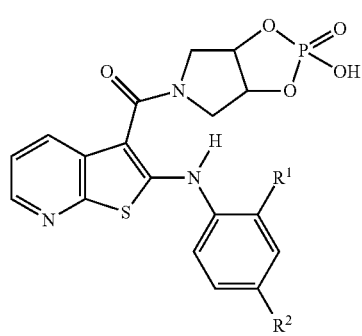
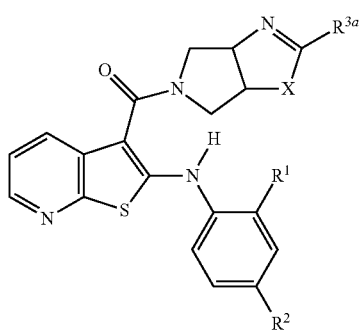
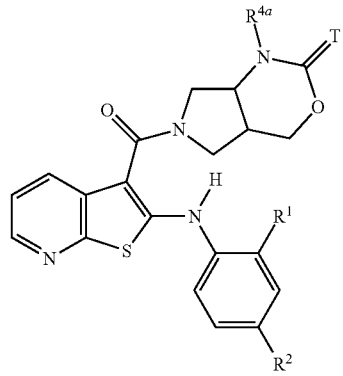

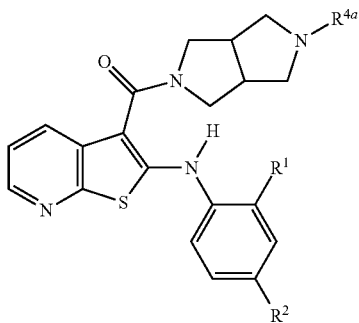

(IJ)

(IK)

(IL)

(IM)

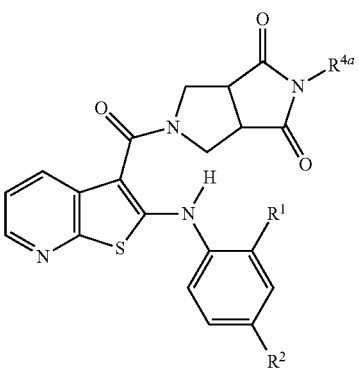

(IN)

(IP)

wherein
T represents oxygen, sulphur or NH;
X represents oxygen, sulphur or N—$R^{4a}$;
Y represents oxygen, sulphur, N—$R^5$ or $CH_2$;
$R^{3a}$ represents hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylthio, $C_{1-6}$ alkylsulphonyl, hydroxy($C_{1-6}$)alkyl, amino($C_{1-6}$)-alkyl, nitro($C_{1-6}$)alkyl, halogen, cyano, trifluoromethyl, aryl, aryl($C_{1-6}$)alkyl, heteroaryl, heteroaryl($C_{1-6}$)alkyl, $C_{2-6}$ alkylcarbonyl, carboxy, $C_{2-6}$ alkoxycarbonyl, amino, $C_{1-6}$ alkylamino, di($C_{1-6}$)alkylamino, bis[hydroxy($C_{1-6}$)alkyl]amino, $C_{1-6}$ alkylamino($C_{1-6}$)-alkylamino, $C_{3-7}$ cycloalkylamino, arylamino, heteroarylamino, $C_{2-6}$ alkylcarbonylamino, $C_{2-6}$ alkoxycarbonylamino, ($C_{2-6}$)alkoxycarbonyl($C_{1-6}$)alkylamino, [($C_{2-6}$)alkoxycarbonyl]-[($C_{1-6}$)alkyl]amino, bis[($C_{2-6}$)alkoxycarbonyl($C_{1-6}$)alkyl]amino, $C_{2-6}$ alkoxycarbonylamino($C_{1-6}$)alkyl or aminocarbonyl;
$R^{4a}$ represents hydrogen, $C_{1-6}$ alkyl, $C_{1-6}$ alkoxy, $C_{1-6}$ alkylamino($C_{1-6}$)alkoxy, $C_{1-6}$ alkoxy($C_{1-6}$)alkyl, $C_{1-6}$ alkylsulphonyl, hydroxy, hydroxy($C_{1-6}$)alkyl, amino($C_{1-6}$)alkyl, nitro($C_{1-6}$)alkyl, trifluoromethyl, aryl, aryl($C_{1-6}$)alkyl, $C_{3-7}$ heterocycloalkyl($C_{1-6}$)alkyl, heteroaryl, heteroaryl($C_{1-6}$) alkyl, $C_{2-6}$ alkylcarbonyl, carboxy, $C_{2-6}$ alkoxycarbonyl, $C_{2-6}$ alkoxycarbonylamino($C_{1-6}$)alkyl or aminocarbonyl;
$R^{6a}$ represents hydrogen or $C_{1-6}$ alkyl; and
$R^1$, $R^2$ and $R^5$ are as defined above.

Specific sub-classes of compounds in accordance with the present invention are represented by the compounds of formula (IA), (IB), (IC), (ID), (IE), (IF), (IG) and (IH) as depicted above, wherein $R^1$, $R^2$, T, X, Y, $R^{3a}$, $R^{4a}$ and $R^{6a}$ are as defined above.

Suitably, T represents oxygen or sulphur.

In one embodiment, T represents oxygen. In another embodiment, T represents sulphur. In a further embodiment, T represents NH.

In one embodiment, X represents oxygen. In another embodiment, X represents sulphur. In a further embodiment, X represents N—$R^{4a}$.

Suitably, Y represents oxygen, sulphur or N—$R^5$, in which $R^5$ is as defined above.

Typically, Y represents oxygen or N—$R^5$.

In one embodiment, Y represents oxygen. In another embodiment, Y represents sulphur. In another embodiment, Y represents N—$R^5$. In a further embodiment, Y represents $CH_2$.

Typically, $R^{3a}$ represents $C_{1-6}$ alkyl, aryl, amino, $C_{1-6}$ alkylamino or $C_{3-7}$ cycloalkylamino. Suitably, $R^{3a}$ represents $C_{1-6}$ alkyl, aryl, amino or $C_{3-7}$ cycloalkylamino.

Favourable values of $R^{3a}$ include methyl, isopropyl, tert-butyl, phenyl, amino, methylamino, ethylamino and cyclopropylamino. Suitable values of $R^{3a}$ include methyl, phenyl, amino and cyclopropylamino.

Typically, $R^{4a}$ represents hydrogen, $C_{1-6}$ alkyl, $C_{1-6}$ alkoxy, $C_{1-6}$ alkylamino-($C_{1-6}$)alkoxy, $C_{1-6}$ alkoxy($C_{1-6}$)alkyl, $C_{1-6}$ alkylsulphonyl, hydroxy, hydroxy($C_{1-6}$)alkyl, amino($C_{1-6}$)alkyl, nitro($C_{1-6}$)alkyl, trifluoromethyl, aryl, aryl($C_{1-6}$)alkyl, heteroaryl, heteroaryl($C_{1-6}$)alkyl, $C_{2-6}$ alkylcarbonyl, carboxy, $C_{2-6}$ alkoxycarbonyl, $C_{2-6}$ alkoxycarbonylamino($C_{1-6}$)alkyl or aminocarbonyl.

Illustrative values of $R^{4a}$ include hydrogen, $C_{1-6}$ alkyl, $C_{3-7}$ heterocycloalkyl-($C_{1-6}$)alkyl, $C_{2-6}$ alkylcarbonyl and $C_{2-6}$ alkoxycarbonyl.

Suitably, $R^{4a}$ represents hydrogen or $C_{1-6}$ alkyl.

Particular values of $R^{4a}$ include hydrogen, methyl, morpholinylmethyl, acetyl and tert-butoxycarbonyl.

In one embodiment, $R^{4a}$ represents hydrogen. In another embodiment, $R^{4a}$ represents $C_{1-6}$ alkyl, especially methyl. In a further embodiment, $R^{4a}$ represents $C_{3-7}$ heterocycloalkyl ($C_{1-6}$)alkyl, especially morpholinylmethyl. In a still further embodiment, $R^{4a}$ represents $C_{2-6}$ alkylcarbonyl, especially acetyl. In an additional embodiment, $R^{4a}$ represents $C_{2-6}$ alkoxycarbonyl, especially tert-butoxycarbonyl.

In a particular embodiment, $R^{ha}$ represents hydrogen. In another embodiment, $R^{6a}$ represents $C_{1-6}$ alkyl, especially methyl.

The ring fusion between the pyrrolidine ring and its neighbouring fused ring in the compounds of formula (IA) to (IG) as depicted above, and also in the compounds of formula (IJ), (IK), (IL), (IN) and (IP) as depicted above, is suitably in the cis configuration, giving rise to the following compounds:

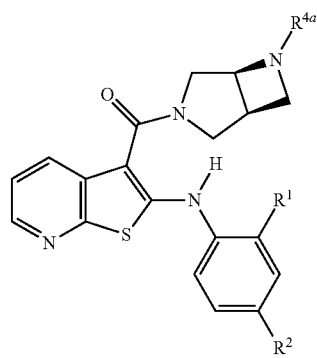
(IA-1)

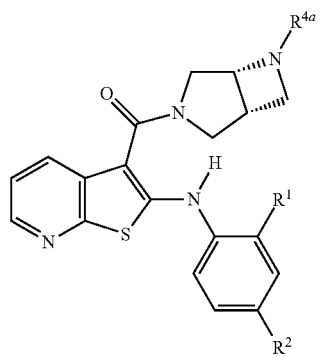
(IA-2)

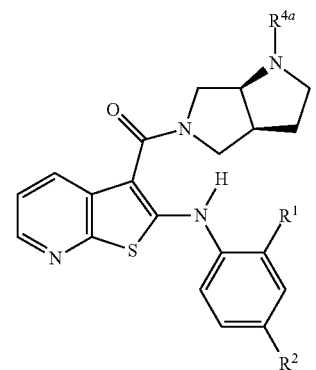
(IB-1)

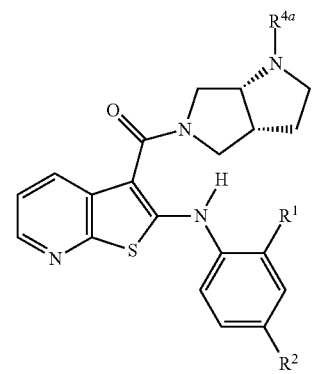
(IB-2)

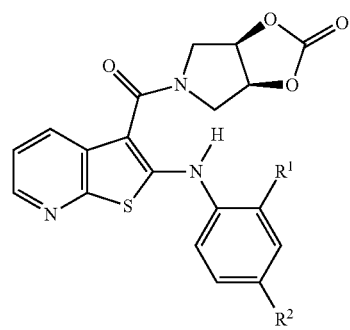
(IC-1)

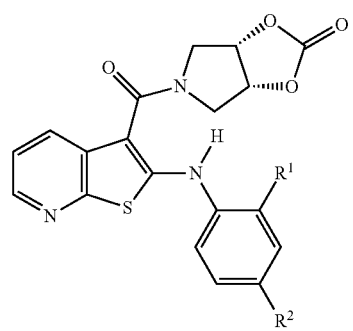
(IC-2)
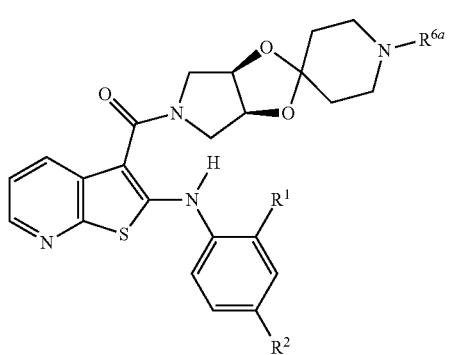
(ID-1)
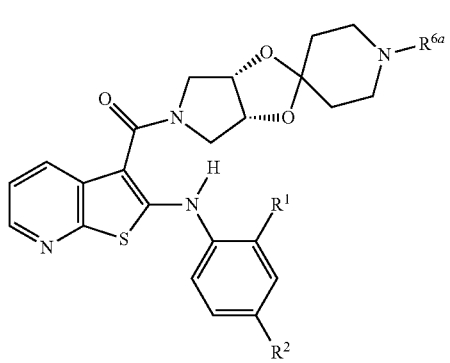
(ID-2)
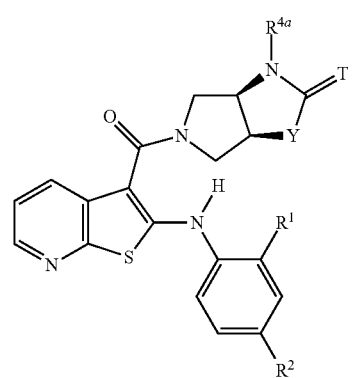
(IE-1)
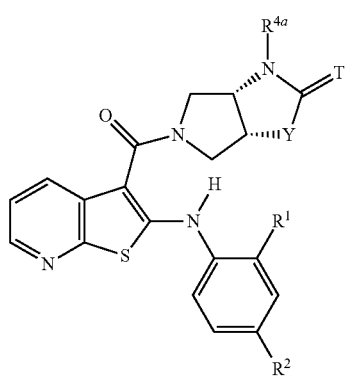
(IE-2)
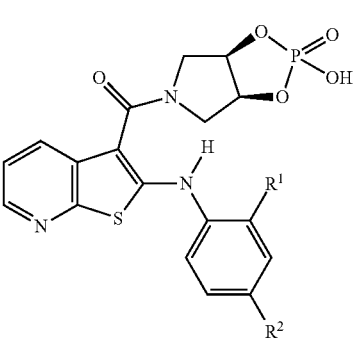
(IF-1)
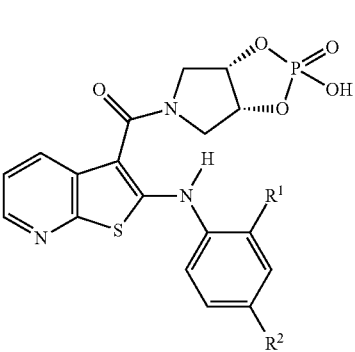
(IF-2)
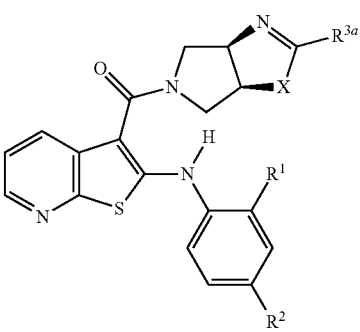
(IG-1)

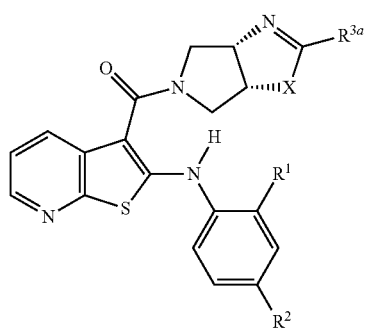
(IG-2)
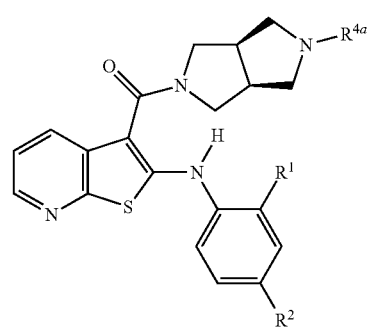
(IJ-1)
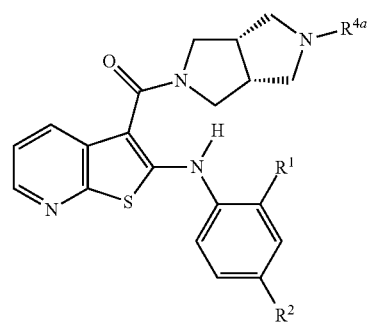
(IJ-2)
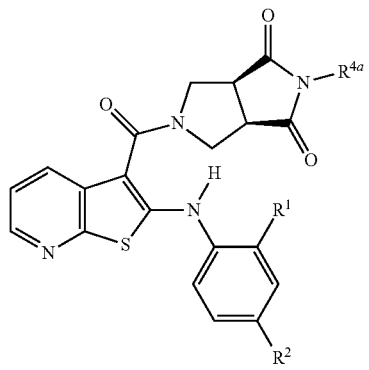
(IK-1)
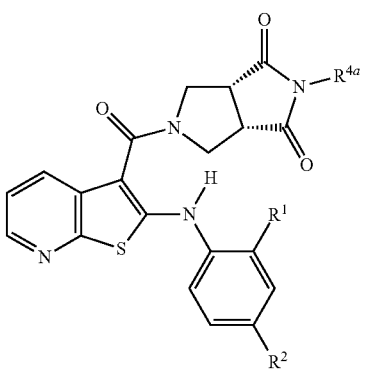
(IK-2)
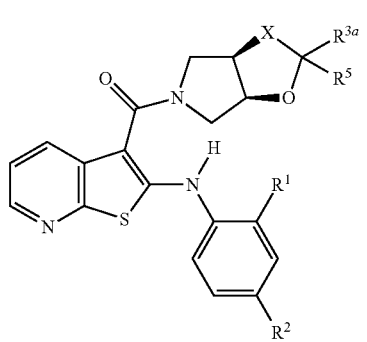
(IL-1)
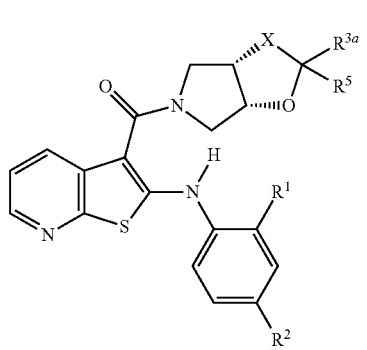
(IL-2)
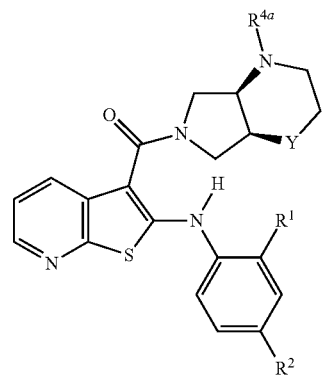
(IN-1)

-continued (IN-2)
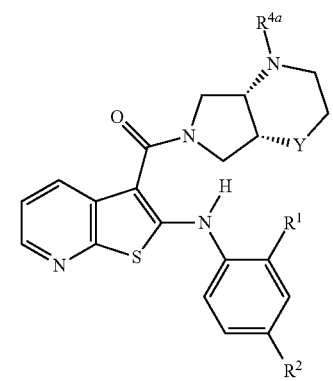

(IP-1)
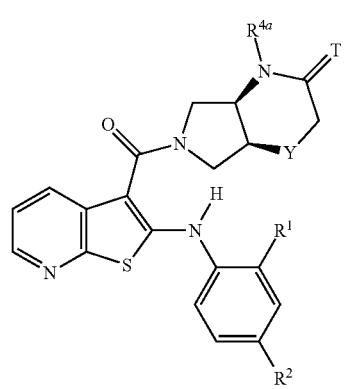

(IP-2)
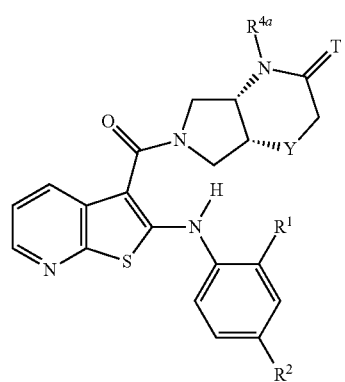

(IH-1)
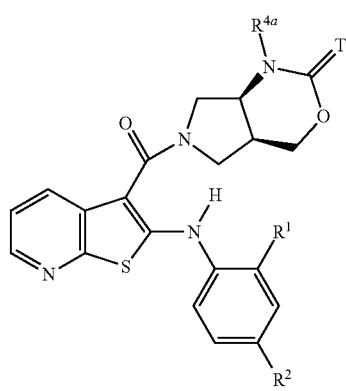

(IH-2)
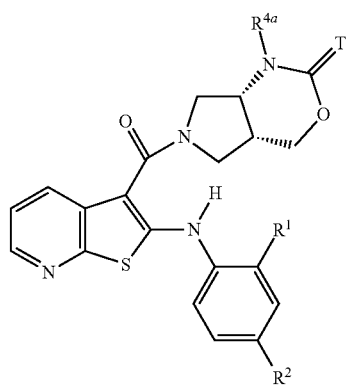

(IH-3)
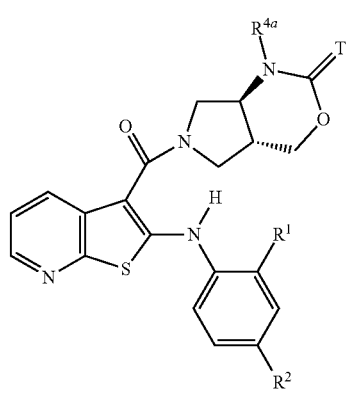

(IH-4)

wherein $R^1$, $R^2$, $R^5$, T, X, Y, $R^{3a}$, $R^{4a}$ and $R^{6a}$ are as defined above.

The ring fusion between the pyrrolidine ring and its neighbouring fused ring in the compounds of formula (IH) as depicted above may be in the cis or trans configuration, giving rise to the following compounds:

wherein $R^1$, $R^2$, T and $R^{4a}$ are as defined above.

One sub-class of compounds according to the invention is represented by the compounds of formula (IIA), and pharmaceutically acceptable salts, solvates and N-oxides thereof:

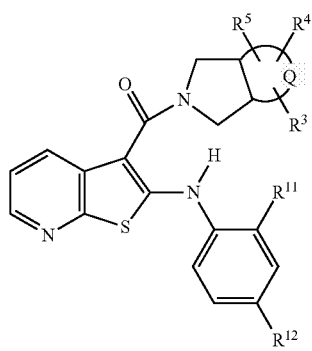

(IIA)

wherein
Q, $R^3$, $R^4$ and $R^5$ are as defined above;
$R^{11}$ represents halogen; and
$R^{12}$ represents halogen, nitro, cyano, $C_{2-6}$ alkynyl, hydroxy($C_{1-6}$)alkyl or formyl.

In one specific embodiment, $R^{11}$ is fluoro. In another specific embodiment, $R^{11}$ is chloro.

Typically, $R^{12}$ represents halogen, nitro, hydroxy($C_{1-6}$)alkyl or formyl.

In one embodiment, $R^{12}$ represents halogen, especially iodo. In another embodiment, $R^{12}$ represents nitro. In another embodiment, $R^{12}$ represents cyano. In another embodiment, $R^{12}$ represents $C_{2-6}$ alkynyl, especially ethynyl. In a further embodiment, $R^{12}$ represents hydroxy($C_{1-6}$)alkyl, especially hydroxymethyl. In an additional embodiment, $R^{12}$ represents formyl.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound of formula (I) as defined above, or a pharmaceutically acceptable salt, solvate or N-oxide thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

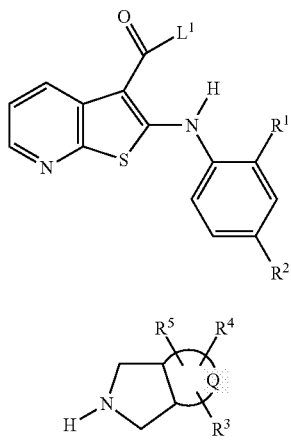

wherein Q, $R^1$, $R^2$, $R^3$, $R^4$ and $R^5$ are as defined above, and $L^1$ represents a suitable leaving group.

The leaving group $L^1$ is typically a halogen atom, e.g. fluoro.

The reaction is conveniently effected in a suitable solvent, e.g. a dipolar aprotic solvent such as N,N-dimethylformamide, or a chlorinated solvent such as dichloromethane, typically under basic conditions, e.g. in the presence of an organic base such as N,N-diisopropylethylamine or diisopropylamine.

The intermediates of formula (III) wherein $L^1$ is fluoro may suitably be prepared by reacting a compound of formula (V):

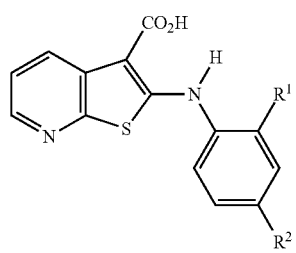

wherein $R^1$ and $R^2$ are as defined above; with diethylaminosulfur trifluoride (DAST).

The reaction is conveniently effected in a suitable solvent, e.g. dichloromethane.

The intermediates of formula (V) above may suitably be prepared by reacting a compound of formula (VI) with a compound of formula (VII):

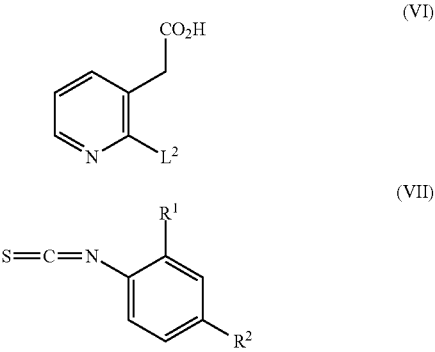

wherein $R^1$ and $R^2$ are as defined above, and $L^2$ represents a suitable leaving group.

The leaving group $L^2$ is typically a halogen atom, e.g. chloro.

The reaction is conveniently effected, at an elevated temperature if necessary, in a suitable solvent, e.g. tetrahydrofuran, typically under basic conditions, e.g. in the presence of lithium diisopropylamide.

The intermediates of formula (VII) above may be prepared by the procedure described in WO 2007/088345.

The compounds of formula (IC), the compounds of formula (IE) wherein T and Y both represent oxygen, and the compounds of formula (IH) wherein T represents oxygen, all as depicted above, may be prepared by a process which comprises reacting a compound of formula (VIII), (IX) or (X) respectively:

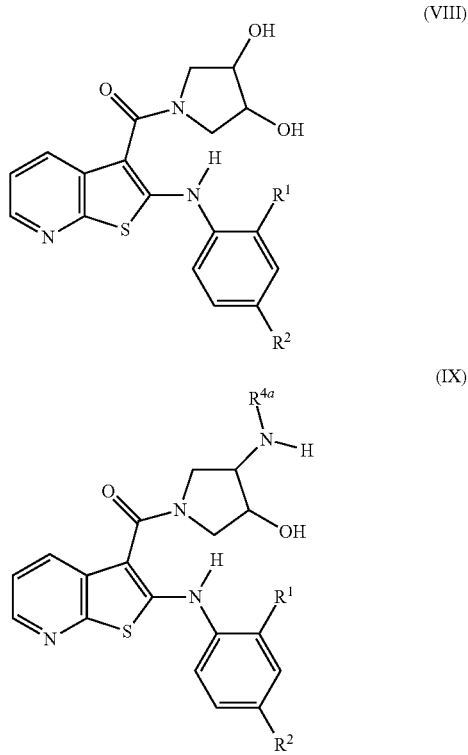

(X)

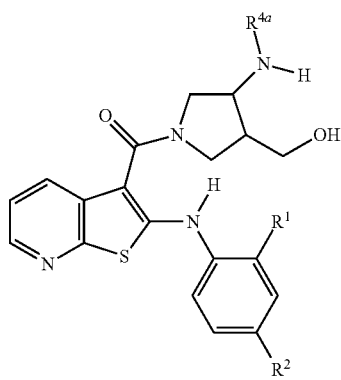

wherein $R^1$, $R^2$ and $R^{4a}$ are as defined above; with 1,1'-carbonyldiimidazole.

The reaction is conveniently effected in a suitable solvent, e.g. N,N-dimethylformamide.

The compounds of formula (IH) as depicted above wherein T represents sulphur may be prepared by a process which comprises reacting a compound of formula (X) as defined above with 1,1'-thiocarbonyldiimidazole. The reaction is conveniently effected in a suitable solvent, e.g. N,N-dimethylformamide.

The intermediates of formula (VIII), (IX) and (X) above may suitably be prepared by reacting a compound of formula (III) as defined above with a compound of formula (XI), (XII) or (XIII) respectively:

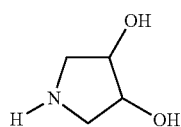
(XI)

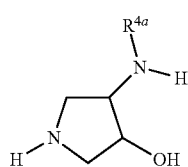
(XII)

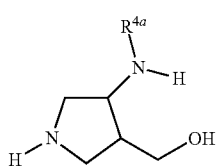
(XIII)

wherein $R^{4a}$ is as defined above; under conditions analogous to those described above for the reaction between compounds (III) and (IV).

Alternatively, the intermediates of formula (X) above may be prepared by reacting a compound of formula (III) as defined above with a compound of formula (XIV):

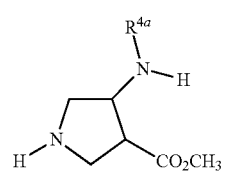
(XIV)

wherein $R^{4a}$ is as defined above; under conditions analogous to those described above for the reaction between compounds (III) and (IV); followed by reduction of the methyl ester group, typically by using a standard reducing agent such as an alkali metal borohydride, e.g. lithium borohydride.

The compounds of formula (ID) as depicted above may be prepared by a process which comprises reacting a compound of formula (VIII) as defined above with a compound of formula (XV):

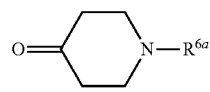
(XV)

wherein $R^{6a}$ is as defined above.

The reaction is suitably effected under acidic conditions, typically in the presence of a catalytic quantity of p-toluenesulphonic acid, in which case the reaction is conveniently carried out at ambient or elevated temperature in an inert organic solvent, e.g. a hydrocarbon solvent such as toluene.

The compounds of formula (IF) as depicted above may be prepared by a process which comprises reacting a compound of formula (VIII) as defined above with a phosphoric acid dihalide ester, e.g. methyl dichlorophosphate.

The reaction is conveniently effected at an elevated temperature in a suitable solvent, e.g. an ethereal solvent such as tetrahydrofuran, typically under basic conditions, e.g. in the presence of an organic base such as N,N-diisopropylethylamine.

The compounds of formula (IL) as depicted above wherein X represents oxygen or N—$R^{4a}$ may be prepared by a process which comprises reacting a compound of formula (VIII) or (IX) respectively, as defined above, with a compound of formula (XVI), or a carbonyl-protected form thereof:

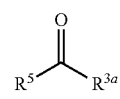
(XVI)

wherein $R^5$ and $R^{3a}$ are as defined above; under conditions analogous to those described above for the reaction between compounds (VIII) and (XV).

Suitable carbonyl-protected forms of the compounds of formula (XVI) include the dimethyl acetal or ketal derivatives thereof. A particular carbonyl-protected compound of formula (XVI) is 2,2-dimethoxypropane.

The compounds of formula (IG) as depicted above wherein X represents oxygen or sulphur and $R^{3a}$ represents $C_{1-6}$ alkylamino or $C_{3-7}$ cycloalkylamino may be prepared by a process which comprises reacting a compound of formula (XVII):

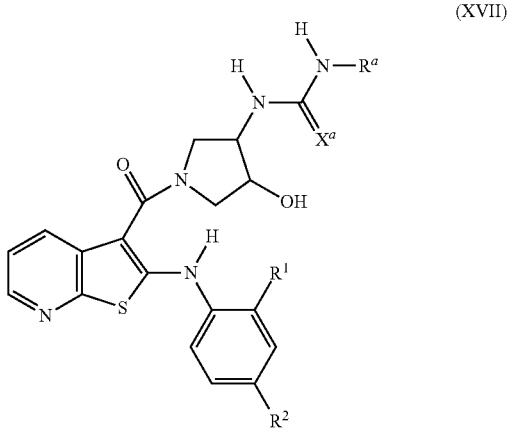

(XVII)

wherein $R^1$ and $R^2$ are as defined above, $X^a$ represents oxygen or sulphur, and $R^a$ represents $C_{1-6}$ alkyl or $C_{3-7}$ cycloalkyl; with DAST.

In an alternative procedure, the compounds of formula (IE) as depicted above wherein T represents sulphur, Y represents NH and $R^{4a}$ represents $C_{1-6}$ alkyl or $C_{3-7}$ cycloalkyl may also be prepared by a process which comprises reacting a compound of formula (XVII) as defined above, wherein $X^a$ represents sulphur, with DAST.

The reaction between compound (XVII) and DAST is conveniently effected in a suitable solvent, e.g. a chlorinated solvent such as dichloromethane.

The intermediates of formula (XVII) above may suitably be prepared by reacting a compound of formula (IX) as defined above wherein $R^{4a}$ represents hydrogen with the appropriate isocyanate or isothiocyanate derivative of formula $R^a$—N=C=$X^a$, wherein $R^a$ and $X^a$ are as defined above. The reaction may conveniently be effected in a suitable solvent, e.g. a cyclic ether such as tetrahydrofuran, or a chlorinated solvent such as dichloromethane.

Alternatively, the intermediates of formula (XVII) above may be prepared by reacting a compound of formula (III) as defined above with a compound of formula (XVIII):

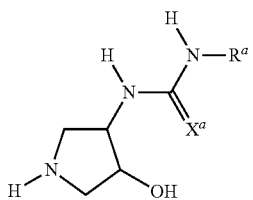

(XVIII)

wherein $X^a$ and $R^a$ are as defined above; under conditions analogous to those described above for the reaction between compounds (III) and (IV).

The intermediates of formula (XVIII) above may be prepared by reacting a compound of formula (XII) as defined above wherein $R^{4a}$ represents hydrogen, or a protected derivative thereof, e.g. a compound of formula (XII) having a tert-butoxycarbonyl protecting group attached at the 1-position of the pyrrolidine ring, with the appropriate isocyanate or isothiocyanate derivative of formula $R^a$—N=C=$X^a$, wherein $R^a$ and $X^1$ are as defined above, under conditions analogous to those described above for the reaction between compound (IX) wherein $R^{4a}$ represents hydrogen and the compound of formula $R^1$—N=C=$X^a$; followed, where necessary, by deprotection. Where the protecting group is a tert-butoxycarbonyl group attached at the 1-position of the pyrrolidine ring, deprotection may be effected by treatment with an acid, e.g. a mineral acid such as hydrochloric acid, or an organic acid such as trifluoroacetic acid.

Where they are not commercially available, the starting materials of formula (IV), (VI), (XI), (XII), (XIII), (XIV), (XV) and (XVI) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (IA), (IB), (IE), (IH), (IJ), (IK), (IN) or (IP) wherein $R^{4a}$ represents tert-butoxycarbonyl may be converted into the corresponding compound wherein $R^{4a}$ represents hydrogen by treatment with an acid, typically an organic acid such as trifluoroacetic acid, or a mineral acid such as hydrochloric acid.

A compound of formula (IE) wherein $R^{4a}$ represents hydrogen may be converted into the corresponding compound wherein $R^{4a}$ represents morpholin-4-ylmethyl by treatment with morpholine and formaldehyde, typically at an elevated temperature.

The pyridine-N-oxide derivative of a compound of formula (I) may be converted into the corresponding compound of formula (I) by treatment with triphenylphosphine and phosphorus trichloride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human MEK enzyme.

In Vitro MEK Assay

MEK1 activity was measured in a cascade assay initiated by active Raf, via activation of MEK, Erk2 and subsequent phosphorylation of fluorescein-labelled Erk-tide substrate in an assay based on fluorescence polarisation (IMAP). The assay was carried out in 20 mM Tris+5 mM MgCl$_2$+2 mM DL-dithiothreitol+0.01% Tween 20 pH 7.2, containing 1.5 nM unactive MEK, 100 nM unactive Erk and 200 nM Erk-tide (all concentrations are final concentrations). Compounds, or DMSO controls, were tested at a final concentration of 2% DMSO, and the assay initiated in the presence of 5 μM ATP by addition of 1.25 nM active Raf in assay buffer. After 20 min at r.t., stop solution was added followed by IMAP binding beads, the assay mixture was then incubated for 90 min at r.t. (with shaking) and then read on a Molecular Devices LJL HT reader.

When tested in the above assay, the compounds of the accompanying Examples were all found to inhibit human MEK enzyme with IC$_{50}$ values of 10 μM or better.

EXAMPLES

Abbreviations

DMSO: dimethylsulphoxide
THF: tetrahydrofuran
DCM: dichloromethane
MeOH: methanol
EtOH: ethanol
EtOAc: ethyl acetate
Et$_2$O: diethyl ether
DMF: N,N-dimethylformamide
DAST: diethylaminosulfur trifluoride
HOB T: 1-hydroxybenzotriazole
TFA: trifluoroacetic acid
DIPEA: N,N-diisopropylethylamine
DBU: 1,8-diazabicyclo[5.4.0]undec-7-ene
CDI: 1,1'-carbonyldiimidazole
MCPBA: 3-chloroperoxybenzoic acid
EDC: 1-[3-(dimethylamino)propyl]-3-ethylcarbodiimide hydrochloride
SiO$_2$: silica
CDCl$_3$: deuterochloroform
quant.: quantitative
r.t.: room temperature
h: hour(s)
min. minute(s)
sat.: saturated
RT: retention time
HPLC: high performance liquid chromatography
LCMS: liquid chromatography mass spectrometry
ES: electrospray All NMR spectra were obtained either at 300 MHz or 400 MHz.

Compounds were named with the aid of ACD Labs Name (v. 7.0) supplied by Advanced Chemical Development, Toronto, Canada.

Standard LCMS Method

The LC-MS system used comprises a Waters Alliance 2795 HT quaternary HPLC, Waters 996 Photo Diode Array (PDA) detector and Waters ZQ 4000 single quadrupole mass spectrometer. The ZQ can acquire data simultaneously in positive and negative electrospray ionisation modes.

ZQ Mass Spectrometer

| Capillary | 3.5 kV | Cone | 50 V |
|---|---|---|---|
| Extractor | 2 V | Source Temp | 80° C. |
| Desolvation Temp | 200° C. | Cone Gas | 150 L/h |
| Desolvation Gas | 250 L/h | Multiplier | 650 V |

Data were acquired in a full scan from 100 to 1000 m/z.

| Scan duration | 0.80 s |
|---|---|
| Interscan delay | 0.20 s |

HPLC

Analytical reverse phase separation was carried out on a Gemini C18 from Phenomenex 50×4.6 mm with 5 μm silica.

| Injection Volume | 5 μL |
|---|---|
| UV data | 240 to 400 nm |
| Sample Temperature | 20° C. |
| Column Temperature | 30° C. |
| Flow Rate | 0.9 mL/min |
| Split to ZQ | ~0.40 mL/min |

Solvent A: 90% 10 mM NH$_4$HCO$_2$ in water/0.1% formic acid/10% CH$_3$CN
Solvent B: 90% CH$_3$CN/0.1% formic acid/10% 10 mM NH$_4$HCO$_2$ in water
Solvent C: 90% 10 mM NH$_4$HCO$_2$ in water/0.1% ammonia/10% CH$_3$CN
Solvent D: 90% CH$_3$CN/10% 10 mM NH$_4$HCO$_2$ in water/0.1% ammonia Gradient Program For method 5_95_pH=3

| Time (min) | A % | B % | Flow | Curve |
|---|---|---|---|---|
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

For method 5_95_pH=10

| Time (min) | A % | B % | Flow | Curve |
|---|---|---|---|---|
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

Preparative UV-HPLC

The LC system comprises a Waters 2525 quaternary pump, a Waters 996 Photo Diode Array (PDA) detector, a Waters 2700 sample manager, a Column Fluidics Organiser and a Waters Fraction Collector operating in reverse phase at one of two pH systems.

Low pH System (Approximately pH 3.2)

The reverse phase separation was carried out on a Luna C18 from Phenomenex 100×21.2 mm with 5 μm silica.

| Injection Volume | 500 μL |
|---|---|
| UV data | 254 nm |
| Flow Rate | 20 mL/min |
| Solvent A | 90% water/10% CH$_3$CN/0.1% formic acid |
| Solvent B | 90% CH$_3$CN/10% water/0.1% formic acid |

High pH System (Approximately pH 9.5)

The reverse phase separation was carried out on a Gemini C18 from Phenomenex 150×21.2 mm with 10 μm silica.

| Injection Volume | 500 μL |
|---|---|
| UV data | 254 nm |
| Flow Rate | 20 mL/min |

Solvent C 90% 10 mM NH$_4$HCO$_2$ in water/0.1% ammonia/10% CH$_3$CN
Solvent D 90% CH$_3$CN/10% 10 mM NH$_4$HCO$_2$ in water/0.1% ammonia Typical gradient profiles are described below:

| Gradient Program for Low pH Method | | | | | | |
|---|---|---|---|---|---|---|
| Time | A % | B % | C % | D % | Flow | Curve |
| 0.00 | 95.0 | 5.0 | 0.0 | 0.0 | 20 | 1 |
| 9.00 | 5.0 | 95.0 | 0.0 | 0.0 | 20 | 6 |
| 11.00 | 5.0 | 95.0 | 0.0 | 0.0 | 20 | 6 |
| 11.50 | 95.0 | 5.0 | 0.0 | 0.0 | 20 | 6 |
| 12.00 | 95.0 | 5.0 | 0.0 | 0.0 | 20 | 6 |

| Gradient Program for High pH Method | | | | | | |
|---|---|---|---|---|---|---|
| Time | A % | B % | C % | D % | Flow | Curve |
| 0.00 | 0.0 | 0.0 | 95.0 | 5.0 | 20 | 1 |
| 9.00 | 0.0 | 0.0 | 5.0 | 95.0 | 20 | 6 |
| 11.00 | 0.0 | 0.0 | 5.0 | 95.0 | 20 | 6 |
| 11.50 | 0.0 | 0.0 | 95.0 | 5.0 | 20 | 6 |
| 12.00 | 0.0 | 0.0 | 95.0 | 5.0 | 20 | 6 |

Intermediate 1

2-Chloro-3-(chloromethyl)pyridine

To a 500 mL, round-bottom, 3-necked flask equipped with dropping funnel and magnetic stirrer and set for reflux was prepared a solution of 2-chloro-3-(hydroxymethyl)-pyridine (25.0 g, 174 mmol) in DCM (250 mL) under positive nitrogen atmosphere. The solution was cooled to 10° C. and thionyl chloride (31.0 g) was added dropwise over 25 minutes (exothermic). The reaction was then heated to reflux for 90 minutes, at which point the reaction was deemed complete by HPLC. The reaction mixture was cooled below boiling point and the equipment set for distillation. A total of 110 mL of DCM was initially removed and replenished with fresh DCM (110 mL), followed by another 80 mL of DCM before cooling the solution to 5-10° C. The acidic mixture was treated with a saturated solution of sodium bicarbonate (3 volumes) to pH 10. The lower organic phase was separated and the aqueous phase extracted with DCM (2 volumes). The organic phases were gathered, dried on sodium sulfate, filtered and concentrated in vacuo to afford the title compound as a pale yellow oil in excellent purity and yield (24.8 g, 88%). δ$_H$ (d$_6$-DMSO, 300 MHz) 8.45 (1H, dd), 8.10 (1H, dd), 7.50 (1H, dd), 4.85 (2H, s). LCMS (ES)$^+$ RT 3.00 min, m/e 162.1.

Intermediate 2

(2-Chloropyridin-3-yl)acetonitrile

In a 3 L reactor, set for reflux under positive nitrogen pressure and using a bleach scrubber, was prepared a solution of potassium cyanide (68.32 g, 1.04M) in EtOH (136 mL) and water (255 mL). The mixture was heated to reflux, at which point a solution of 2-chloro-3-(chloromethyl)pyridine (Intermediate 1; 170.0 g, 1.04M) in EtOH (170 mL) was added dropwise over 30 minutes. The whole mixture was maintained at reflux for a further 150 minutes. The mixture was then allowed to cool just below boiling point and the equipment set for distillation. A total of 8.5 volumes of EtOH were removed. On cooling, half a volume of water was added. At a temperature of 40° C., the solution was seeded and crystallised instantaneously. The thick beige slurry was allowed to cool to ambient temperature and then to 0° C. This mixture was filtered, rinsed with cold water (2 vols) and dried at 45° C. in a vacuum oven overnight. The title compound was afforded as a beige solid in excellent yield and purity (126.9 g, 80%). δ$_H$ (d$_6$-DMSO, 300 MHz) 8.45 (1H, dd), 8.00 (1H, dd), 7.50 (1H, dd), 4.15 (2H, s). LCMS (ES)$^+$ RT 2.15 min, m/e 153.01 & 155.01 (M+1 & M+3, Product).

Intermediate 3

(2-Chloropyridin-3-yl)acetic acid

To a 2 L reactor, set for reflux, was stirred a pre-prepared 15% w/w solution of sodium hydroxide (5 vols) to which was added (2-chloropyridin-3-yl)acetonitrile (Intermediate 2; 276.4 g, 1.81M). The beige suspension was heated to reflux for 30 minutes, at which point the reaction was deemed complete by HPLC. The brown solution was then cooled to 0-5° C. and acidified to pH 1 with conc. HCl while keeping the temperature below 10° C., using concentrated hydrochloric acid (1.8 vols). An off-white solid precipitated and was left to mature for another hour before filtration. Once dried, the material was recrystallised from propan-2-ol (4 vols) to afford the title compound as an off-white material in excellent yield and purity (280.3 g, 90%). δ$_H$ (d$_6$-DMSO, 300 MHz) 12.70 (1H, s), 8.35 (1H, dd), 7.85 (1H, dd), 7.40 (1H, dd), 4.25 (2H, s). LCMS (ES)$^+$ RT 1.75 min, m/e 171.99 (M+1, Product).

Intermediate 4

2-[2-Fluoro-4-iodophenyl)amino]thieno[2,3-b]pyridine-3-carboxylic acid

To a stirred solution of diisopropylamine (35.3 mL, 250 mmol) in anhydrous THF (200 mL) cooled to −15° C. was added n-butyllithium (100 mL, 2.5M in hexanes, 250 mmol) slowly such that an internal temperature of between −10 and 0° C. was maintained. The resultant mixture was stirred at room temperature for 15 minutes before being cooled to 0° C. The solution of lithium diisopropylamide was added via cannula to a rapidly stirred suspension of (2-chloropyridin-3-yl) acetic acid (Intermediate 3; 21.4 g, 125 mmol) in anhydrous THF (400 mL) at 0° C. The temperature of the reaction mixture was maintained at 0° C. over the course of the addition. Upon complete addition of the lithium diisopropylamide solution the resultant bright yellow suspension was stirred at 0° C. for 15 minutes. A solution of 2-fluoro-4-iodo-1-isothiocyanatobenzene (WO 2007/088345) (34.9 g, 125 mmol) in anhydrous THF (200 mL) was then added to the reaction mixture via cannula and the mixture heated to 65° C. for 18 hours. The reaction mixture was cooled and the volatiles removed in vacuo. The resultant brown gum was redissolved in THF (200 mL), cooled to 0° C. and 10% aqueous acetic acid (500 mL) added slowly. Acetonitrile (~200 mL) was added slowly until a brown solid developed; the solid was isolated by filtration and washed with successive portions of diethyl ether and acetonitrile to give the title compound as a yellow crystalline solid (11.0 g, 21%). $\delta_H$ (DMSO-$d_6$) 8.42 (1H, d, J 6.7 Hz), 8.22 (1H, m), 7.73 (1H, m), 7.61 (1H, m), 7.46 (1H, t, J 8.6 Hz), 7.35-7.31 (1H, m). Exchangeable protons were not observed. LCMS (pH 10) RT 1.82 minutes, ES$^+$ 415 (M+H)$^+$, ES$^-$ 413 (M−H)$^-$.

Intermediate 5

2-[2-Fluoro-4-iodophenyl)amino]thieno[2,3-b]pyridine-3-carbonyl fluoride

Intermediate 4 (7.80 g, 18.7 mmol) was suspended in dichloromethane (200 mL). DAST (2.80 mL, 20.8 mmol) was added and the mixture was stirred at room temperature for 3 hours. Ice cold water (3 mL) was added and stirring was continued for 5 minutes. Sodium sulfate (~25 g) was then added to absorb the water and dry solvent. After filtration, the filtrate was passed through a 70 g pre-packed silica column and eluted with dichloromethane (1 L). All the eluent was collected and concentrated in vacuo to give the title compound as a pale yellow solid (4.80 g, 61%). $\delta_H$ (DMSO-$d_6$) 10.03 (1H, br s), 8.33 (1H, dd, J 1.4, 4.7 Hz), 8.09 (1H, d, J 8.1 Hz), 7.91 (1H, dd, J 1.8, 9.7 Hz), 7.73 (1H, dd, J 1.0, 8.3 Hz), 7.49-7.42 (2H, m).

Intermediate 6

6-Oxa-3-azabicyclo[3.1.0]hexane-3-carboxylic acid tert-butyl ester

To a solution of tert-butyl 2,5-dihydro-1H-pyrrole-1-carboxylate (10 g, 0.059 mol) in DCM (200 mL) was added MCPBA (14.5 g, 0.065 mol) and the mixture stirred for 18 h. After this time the mixture was washed with water (50 mL) and sodium bicarbonate solution (50 mL), dried (Na$_2$SO$_4$), filtered and the volatiles evaporated in vacuo. The crude product was purified by chromatography (SiO$_2$; 10% ethyl acetate in DCM), yielding the title compound as a colourless oil (6.2 g, 59%). $\delta_H$(DMSO-$d_6$) 3.74 (2H, m), 3.57 (2H, m), 3.25 (2H, m), 1.38 (9H, s).

Intermediate 7

3-Hydroxy-4-(methylamino)pyrrolidine-1-carboxylic acid tert-butyl ester

To a solution of Intermediate 6 (1.0 g, 5.4 mmol) in MeOH (50 mL) was added 33% methylamine in methanol (20 mL, 200 mmol) and the mixture stirred with heating overnight at 80° C. After this time the mixture was evaporated in vacuo to give the title compound as a colourless oil (1.1 g, quant.). $\delta_H$ (DMSO-$d_6$) 4.96 (1H, m), 3.90 (1H, m), 3.33 (2H, m), 3.08 (2H, m), 2.81 (1H, m), 2.25 (3H, s), 1.39 (9H, s).

Intermediate 8

3-[N-(tert-Butoxycarbonyl)-N-methylamino]-4-hydroxypyrrolidine-1-carboxylic acid tert-butyl ester To a solution of Intermediate 7 (450 mg, 2.09 mmol) in 1,4-dioxane (30 mL) was added sodium hydroxide (126 mg, 3.14 mmol) and di-tert-butyl dicarbonate (684 mg, 3.14 mmol) and the mixture stirred for 18 h. After this time the mixture was diluted with ethyl acetate (30 mL), washed with water (25 mL), dried (Na$_2$SO$_4$) and evaporated in vacuo to give title compound as a colourless oil (600 mg, 91%). $\delta_H$ (DMSO-$d_6$) 5.30 (1H, m), 4.26 (2H, m), 3.57 (2H, m), 3.14 (1H, m), 2.97 (1H, m), 2.75 (3H, s), 1.38 (18H, s).

Intermediate 9

3-Methyl-2-oxohexahydropyrrolo[3,4-d]oxazole-5-carboxylic acid tert-butyl ester

To a solution of Intermediate 8 (300 mg, 0.95 mmol) in DCM (5 mL) cooled to −78° C. was added DAST (253 mg, 1.90 mmol) dropwise. After 20 minutes of stirring at −78° C. the mixture was allowed to warm up to room temperature and was stirred for a further 45 minutes. The mixture was diluted with DCM (20 mL) and washed with sat. sodium bicarbonate solution (25 mL), dried (Na$_2$SO$_4$) and evaporated in vacuo to give the title compound as a white solid (300 mg, quant.). $\delta_H$ (DMSO-$d_6$) 5.00 (1H, m), 4.23 (1H, m), 3.66 (2H, m), 3.33 (1H, m) 3.12 (1H, m), 2.75 (3H, s), 1.38 (9H, s). LCMS RT 1.50 minutes, (ES$^+$) 187 (M+H-$^t$BuO).

Intermediate 10

3-Methylhexahydropyrrolo[3,4-d]oxazol-2-one

To a solution of Intermediate 9 (300 mg, 1.24 mmol) was added 4.0M HCl in 1,4-dioxane (10 mL) and the mixture was stirred for 48 h. The solvent was removed in vacuo to afford the title compound as a hydrochloride salt (158 mg, 86%). $\delta_H$ (DMSO-$d_6$) 9.53 (1H, s), 5.02 (1H, d, J 6.4 Hz), 4.28 (1H, m), 3.84 (2H, m), 3.46 (1H, m), 3.21 (1H, m), 2.63 (3H, s).

Intermediate 11

(3S,4S)-3-Azido-4-(trimethylsilanyloxy)pyrrolidine-1-carboxylic acid tert-butyl ester (R,R)—N,N'-Bis(3,5-di-tert-butylsalicylidene)-1,2-cyclohexanediamino-chromium (III) chloride (341 mg, 0.54 mmol) and Intermediate 6 (5.0 g, 27.0 mmol) were treated with trimethylsilyl azide (3.26 g, 28.0 mmol) and stirred together for 4 h at room temperature. The crude product was purified by chromatography (SiO$_2$; 50% hexane in DCM) to obtain the title compound as a straw-coloured oil (5.15 g, 64%). $\delta_H$ (DMSO-$d_6$) 4.11 (1H, m), 3.89 (1H, m), 3.37 (2H, m), 3.04 (1H, m), 2.92 (1H, m), 1.26 (9H, s), 0.00 (9H, s).

Intermediate 12

(3S,4S)-3-Amino-4-hydroxypyrrolidine-1-carboxylic acid tert-butyl ester

To a solution of Intermediate 11 (5.1 g, 17.1 mmol) in MeOH (50 mL) was added TFA (3 drops) and the mixture stirred for 2 h. After this time the mixture was treated with platinum oxide (100 mg, 0.44 mmol) and stirred under a hydrogen atmosphere for 18 h. The mixture was then filtered through celite and the solvent evaporated in vacuo. The crude solid was recrystallised from DCM to afford the title compound as a white solid (2.42 g, 71%). $\delta_H$ (CDCl$_3$) 3.99 (1H, m), 3.70 (2H, m), 3.34 (2H, m), 3.12 (1H, m), 1.48 (9H, s).

Intermediate 13

(3S,4S)-3-(tert-Butoxycarbonylamino)-4-hydroxy-pyrrolidine-1-carboxylic acid tert-butyl ester To a solution of Intermediate 12 (700 mg, 5.0 mmol) in 1,4-dioxane (30 mL) was added sodium hydroxide (300 mg, 7.5 mmol) and di-tert-butyl dicarbonate (1.6 g, 7.5 mmol) and the mixture stirred for 18 h. After this time the reaction mixture was diluted with ethyl acetate (30 mL) and washed with water (25 mL), dried (Na$_2$SO$_4$) and evaporated in vacuo to give the title compound as a colourless oil (1.4 g, 93%). $\delta_H$ (DMSO-d$_6$) 7.02 (1H, s), 5.18 (1H, m), 3.96 (1H, m), 3.57 (1H, m), 3.42 (2H, m), 3.08 (2H, m), 1.40 (18H, s).

Intermediate 14

(3aS,6aR)-2-oxohexahydropyrrolo[3,4-d]oxazole-5-carboxylic acid tert-butyl ester To a solution of Intermediate 13 (750 mg, 2.5 mmol) in DCM (20 mL), cooled to −78° C., was added DAST (665 mg, 5.0 mmol) dropwise. After 45 minutes at −78° C. the mixture was allowed to warm up to room temperature and was stirred for a further 60 minutes. The mixture was diluted with DCM (50 mL) and washed with sat. sodium bicarbonate solution (25 mL), dried (Na$_2$SO$_4$), filtered and evaporated in vacuo to give the title compound as a white waxy solid (543 mg, 95%). $\delta_H$ (DMSO-d$_6$) 7.82 (1H, s), 5.05 (1H, m), 4.25 (1H, m), 3.65 (1H, m), 3.45 (1H, m), 3.29 (1H, m), 3.18 (1H, m), 1.40 (9H, s). LCMS RT 1.30 minutes, (ES$^+$) 251 (M+Na).

Intermediate 15

(3aS,6aR)-Hexahydropyrrolo[3,4-d]oxazol-2-one

Intermediate 14 (530 mg, 2.33 mmol) was treated with 4M HCl in 1,4-dioxane (5 mL) and allowed to stir for 4 h at room temperature. After this time the solvent was removed in vacuo to afford the hydrochloride salt of the title compound as a dark brown solid (370 mg, 99%). $\delta_H$ (DMSO-d$_6$) 9.65 (2H, s), 8.02 (1H, s), 5.22 (1H, m), 4.48 (1H, m), 3.55 (1H, m), 3.30 (1H, m, obscured by water peak), 3.26 (1H, m), 2.91 (1H, m).

In an alternative procedure, the hydrochloride salt of the title compound was prepared as a colourless solid from Intermediate 95 by hydrogenation under the conditions described below for the preparation of Intermediate 80.

Intermediate 16 cis-3,4-Dihydroxypyrrolidine-1-carboxylic acid tert-butyl ester tert-Butyl 2,5-dihydro-1H-pyrrole-1-carboxylate (1.0 g, 5.9 mmol) was dissolved in a mixture of acetone (10 mL), water (25 mL) and tert-butanol (5 mL), treated with N-methylmorpholine-N-oxide (724 mg, 6.2 mmol) followed by osmium tetroxide (4% solution in water) (1.5 mL, 0.06 mmol), and stirred for 18 h at ambient temperature. After this time a slurry, made up of sodium hydrosulfite (1 g), fluorosil (12 g) and water (80 mL), was added to the reaction mixture. After filtration the filtrate was extracted into ethyl acetate (2×50 mL) and the combined organic layers dried (Na$_2$SO$_4$) and evaporated in vacuo to afford the title compound as white solid (580 mg, 47%). $\delta_H$ (CDCl$_3$) 4.18 (2H, m), 3.50 (2H, m), 3.27 (2H, m), 2.50 (2H, m), 1.38 (9H, s).

Intermediate 17

Pyrrolidine-cis-3,4-diol

Intermediate 16 (571 mg, 2.75 mmol) was treated with 4M HCl in 1,4-dioxane (5 mL) and allowed to stir for 3 h at room temperature. After this time the solvent was removed in vacuo to afford the hydrochloride salt of the title compound as an off-white solid (383 mg, 97%). $\delta_H$ (DMSO-d$_6$) 9.30 (2H, m), 5.32 (2H, m), 4.09 (2H, m), 3.21 (2H, m), 2.95 (2H, m).

Intermediate 18

(cis-3,4-Dihydroxypyrrolidin-1-yl)-[2-(2-fluoro-4-iodophenylamino)thieno[2,3-b]pyridin-3-yl]-methanone EDC (487 mg, 2.54 mmol) was added to a solution of Intermediate 17 (363 mg, 2.54 mmol), HOBT (389 mg, 2.54 mmol), DIPEA (0.83 mL, 5.08 mmol) and Intermediate 5 (560 mg, 1.35 mmol) in DMF (50 mL). The reaction mixture was stirred at ambient temperature for 20 h, then poured into ethyl acetate (100 mL). The organic solution was washed with sat. brine (2×50 mL), dried (Na$_2$SO$_4$), filtered and concentrated in vacuo to a brown solid. The crude product was purified by chromatography (SiO$_2$; 5% MeOH in DCM) to give the title compound as a brown powder (265 mg, 39%). $\delta_H$ (DMSO-d$_6$) 9.19 (1H, s), 8.35 (1H, dd, J 1.6, 4.7 Hz), 7.79 (1H, dd, J 1.5, 4.2 Hz), 7.68 (1H, dd, J 1.9, 10.6 Hz), 7.49 (1H, dd, J 1.0, 8.4 Hz), 7.35 (1H, dd, J 4.7, 8.1 Hz), 7.25 (1H, dd, J 8.7, 8.7 Hz), 4.89 (2H, d, J 4.8 Hz), 3.97 (2H, d, J 4.7 Hz), 3.45 (2H, m), 3.18 (2H, m). LCMS RT 2.04 minutes, (ES$^-$) 499 (M−H)$^-$, (ES$^+$) 501 (M+H)$^+$.

Intermediate 19

(3R,4R)-3-Azido-4-(trimethylsilanyloxy)pyrrolidine-1-carboxylic acid tert-butyl ester (S,S)—N,N'-Bis(3,5-di-tert-butylsalicylidene)-1,2-cyclohexanediamino-chromium (III) chloride (341 mg, 0.54 mmol) and Intermediate 6 (5.0 g, 27.0 mmol) were treated with trimethylsilyl azide (3.26 g, 28.0 mmol) and stirred together for 4 h at room temperature. The crude product was purified by chromatography (SiO$_2$; 50% hexane in DCM) to obtain the title compound as a straw-coloured oil (2.5 g, 31%). $\delta_H$ (DMSO-d$_6$) 4.11 (1H, m), 3.89 (1H, m), 3.37 (2H, m), 3.04 (1H, m), 2.92 (1H, m), 1.26 (9H, s), 0.00 (9H, s).

Intermediate 20

(3R,4R)-3-Amino-4-hydroxypyrrolidine-1-carboxylic acid tert-butyl ester

To a solution of Intermediate 19 (2.5 g, 8.4 mmol) in MeOH (50 mL) was added TFA (3 drops) and the mixture stirred for 2 h. After this time the mixture was treated with platinum oxide (100 mg, 0.44 mmol) and stirred under a hydrogen atmosphere for 18 h. The mixture was then filtered through celite and the solvent evaporated in vacuo. The crude solid was recrystallised from DCM to afford the title compound as a white solid (1.5 g, 89%). $\delta_H$ (CDCl$_3$) 3.99 (1H, m), 3.70 (2H, m), 3.34 (2H, m), 3.12 (1H, m), 1.48 (9H, s).

Intermediate 21

(3R,4R)-3-Hydroxy-4-(2,2,2-trifluoroacetylamino) pyrrolidine-1-carboxylic acid tert-butyl ester To a solution of Intermediate 20 (500 mg, 2.5 mmol) in THF (12 mL) cooled to 0° C. was added trifluoroacetic anhydride (0.35 mL, 2.5 mmol) followed by triethylamine (0.2 mL, 3.0 mmol), and the mixture was stirred for 1 h at 0° C. and 18 h at ambient temperature. After this time water (10 mL) was added and the mixture was extracted with 9:1 DCM:2-propanol (3×25 mL). The combined organics were dried (Na$_2$SO$_4$), filtered and the volatiles evaporated in vacuo to afford the title compound as a colourless oil (814 mg, >99%). $\delta_H$ (CDCl$_3$) 4.34-4.27 (1H, m), 4.27-4.18 (1H, m), 3.85 (1H, dd, J 12.1, 6.4 Hz), 3.68-3.58 (1H, m), 3.55-3.27 (2H, m), 1.48 (9H, s).

Intermediate 22

(3aR,6aS)-2-Trifluoromethyl-3a,4,6,6a-tetrahydropyrrolo[3,4-d]oxazole-5-carboxylic acid tert-butyl ester To a solution of Intermediate 21 (814 mg, 2.75 mmol) in DCM (20 mL) was added triethylamine (0.46 mL, 3.3 mmol). After cooling to 0° C. methanesulfonyl chloride (0.24 mL, 3.0 mmol) was added and, after stirring for 5 minutes at 0° C., the mixture was allowed to warm up to room temperature and stirred for a further 2.5 h. DBU was then added and the reaction stirred for 30 minutes before the mixture was evaporated in vacuo. The crude product was purified by column chromatography (3:1 hexane:ethyl acetate) to afford the title compound as a colourless oil (397 mg, 57%). $\delta_H$ (CDCl$_3$) 5.27 (1H, dd, J 7.3, 5.7 Hz), 4.84 (1H, t, J 7.5 Hz), 3.96-4.07 (1H, m), 3.89 (1H, d, J 12.4 Hz), 3.52-3.40 (2H, m), 1.47 (9H, s).

Intermediate 23

(3R,4S)-3-Amino-4-hydroxypyrrolidine-1-carboxylic acid tert-butyl ester

Intermediate 22 (397 mg, 1.42 mmol) was dissolved in MeOH (6 mL) and water (3 mL) and treated with potassium carbonate (1.18 g, 8.5 mmol) and left to stir for 18 h at room temperature. After this time the volatiles were removed by evaporation in vacuo, and the mixture then extracted with 9:1 chloroform:2-propanol solution (5×10 mL). The organic layers were combined, dried (Na$_2$SO$_4$), filtered and evaporated in vacuo before being recrystalised from DCM/hexane to give the title compound as a white powder (205 mg, 72%). $\delta_H$ (DMSO-d$_6$) 4.95 (1H, s), 3.85 (1H, s), 3.37-3.15 (4H, m), 2.86-2.78 (1H, m), 1.49 (2H, s), 1.39 (9H, s).

Intermediate 24

(3R,4S)-3-Aminopyrrolidin-4-ol

Intermediate 23 (100 mg, 0.5 mmol) in methanol (5 mL) was treated with 4M HCl in 1,4-dioxane (5 mL) and allowed to stir for 6 h at room temperature. After this time the solvent was removed in vacuo to afford the hydrochloride salt of the title compound as an off-white solid (87 mg, quant.), which was used in the next reaction without further purification.

Intermediate 25

[(3R,4S)-3-Amino-4-hydroxypyrrolidin-1-yl]-[2-(2-fluoro-4-iodophenylamino)-thieno[2,3-b]pyridin-3-yl]-methanone To a solution of Intermediate 24 (87 mg, 0.5 mmol) and DIPEA (0.26 mL, 1.5 mmol) in DMF (5 mL) was added Intermediate 5 (208 mg, 0.5 mmol) and the mixture stirred for 18 h. After this time the mixture was diluted with ethyl acetate (50 mL) and washed with saturated brine (3×50 mL), then dried (Na$_2$SO$_4$), filtered and concentrated in vacuo. The crude product was purified by chromatography (SiO$_2$; 5% MeOH in DCM) to obtain the title compound as a cream-coloured powder (156 mg, 63%). $\delta_H$ (DMSO-d$_6$) 8.36 (1H, dd, J 1.5, 4.5 Hz), 7.80 (1H, dd, J 1.5, 8.1 Hz), 7.67 (1H, dd, J 10.5, 1.9 Hz), 7.49 (1H, ddd, J 8.5, 1.9, 0.9 Hz), 7.36 (1H, dd, J 4.7, 7.9 Hz), 7.15 (1H, dd, J 8.7, 8.7 Hz), 3.89 (1H, dd, J 2.4, 0.8 Hz), 3.57-3.14 (4H, m), 3.04 (1H, dd, J 10.2, 8.5 Hz). LCMS RT 1.84 minutes, (ES$^-$) 497 (M−H)$^-$, (ES$^+$) 499 (M+H)$^+$.

Intermediate 26

(3S,4S)-3-Benzoylamino-4-hydroxypyrrolidine-1-carboxylic acid tert-butyl ester

Intermediate 12 (2.1 g, 10.4 mmol) was dissolved in DCM (20 mL) and triethylamine (1.26 g, 1.75 mL, 12.5 mmol), cooled to 0° C. and treated with benzoyl chloride (1.6 mL, 11.4 mmol). The reaction was stirred at 0° C. for 30 minutes then allowed to warm to room temperature. After concentration in vacuo the residual oil was chromatographed (SiO$_2$; ethyl acetate) to yield the title compound (2 g). $\delta_H$ (DMSO-d$_6$) 8.45 (1H, d, J 6.6 Hz), 7.82-7.88 (2H, m), 7.42-7.56 (3H, m), 5.32 (1H, d, J 4.0 Hz), 4.16-4.25 (1H, m), 4.10-4.16 (1H, m), 3.54-3.67 (1H, m), 3.50 (1H, dd, J 11.3, 4.9 Hz), 3.29-3.19 (1H, m), 3.18-3.13 (1H, m), 1.42 (9H, s). LCMS RT 1.54 minutes, (ES$^+$) 307 (M+H)$^+$.

Intermediate 27

(3aS,6aR)-2-Phenyl-3a,4,6,6a-tetrahydropyrrolo[3,4-d]oxazole-5-carboxylic acid tert-butyl ester Intermediate 26 (2.0 g, 6.5 mmol) was dissolved in DCM (20 mL), cooled to −78° C., and treated with DAST (1.16 g, 0.94 mL, 7.2 mmol). The reaction mixture was allowed to warm to room temperature, then stirred overnight. After washing with water then sodium carbonate solution the organic phase was dried (sodium sulphate) and concentrated in vacuo. Chromatography (SiO$_2$; ethyl acetate) yielded the title compound (1.3 g). $\delta_H$ (DMSO-d$_6$) 7.86 (2H, m), 7.60-7.52 (1H, m), 7.52-7.44 (2H, m), 5.28-5.20 (1H, m), 4.84-4.76 (1H, m), 3.80-3.71 (1H, m), 3.65-3.57 (1H, m), 3.48-3.34 (2H, m), 1.36-1.30 (9H, m). LCMS RT 2.34 minutes, (ES$^+$) 289 (M+H)$^+$.

Intermediate 28

(3aS,6aR)-2-Phenyl-4,5,6,6a-tetrahydro-3aH-pyrrolo[3,4-d]oxazole

Intermediate 27 (0.5 g, 1.7 mmol) was dissolved in aqueous 12M HCl and stirred at room temperature for 2 h. The reaction was evaporated to dryness and azeotroped with heptane, to remove residual water, yielding the title compound as the hydrochloride salt (295 mg). δ$_H$ (DMSO-d$_6$) 10.10 (2H, br s), 7.92 (2H, dd, J 7.6, 2.0 Hz), 7.73-7.48 (3H, m), 5.50 (1H, dd, J 7.9, 5.2 Hz), 5.05 (1H, t, J 7.0 Hz), 3.63 (1H, dd, J 13.3, 4.7 Hz), 3.52-3.36 (3H, m). LCMS RT 1.26 minutes, (ES$^+$) 189 (M+H)$^+$.

Intermediate 29 tert-Butyl[cis-(3,4)-4-(hydroxymethyl)pyrrolidin-3-yl]carbamate

A solution of benzyl cis-(3,4)-3-(tert-butoxycarbonylamino)-4-(hydroxymethyl)-pyrrolidine-1-carboxylate (prepared by the method of J. Ji et al., *J. Med. Chem.*, 2007, 50, 5493-5508) (1.06 g, 3.0 mmol) and Pd/C (10 wt %, 100 mg) in absolute EtOH (25 mL) was stirred under H$_2$ at room temperature for 20 h. The reaction mixture was filtered through celite and concentrated in vacuo to yield the title compound as a white solid (646 mg, quant.). δ$_H$ (CDCl$_3$) 5.15 (1H, d, J 8.1 Hz), 4.24-4.32 (1H, m), 3.66 (1H, dd, J 11.7, 4.3 Hz), 3.54-3.61 (1H, m), 3.28 (1H, dd, J 10.9, 5.8 Hz), 3.11 (1H, dd, J 10.4, 8.5 Hz), 2.90 (1H, dd, J 10.9, 2.3 Hz), 2.65 (1H, m), 2.39-2.50 (1H, m), 1.48 (9H, s).

Intermediate 30 tert-Butyl[cis-(3,4)-1-({2-[(2-fluoro-4-iodophenyl)amino]thieno[2,3-b]pyridin-3-yl}carbonyl)-4-(hydroxymethyl)pyrrolidin-3-yl]carbamate A mixture of Intermediate 29 (646 mg, 3.0 mmol) and DIPEA (0.78 mL, 4.5 mmol) in DMF (10 mL) was treated with a solution of Intermediate 5 (1.24 g, 3.0 mmol) in DMF (10 mL) and stirred at room temperature for 3 h. The DMF was removed in vacuo, the residue was dissolved in DCM and washed with brine, and the organic phase was dried over sodium sulfate and concentrated in vacuo. Recrystallisation from ethyl acetate/hexane yielded the title compound as an off-white powder (1.47 g, 80%). δ$_H$ (DMSO-d$_6$) 9.14 (1H, s), 8.35 (1H, dd, J 4.7, 1.5 Hz), 7.86-7.88 (1H, m), 7.70 (1H, dd, J 10.5, 1.9 Hz), 7.50-7.53 (1H, m), 7.37 (1H, dd, J 8.1, 4.7 Hz), 7.19 (1H, dd, J 8.9, 8.9 Hz), 7.16-7.19 (1H, m), 4.51 (1H, s), 4.07 (1H, s), 3.42-3.61 (3H, m), 3.25-3.36 (3H, m), 2.27-2.40 (1H, m), 1.36 (9H, s). LCMS RT 2.73 minutes, (ES$^+$) 613.0 (M+H)$^+$.

Intermediate 31

[cis-(3,4)-4-Amino-1-({2-[2-fluoro-4-iodophenyl)amino]thieno[2,3-b]pyridin-3-yl}carbonyl)pyrrolidin-3-yl]methanol Intermediate 30 (1.45 g, 2.4 mmol) in MeOH (20 mL) was treated with 4M HCl/1,4-dioxane (10 mL) and stirred at room temperature for 1.5 h. The solvents were removed in vacuo, and the residues were dissolved in MeOH, basified to pH 10 with 28% aqueous NH$_3$ and concentrated in vacuo onto SiO$_2$. Chromatography (SiO$_2$; 93:6.3:0.7 DCM/MeOH/28% aqueous NH$_3$) yielded the title compound, which was freeze-dried from acetonitrile/water to a yellow powder (1.12 g, 92%). δ$_H$ (DMSO-d$_6$) 8.35 (1H, dd, J 4.7, 1.5 Hz), 7.82 (1H, dd, J 8.1, 1.5 Hz), 7.67 (1H, dd, J 10.5, 1.9 Hz), 7.49 (1H, ddd, J 8.3, 1.9, 0.9 Hz), 7.36 (1H, dd, J 7.9, 4.7 Hz), 7.15 (1H, dd, J 8.7, 8.7 Hz), 3.13-3.58 (7H, m), 2.08-2.22 (1H, m). LCMS RT 1.64 minutes, (ES$^+$) 513.0 (M+H)$^+$.

Intermediate 32

3-[2-(2-Fluoro-4-iodophenylamino)thieno[2,3-b]pyridine-3-carbonyl]-3,6-diazabicyclo[3.2.01]heptane-6-carboxylic acid tert-butyl ester A mixture of cis-(1,5)-tert-butyl 3,6-diazabicyclo[3.2.0]heptane-6-carboxylate (prepared by the method of J. Ji et al., *J. Med. Chem.*, 2007, 50, 5493-5508) (69 mg, 0.35 mmol) and DIPEA (0.09 mL, 0.52 mmol) in DMF (5 mL) was treated with a solution of Intermediate 5 (145 mg, 0.35 mmol) and stirred at room temperature for 3 days. The reaction mixture was diluted with ethyl acetate and washed with brine, and the organic phase was dried over sodium sulfate and concentrated in vacuo to yield the title compound as a yellow oil (199 mg, 96%). δ$_H$ (CDCl$_3$) 9.22 (1H, s), 8.27 (1H, dd, J 4.7, 1.5 Hz), 7.72 (1H, m), 7.39-7.44 (2H, m), 7.31 (1H, dd, J 8.3, 8.3 Hz), 7.18 (1H, m), 4.62 (1H, s), 4.00-4.11 (3H, m), 3.57 (1H, m), 3.22-3.28 (1H, m), 2.96-3.10 (2H, m), 1.29 (9H, s). LCMS RT 1.48 minutes, (ES$^+$) 595.0 (M+H)$^+$.

Intermediate 33

Methyl trans-(3,4)-4-aminopyrrolidine-3-carboxylate trans-(3,4)-4-Aminopyrrolidine-1,3-dicarboxylic acid 1-tert-butyl ester 3-ethyl ester (995 mg, 3.4 mmol) in MeOH (10 mL) was treated with 4M HCl/1,4-dioxane and stirred at room temperature for 3 days. The reaction mixture was evaporated in vacuo to yield the dihydrochloride salt of the title compound as an off-white solid (770 mg, 91%), which was used in the next reaction without further purification.

Intermediate 34

Methyl trans-(3,4)-4-amino-1-({2-[(2-fluoro-4-iodophenyl)amino]thieno[2,3-b]pyridin-3-yl}carbonyl)pyrrolidine-3-carboxylate A mixture of Intermediate 33 (770 mg, 3.0 mmol) and DIPEA (1.1 mL, 6.0 mmol) in DMF (10 mL) was treated with Intermediate 5 (630 mg, 1.5 mmol) and stirred at room temperature for 20 h. The reaction mixture was diluted with ethyl acetate and extracted with water, and the aqueous phase was basified to pH 11 with sodium carbonate, then extracted with a solution of 9:1 DCM/MeOH. The organic phase was dried over sodium sulfate and concentrated in vacuo. Chromatography (SiO$_2$; 95:4.5:0.5 DCM/MeOH/28% aqueous NH$_3$) yielded the title compound, which was freeze-dried from acetonitrile/water to a cream-coloured powder (220 mg, 24%). δ$_H$ (DMSO-d$_6$) 8.36 (1H, dd, J 4.7, 1.5 Hz), 7.82 (1H, dd, J 8.1, 1.5 Hz), 7.68 (1H, dd, J 10.4, 1.9 Hz), 7.50 (1H, ddd, J 8.5, 1.9, 0.9 Hz), 7.37 (1H, dd, J 8.1, 4.7 Hz), 7.15 (1H, dd, J 8.7, 8.7 Hz), 3.69 (1H, dd, J 11.5, 8.5 Hz), 3.62 (3H, s), 3.44-3.59 (3H, m), 3.07 (1H, dd, J 10.4, 6.6 Hz), 2.79 (1H, q, J 7.7 Hz). LCMS RT 1.74 minutes, (ES$^+$) 541.1 (M+H)$^+$.

Intermediate 35

[trans-(3,4)-4-Amino-1-({2-[2-fluoro-4-iodophenyl)amino]thieno[2,3-b]pyridin-3-yl}carbonyl)pyrrolidin-3-yl]methanol A mixture of Intermediate 34 (100 mg, 0.19 mmol) and lithium borohydride (8 mg, 0.37 mmol) in THF (5 mL) was heated to 80° C. and stirred for 3 h, then cooled to room temperature and concentrated in vacuo. The title compound formed as a complex with borane; this was broken up by dissolving the product residues in methanol and heating to reflux with stirring for 4 h. The resulting solution was cooled to room temperature and concentrated in vacuo. Chromatography (SiO$_2$; 93:6.3:0.7 DCM/MeOH/28% aqueous NH$_3$) yielded the title compound, which was freeze-dried from acetonitrile/water to a white powder (63 mg, 66%). $\delta_H$ (DMSO-d$_6$) 8.35 (1H, dd, J 4.7, 1.5 Hz), 7.80 (1H, dd, J 8.1, 1.5 Hz), 7.67 (1H, dd, J 10.4, 1.9 Hz), 7.49 (1H, ddd, J 8.3, 1.9, 0.9 Hz), 7.36 (1H, dd, J 8.1, 4.7 Hz), 7.13 (1H, dd, J 8.7, 8.7 Hz), 4.58 (1H, broad s), 3.43-3.57 (2H, m), 3.46 (1H, dd, J 10.9, 5.5 Hz), 3.31 (1H, dd, J 10.7, 6.6 Hz), 3.15 (1H, dd, J 11.7, 8.5 Hz), 2.97-3.07 (2H, m), 1.84-1.94 (1H, m). LCMS RT 1.51 minutes, (ES$^+$) 513.0 (M+H)$^+$.

Intermediate 36 cis-(3,6)-Hexahydropyrrolo[3,4-b]pyrrole-1,5-dicarboxylic acid 1-benzyl ester 5-tert-butyl ester A mixture of cis-(3,6)-tert-butyl hexahydropyrrolo[3,4-b]pyrrole-5(1H)-carboxylate (1 g, 4.7 mmol) and triethylamine (0.72 mL, 5.2 mmol) in DCM (20 mL) was treated with benzyl chloroformate (0.73 mL, 5.2 mmol) and stirred for 20 h at room temperature. The reaction mixture was washed with brine, dried over sodium sulfate and evaporated in vacuo. Chromatography (SiO$_2$; 3:1 hexane/ethyl acetate) yielded the title compound as a colourless oil (1.59 g, 97%). $\delta_H$ (CDCl$_3$) 7.33-7.37 (5H, m), 5.15-5.16 (2H, m), 4.32 (1H, m), 3.51-3.58 (5H, m), 3.24 (1H, m), 2.91 (1H, m), 1.97-2.08 (1H, m), 1.81 (1H, m), 1.47 (9H, s).

Intermediate 37 cis-(3,6)-Hexahydropyrrolo[3,4-b]pyrrole-1-carboxylic acid benzyl ester

A solution of Intermediate 36 (1.59 g, 0.46 mmol) in DCM (15 mL) was treated with trifluoroacetic acid (5 mL) and stirred at room temperature for 1.5 h. The solvents were removed in vacuo and the residues were dissolved in MeOH, basified to pH 10 with 28% aqueous NH$_3$, and concentrated in vacuo onto SiO$_2$. Chromatography (SiO$_2$; 90:9:1 DCM/MeOH/28% aqueous NH$_3$) yielded the title compound as a colourless oil (1.04 g, 92%). $\delta_H$ (CDCl$_3$) 7.30-7.38 (5H, m), 5.18 (1H, d, J 12.4 Hz), 5.12 (1H, d, J 12.4 Hz), 4.27 (1H, m), 3.63 (1H, m), 3.41-3.50 (1H, m), 3.00-3.21 (3H, m), 2.74-2.85 (2H, m), 2.02-2.05 (1H, m), 1.66-1.76 (1H, m).

Intermediate 38 cis-(3,6)-5-[2-(2-Fluoro-4-iodophenylamino)thieno[2,3-b]pyridine-3-carbonyl]-hexahydropyrrolo[3,4-b]pyrrole-1-carboxylic acid benzyl ester A mixture of Intermediate 37 (118 mg, 0.48 mmol) and DIPEA (0.13 mL, 0.72 mmol) in DMF (5 mL) was treated with Intermediate 5 (200 mg, 0.48 mmol) and stirred at room temperature for 20 h. The reaction mixture was diluted with ethyl acetate and washed with brine, dried over sodium sulfate and concentrated in vacuo, to yield the title compound as a viscous yellow oil (301 mg, 98%). $\delta_H$ (DMSO-d$_6$) 8.94-8.98 (1H, m), 8.27 (1H, m), 7.53 (1H, dd, J 8.1, 1.5 Hz), 7.38-7.41 (2H, m), 7.17-7.30 (5H, m), 7.08 (1H, m), 4.92-5.05 (2H, m), 4.24 (1H, m), 3.46-3.79 (6H, m), 2.96-2.86 (1H, m), 1.75 (1H, m), 1.64 (1H, m). LCMS RT 1.51 minutes, (ES$^+$) 643.0 (M+H)$^+$.

Intermediate 39

(3S,4S)-3-Azido-4-hydroxypyrrolidine-1-carboxylic acid tert-butyl ester

To a solution of Intermediate 11 (6.0 g, 19.97 mmol) in MeOH (60 mL) was added TFA (1 drop) and the mixture stirred for 30 min. After this time the mixture was neutralised with NH$_4$OH. The solvent was then removed in vacuo, and the residue was diluted with EtOAc (60 mL), washed with saturated brine (3×60 mL), dried (Na$_2$SO$_4$) and concentrated in vacuo to give title compound as a brown oil (4.52 g, 99%). $\delta_H$ (DMSO-d$_6$) 5.54 (1H, d, J 4.0 Hz), 4.03-4.11 (1H, m), 3.94-4.01 (1H, m), 3.45-3.57 (1H, m), 3.34-3.45 (1H, m), 3.23 (1H, dd, J 2.6, 11.9 Hz), 3.12 (1H, dd, J 2.1, 11.5 Hz), 1.40 (9H, s).

Intermediate 40

(3S,4S)-3-Azido-4-(methanesulfonyloxy)pyrrolidine-1-carboxylic acid tert-butyl ester To a solution of Intermediate 39 (3.34 g, 14.63 mmol) in DCM (80 mL) cooled to 0° C. was added DIPEA (3.45 mL, 19.75 mmol), followed by methanesulfonyl chloride (1.47 mL, 19.01 mmol). The mixture was allowed to warm up to room temperature and stirred for a further 6 h. After that time the mixture was washed with saturated brine (2×100 mL), dried (Na$_2$SO$_4$), and concentrated in vacuo. The crude product was purified by chromatography (SiO$_2$; 10-20% EtOAc/hexane) to obtain the title compound as a pale yellow oil (3.54 g, 79%). $\delta_H$ (CDCl$_3$) 4.77-4.82 (1H, m), 4.02-4.15 (1H, m), 3.28-3.63 (4H, m), 2.92 (3H, s), 1.30 (9H, s).

Intermediate 41 cis-(3,4)-3,4-Diazidopyrrolidine-1-carboxylic acid tert-butyl ester

To a solution of Intermediate 40 (2.08 g, 6.79 mmol) in DMF (40 mL) was added sodium azide (1.32 g, 20.37 mmol), and the mixture stirred at 80° C. for 20 h. After this time the reaction mixture was diluted with Et$_2$O (50 mL) and washed with saturated brine (4×50 mL), dried (Na$_2$SO$_4$), and concentrated in vacuo. The crude product was purified by chromatography (SiO$_2$; 10-30% EtOAc in hexane) to obtain the title compound as a pale yellow oil (1.05 g, 61%). $\delta_H$ (CDCl$_3$) 4.04-4.13 (2H, m), 3.58-3.68 (2H, m), 3.35-3.53 (2H, m), 1.46 (9H, s).

Intermediate 42 cis-(3,4)-3,4-Diaminopyrrolidine-1-carboxylic acid tert-butyl ester

To a solution of Intermediate 41 (138 mg, 0.54 mmol) was added 20% palladium hydroxide on carbon (15.3 mg, 0.11 mmol) and stirred under a hydrogen atmosphere for 18 h. The mixture was then filtered through celite, and washed with MeOH and the solvent evaporated in vacuo to obtain the title compound as a colourless oil (93.4 mg, 85%). $\delta_H$ (CDCl$_3$)

3.52-3.78 (2H, m), 3.38-3.52 (2H, m), 3.14-3.37 (2H, m), 1.64-1.99 (4H, m), 1.48 (9H, s).

Intermediate 43 cis-(3,6)-2-Methyl-3a,4,6,6a-tetrahydro-1H-pyrrolo [3,4-d]imidazole-5-carboxylic acid tert-butyl ester To a solution of Intermediate 42 (155 mg, 0.77 mmol) in EtOH (5 mL) was added ethyl acetimidate hydrochloride (124 mg, 1.00 mmol) and the mixture stirred at 80° C. for 2.5 h. After this time the mixture was evaporated in vacuo to give the title compound as a brown oil (173 mg, quant.). $\delta_H$ (DMSO-d$_6$) 4.62-4.74 (2H, m), 3.60 (2H, d, J 12.8 Hz), 3.25-3.36 (2H, m), 2.14 (3H, s), 1.37 (9H, s).

Intermediate 44 cis-(3,6)-2-Methyl-1,3a,4,5,6,6a-hexahydropyrrolo [3,4-d]imidazole

To a solution of Intermediate 43 (170 mg, 0.75 mmol) in MeOH (4 mL) was added 4M HCl in 1,4-dioxane (4 mL) and the mixture was stirred for 2 h. After this time the solvent was removed in vacuo and azeotroped with toluene to afford the hydrochloride salt of the title compound as a brown oil (95 mg, quant.). $\delta_H$ (DMSO-d$_6$) 4.88-4.93 (2H, m), 3.44-3.51 (2H, m), 3.27-3.55 (2H, m), 2.12 (3H, s).

Intermediate 45 cis-(3,6)-2-Oxohexahydropyrrolo[3,4-d]imidazole-5-carboxylic acid tert-butyl ester To a solution of Intermediate 42 (104 mg, 0.52 mmol) in DMF (3 mL) was added CDI (84 mg, 0.52 mmol) and the mixture stirred for 56 h. After this time the solvent was removed in vacuo. The residue was diluted with EtOAc (15 mL), extracted with water (3×15 mL), and then the aqueous was extracted with 10% MeOH/DCM (3×80 mL). The organics were dried (Na$_2$SO$_4$) and concentrated in vacuo to afford the title compound as a yellow/gold foam (82 mg, 60%), which was used in the next reaction without further purification.

Intermediate 46 cis-(3,6)-Hexahydropyrrolo[3,4-d]imidazol-2-one

To a solution of Intermediate 45 (82 mg, 0.36 mmol) in MeOH (10 mL) was added 4M HCl in 1,4-dioxane (10 mL) and the mixture was stirred for 1.5 h. After this time the solvent was removed in vacuo and azeotroped with toluene to afford the hydrochloride salt of the title compound as a brown oil (46 mg, quant.), which was used in the next reaction without further purification.

Intermediate 47

(3S,4S)-3-Hydroxy-4-[3-(9H-fluoren-9-ylmethoxy-carbonyl)thioureido]pyrrolidine-1-carboxylic acid tert-butyl ester To a solution of Intermediate 12 (550 mg, 2.26 mmol) in DCM (20 mL) was added 9H-fluoren-9-ylmethoxycarbonyl isothiocyanate (699 mg, 2.49 mmol) and the mixture was stirred at room temperature for three hours. After this time the solvent was removed in vacuo to yield the title compound as a yellow solid (1.2 g, quant.). $\delta_H$ (DMSO-d$_6$) 11.51 (1H, s), 9.85 (1H, m), 7.90 (2H, m), 7.82 (2H, m), 7.46 (2H, m), 7.36 (2H, m), 5.51 (1H, m), 4.48 (1H, m), 4.35 (2H, m), 4.27 (2H, m), 3.66 (1H, m), 3.39 (1H, m), 3.24 (2H, m), 1.39 (9H, s). LCMS RT 2.99 minutes, (ES$^+$) 485 (M+H).

Intermediate 48

(3aS,6aR)-2-(9H-Fluoren-9-ylmethoxycarbony-lamino)-3a,4,6,6a-tetrahydropyrrolo[3,4-d]thiazole-5-carboxylic acid tert-butyl ester To a solution of Intermediate 47 (700 mg, 1.45 mmol) in DCM (20 mL), cooled in an acetone/cardice bath, was added DAST (291 mg, 159 mmol) and stirred for 30 minutes before being allowed to warm up to room temperature. After 18 hours the reaction mixture was diluted with DCM (50 mL) and washed with NaHCO$_3$ solution (50 mL). After drying (Na$_2$SO$_4$) the organics were evaporated in vacuo to afford the title compound as an orange-coloured solid (605 mg, 88%). $\delta_H$ (DMSO-d$_6$) 8.88 (2H, m), 7.67 (2H, m), 7.39 (2H, m), 7.36 (2H, m), 4.52 (1H, m), 4.36-4.15 (4H, m), 3.71 (1H, m), 3.57-3.37 (3H, m), 1.39 (9H, s). LCMS RT 3.03 minutes, (ES$^+$) 466 (M+H).

Intermediate 49

(3aS,6aR)-(4,5,6,6a-Tetrahydro-3aH-pyrrolo[3,4-d] thiazol-2-yl)carbamic acid 9H-fluoren-9-ylmethyl ester Intermediate 48 (390 mg, 0.839 mmol) was treated with a 1:1 mixture of TFA in DCM (25 mL) and stirred for 2 hours. The reaction mixture was poured onto sodium bicarbonate solution (50 mL) before extracting with DCM (2×50 mL). The organics were combined, dried (Na$_2$SO$_4$) and evaporated to afford the title compound (155 mg, 50%) as a brown gum. $\delta_H$ (DMSO-d$_6$) 7.90-7.60 (4H, m), 7.49-7.25 (4H, m), 6.13 (2H, m), 4.72 (1H, m), 4.30 (1H, m), 4.04 (2H, m), 3.07 (2H, m). LCMS RT 2.14 minutes, (ES$^+$) 366 (M+H).

Intermediate 50

(3S,4S)-3-(3-Cyclopropylthioureido)-4-hydroxypyrrolidine-1-carboxylic acid tert-butyl ester To a solution of Intermediate 12 (500 mg, 2.5 mmol) in DCM (50 mL) was added cyclopropyl isothiocyanate (267 mg, 2.7 mmol) and the mixture was stirred at room temperature for three hours. After this time the solvent was removed in vacuo to yield the title compound as a yellow solid (748 mg, quant.). $\delta_H$ (DMSO-d$_6$) 7.80 (1H, s), 7.35 (1H, d, J 7.6 Hz), 5.29 (1H, d, J 4.2 Hz), 4.42 (1H, m), 4.12 (1H, m), 3.57 (1H, m), 3.43 (1H, m), 3.13 (2H, m), 2.73 (1H, m), 1.40 (9H, s), 0.68 (2H, m), 0.46 (2H, m). LCMS RT 1.59 minutes, (ES$^+$) 302 (M+H).

Intermediate 51

(3aS,6aR)-2-Cyclopropylamino-3a,4,6,6a-tetrahydropyrrolo[3,4-d]thiazole-5-carboxylic acid tert-butyl ester To a solution of Intermediate 50 (745 mg, 2.5 mmol) in DCM (20 mL), cooled in an acetone/cardice bath, was added DAST (333 mg, 2.5 mmol) and stirred for 30 minutes before being allowed to warm up to room temperature. After 18 hours the reaction mixture was diluted with DCM (50 mL) and washed with sodium bicarbonate solution (50 mL). After drying ($Na_2SO_4$) the organics were evaporated in vacuo to give a brown gum and purified by chromatography ($SiO_2$; 5% MeOH in DCM) to afford the title compound as a brown oil (320 mg, 45%). $\delta_H$ (DMSO-$d_6$) 6.89 (1H, s), 4.47 (1H, m), 3.98 (1H, m), 3.53 (1H, m), 3.32 (2H, m), 3.00 (1H, m), 2.31 (1H, m), 1.20 (9H, s), 0.38 (2H, m), 0.21 (2H, m). LCMS RT 1.81 minutes, (ES$^+$) 284 (M+H).

Intermediate 52

N-(Cyclopropyl)-N-[3aS,6aR)-4,5,6,6a-tetrahydro-3aH-pyrrolo[3,4-d]thiazol-2-yl]amine Intermediate 51 (310 mg, 1.10 mmol) was treated with a 1:1 mixture of TFA in DCM (25 mL) and stirred for 3 hours. The reaction mixture was poured onto sodium bicarbonate solution (50 mL) before extracting with DCM (2×50 mL). The organics were combined, dried ($Na_2SO_4$) and evaporated to afford the title compound as a white solid (75 mg, 37%). $\delta_H$ (CDCl$_3$) 4.91 (1H, m), 4.87 (1H, m), 4.11 (1H, m), 3.19-2.01 (3H, m), 2.57 (1H, m), 1.88 (1H, m), 0.64 (2H, m), 0.51 (2H, m). LCMS RT 0.93 minutes, (ES$^+$) 184 (M+H).

Intermediate 53

(3S,4S)-3-Hydroxy-4-ureidopyrrolidine-1-carboxylic acid tert-butyl ester

To a solution of Intermediate 12 (300 mg, 1.49 mmol) in DCM (50 mL) was added trimethylsilyl isocyanate (189 mg, 1.64 mmol) and the mixture was stirred at room temperature for 18 hours. After this time hexane (5 mL) was added to the reaction mixture and a pale precipitate formed. This was filtered and taken on to the next step as crude product (255 mg, 75%).

Intermediate 54

(3aS,6aR)-2-Amino-3a,4,6,6a-tetrahydropyrrolo[3,4-d]oxazole-5-carboxylic acid tert-butyl ester To a solution of Intermediate 53 (250 mg, 1.02 mol) in DCM (20 mL), cooled in an acetone/cardice bath, was added DAST (177 mg, 1.09 mmol) and stirred for 30 minutes before being allowed to warm up to room temperature. After 2 hours at r.t. the reaction mixture was diluted with DCM (50 mL) and washed with NaHCO$_3$ solution (50 mL). After drying ($Na_2SO_4$) the organics were evaporated in vacuo to give a residue which was purified by chromatography ($SiO_2$; 15% MeOH, DCM) to afford the title compound as a white powder (200 mg, 87%). $\delta_H$ (DMSO-$d_6$) 5.10 (1H, m), 4.45 (1H, m), 3.67 (1H, m), 3.48-3.18 (5H, m). LCMS RT 1.26 minutes, (ES$^+$) 228 (M+H).

Intermediate 55

(3aS,6aR)-(4,5,6,6a-Tetrahydro-3aH-pyrrolo[3,4-d]oxazol-2-yl)amine

Intermediate 54 (250 mg, 1.11 mmol) was treated with 4M HCl in 1,4-dioxane (5 mL) and allowed to stir for 3 hours at room temperature. After this time a precipitate had formed which was filtered off to afford the dihydrochloride salt of the title compound as an off-white solid (222 mg, quant.). $\delta_H$ (DMSO-$d_6$) 10.14 (3H, m), 9.33 (2H, m), 5.67 (1H, m), 4.83 (1H, m), 3.51-3.20 (4H, m).

Intermediate 56

(3aS,6aR)-2-Thioxohexahydropyrrolo[3,4-d]oxazole-5-carboxylic acid tert-butyl ester To a solution of Intermediate 23 (200 mg, 1.0 mmol) in DMF (5 mL) was added 1,1'-thiocarbonyldiimidazole (178 mg, 1.1 mmol) and the reaction stirred for 18 hours. Brine was poured onto the reaction mixture and a pale yellow precipitate formed. This was filtered off to afford the title compound (210 mg, 85%). $\delta_H$ (DMSO-$d_6$) 10.14 (1H, m), 5.43 (1H, m), 4.57 (1H, m), 3.78 (1H, m), 3.58 (1H, m), 3.40 (1H, m), 3.22 (1H, m), 1.46 (9H, s). LCMS RT 1.55 minutes, (ES) 242 (M–H).

Intermediate 57

(3aS,6aR)-Hexahydropyrrolo[3,4-d]oxazole-2-thione

Intermediate 56 (200 mg, 0.82 mmol) was treated with 4M HCl in 1,4-dioxane (5 mL) and allowed to stir for 3 h at room temperature. After this time a precipitate had formed which was filtered off to afford the hydrochloride salt of the title compound as an off-white solid (110 mg, 75%). $\delta_H$ (DMSO-$d_6$) 10.27 (1H, s), 10.13 (1H, m), 9.54 (1H, m), 5.56 (1H, m), 4.75 (1H, m), 3.61 (2H, m), 3.23 (2H, m).

Intermediate 58 cis-(4,7)-6-[2-(2-Fluoro-4-iodophenylamino)thieno[2,3-b]pyridine-3-carbonyl]-octahydropyrrolo[3,4-b]pyridine-1-carboxylic acid tert-butyl ester A mixture of cis-(4,7)-1-(tert-butoxycarbonyl)octahydropyrrolo[3,4-b]pyridine (54 mg, 0.24 mmol) and DIPEA (0.06 mL, 0.36 mmol) in DMF (2 mL) was treated with Intermediate 5 (100 mg, 0.24 mmol) and stirred at r.t. for 4.5 h. The reaction mixture was diluted with ethyl acetate and washed with brine, dried over sodium sulfate and concentrated in vacuo. Chromatography ($SiO_2$; 5:2 isohexane/ethyl acetate) yielded the title compound (133 mg, 89%) as a viscous yellow oil. $\delta_H$ (DMSO-$d_6$) 9.00 (1H, s), 8.37 (1H, dd, J 4.7, 1.5 Hz), 7.65 (1H, dd, J 8.1, 1.5 Hz), 7.51-7.47 (2H, m), 7.39 (1H, dd, J 8.7, 8.7 Hz), 7.29 (1H, dd, J 8.1, 4.7 Hz), 4.78-4.76 (1H, m), 4.03-3.98 (1H, m), 3.74 (1H, dd, J 11.7, 5.5 Hz), 3.57-3.54 (2H, m), 3.35-3.32 (1H, m), 2.78-2.70 (1H, m), 2.22-2.17 (1H, m), 1.75-1.66 (3H, m), 1.31 (1H, m), 1.45 (9H, s). LCMS RT 1.60 minutes, (ES$^+$) 623.2 (M+H)$^+$.

Intermediate 59 cis-(3,4)-3-(tert-Butoxycarbonylamino)-4-(cyanomethyl)pyrrolidine-1-carboxylic acid benzyl ester A mixture of cis-(3,4)-3-(tert-butoxycarbonylamino)-4-(methanesulfonyloxy-methyl)pyrrolidine-1-carboxylic acid benzyl ester (prepared by the method of J. Ji et al., *J. Med. Chem.*, 2007, 50, 5493-5508) (1.92 g, 4.48 mmol) and potassium cyanide (320 mg, 4.93 mmol) in DMF (25 mL) was heated to 80° C. and stirred for 20 h, then concentrated in vacuo. The residue was diluted with ethyl acetate and washed with brine, dried over sodium sulfate and concentrated in vacuo. Chromatography ($SiO_2$; 5:2 isohexane/ethyl acetate) yielded the title compound (324 mg, 20%) as a white crystalline solid. $\delta_H$ (CDCl$_3$) 7.32 (5H, m), 5.11-5.09 (3H, m), 4.28 (1H, m), 3.74-3.70 (1H, m), 3.64 (1H, dd, J 11.9, 6.2 Hz), 3.42-3.35 (1H, m), 3.27 (1H, dd, J 11.1, 8.7 Hz), 2.59-2.52 (2H, m), 2.38-2.30 (1H, m), 1.43 (9H, s).

Intermediate 60 cis-(3,6)-2-(Oxo)hexahydropyrrolo[3,4-b]pyrrole-5-carboxylic acid benzyl ester

4M HCl in 1,4-dioxane (5 mL) was added to a solution of Intermediate 59 (324 mg, 0.9 mmol) in MeOH (10 mL) and the reaction heated to reflux and stirred for 7 h, then concentrated in vacuo. The residue was dissolved in MeOH, basified with 28% aqueous NH$_3$, and evaporated onto SiO$_2$ in vacuo. Chromatography (SiO$_2$; 95:4.5:0.5 DCM/MeOH/28% aqueous NH$_3$) yielded the title compound (89 mg, 26%) as a colourless oil. $\delta_H$ (CDCl$_3$) 7.39-7.32 (5H, m), 6.46-6.35 (1H, m), 5.14 (2H, s), 4.27-4.22 (1H, m), 3.84-3.77 (1H, m), 3.64 (1H, m), 3.55 (1H, dd, J 12.2, 5.3 Hz), 3.39-3.32 (1H, m), 3.10-2.99 (1H, m), 2.62 (1H, dd, J 17.1, 8.3 Hz), 2.27-2.21 (1H, m).

Intermediate 61 cis-(3,6)-Hexahydropyrrolo[3,4-b]pyrrol-2(1H)-one

A mixture of Intermediate 60 (89 mg, 0.34 mmol) and 10% Pd/C in ethanol (5 mL) was stirred under hydrogen for 3 days. The reaction mixture was filtered through celite and concentrated in vacuo to yield the title compound (46 mg, >99%) as white needles. $\delta_H$ (CDCl$_3$) 6.00 (1H, br s), 4.09 (1H, dd, J 6.0, 6.0 Hz), 2.96-2.73 (4H, m), 2.72 (1H, dd, J 12.4, 4.9 Hz), 2.59 (1H, dd, J 17.7, 10.0 Hz), 2.06 (1H, dd, J 17.9, 3.0 Hz).

Intermediate 62

2-Methyl-4,6-dihydro-1H-pyrrolo[3,4-d]imidazole-5-carboxylic acid tert-butyl ester To a solution of oxalyl chloride (66.5 µL, 0.79 mmol) in DCM (7 mL), cooled to −78° C., was added dimethylsulfoxide (112 µL, 1.57 mmol) and the mixture was stirred for 10 minutes. After this time Intermediate 43 (177 mg, 0.79 mmol) in DCM (10 mL) was added and the mixture was stirred for a further 30 minutes. Triethylamine (50 mL) was then added and the mixture allowed to warm up to r.t. over 30 minutes. After this time the mixture was washed with saturated sodium bicarbonate solution (20 mL), the aqueous was extracted with DCM (3×50 mL), and the combined organics were dried (Na$_2$SO$_4$) and concentrated in vacuo. The crude product was purified by chromatography (SiO$_2$; 95:4.5:0.5→90:9:1 DCM/MeOH/28% aqueous NH$_3$) to obtain the title compound as a brown oil (109 mg, 62%). LCMS RT 1.46 minutes, (ES$^+$) 224 (M+H)$^+$.

Intermediate 63

2-Methyl-1,4,5,6-tetrahydropyrrolo[3,4-d]imidazole

To a solution of Intermediate 62 (86 mg, 0.39 mmol) in MeOH (4 mL) was added 4M HCl in 1,4-dioxane (4 mL) and the mixture was stirred for 3 h. After this time the solvent was removed in vacuo and azeotroped with toluene to afford the hydrochloride salt of the title compound (47 mg, quantitative), which was used in the next reaction without further purification.

Intermediate 64 cis-(3,6)-2-Phenyl-3a,4,6,6a-tetrahydro-1H-pyrrolo[3,4-d]imidazole-5-carboxylic acid tert-butyl ester To a solution of Intermediate 42 (130 mg, 0.65 mmol) in EtOH (7 mL) was added benzamidine (132 mg, 0.84 mmol) and the mixture stirred at 80° C. for 5 h. After this time the mixture was evaporated in vacuo. The crude product was purified by chromatography (SiO$_2$; 95:4.5:0.5→90:9:1 DCM/MeOH/28% aqueous NH$_3$) to obtain the title compound as a yellow oily solid (83 mg, 44%). $\delta_H$ (CDCl$_3$) 7.85-7.75 (2H, m), 7.53-7.39 (3H, m), 5.19-4.71 (2H, m), 3.84-3.51 (4H, m), 1.45 (9H, s). LCMS RT 0.74 minutes, (ES$^+$) 288 (M+H)$^+$.

Intermediate 65 cis-(3,6)-2-Phenyl-1,3a,4,5,6,6a-hexahydropyrrolo[3,4-d]imidazole

To a solution of Intermediate 64 (80 mg, 0.28 mmol) in MeOH (4 mL) was added 4M HCl in 1,4-dioxane (4 mL) and the mixture was stirred for 2.5 h. After this time the solvent was removed in vacuo and azeotroped with toluene to afford the hydrochloride salt of the title compound as a light brown solid (52 mg, quantitative). $\delta_H$ (CD$_3$OD) 7.96-7.90 (2H, m), 7.89-7.82 (1H, m), 7.75-7.67 (2H, m), 5.30 (2H, dd, J 3.8, 2.3 Hz), 3.86-3.79 (2H, m), 3.71-3.63 (2H, m). LCMS RT 0.29 minutes, (ES$^+$) 188 (M+H)$^+$.

Intermediate 66 cis-(3,6)-2-Isopropyl-3a,4,6,6a-tetrahydro-1H-pyrrolo[3,4-d]imidazole-5-carboxylic acid tert-butyl ester To a solution of Intermediate 42 (112 mg, 0.56 mmol) in EtOH (5 mL) was added isopropylcarbamidine hydrochloride (178 mg, 1.46 mmol) and the mixture stirred at 80° C. for 18 h. After this time the mixture was evaporated in vacuo. The crude product was purified by chromatography (SiO$_2$; 92.5:6.25:0.75→90:9:1 DCM/MeOH/28% aqueous NH$_3$) to obtain the title compound as a brown oil (114 mg, 80%). $\delta_H$ (CDCl$_3$) 4.61-4.26 (2H, m), 3.57 (2H, dd, J 1.9, 12.2 Hz), 3.52-3.44 (2H, m), 2.59-2.43 (2H, m), 1.45 (9H, s), 1.19 (3H, s), 1.17 (3H, s).

Intermediate 67 cis-(3,6)-2-Isopropyl-1,3a,4,5,6,6a-hexahydropyrrolo[3,4-d]imidazole

To a solution of Intermediate 66 (114 mg, 0.45 mmol) in MeOH (5 mL) was added 4M HCl in 1,4-dioxane (5 mL) and the mixture was stirred for 2.5 h. After this time the solvent was removed in vacuo and azeotroped with toluene to afford the hydrochloride salt of the title compound (69 mg, quantitative). $\delta_H$ (CD$_3$OD) 5.13-5.04 (2H, m), 3.73-3.66 (2H, m), 3.59-3.52 (2H, m), 3.01-2.87 (1H, m), 1.35 (3H, s), 1.32 (3H, s).

Intermediate 68 cis-(3,6)-2-(tert-Butyl)-3a,4,6,6a-tetrahydro-1H-pyrrolo[3,4-d]imidazole-5-carboxylic acid tert-butyl ester To a solution of Intermediate 42 (112 mg, 0.56 mmol) in EtOH (5 mL) was added tert-butylcarbamidine hydrochloride (198 mg, 1.45 mmol) and the mixture stirred at 80° C. for 18 h. After this time the mixture was evaporated in vacuo. The crude product was purified by chromatography (SiO$_2$; 90:9:1 DCM/MeOH/28% aqueous NH$_3$) to obtain the title compound as a yellow oil (103 mg, 67%). $\delta_H$ (CD$_3$OD) 4.47-4.39 (2H, m), 3.60 (2H, d, J 12.1 Hz), 3.46-3.35 (2H, m), 1.45 (9H, s), 1.19 (9H, s).

Intermediate 69 cis-(3,6)-2-(tert-Butyl)-1,3a,4,5,6,6a-hexahydropyrrolo[3,4-d]imidazole

To a solution of Intermediate 68 (103 mg, 0.39 mmol) in MeOH (5 mL) was added 4M HCl in 1,4-dioxane (5 mL) and the mixture was stirred for 2.5 h. After this time the solvent was removed in vacuo and azeotroped with toluene to afford the hydrochloride salt of the title compound (69 mg, quantitative). $\delta_H$ (CD$_3$OD) 5.09 (2H, dd, J 2.4, 3.6 Hz), 3.75-3.67 (2H, m), 3.63-3.53 (2H, m), 1.38 (9H, s).

Intermediate 70

N-[(3S,4R)-1-Benzyl-4-hydroxypyrrolidin-3-yl]-2-chloroacetamide

To a stirred solution of (−)-cis-(3R,4S)-4-amino-1-benzylpyrrolidin-3-ol (1 g, 5.201 mmol) and DIPEA (0.906 mL, 5.201 mmol) in DCM (300 mL) under nitrogen at −78° C. was added chloroacetyl chloride (0.4142 mL, 5.201 mmol) dropwise over 30 minutes. The reaction was allowed to warm to r.t. and stirred for 24 h. The volatiles were removed in vacuo and the crude residue purified by column chromatography (SiO$_2$; EtOAc) to give the title compound (0.47 g, 33%) as a white crystalline solid. $\delta_H$ (DMSO-d$_6$) 7.85 (1H, d, J 7.2 Hz), 7.34-7.20 (5H, m), 5.20 (1H, d, J 4.8 Hz), 4.18 (1H, m), 4.13 (2H, s), 4.04 (1H, m), 3.57 (2H, s), 2.94 (1H, dd, J 5.8, 4.2 Hz), 2.80 (1H, dd, J 7.0, 2.0 Hz), 2.42 (1H, dd, J 3.8, 8.2 Hz). LCMS (ES$^+$) 269 (M+H)$^+$, RT 0.90 minutes pH 10).

Intermediate 71

(4aS,7aR)-6-(Benzyl)hexahydropyrrolo[3,4-b][1,4]oxazin-3-one

To a stirred solution of potassium tert-butoxide (0.21 g, 1.7 mmol) in 1,4-dioxane (20 mL) was added Intermediate 70 (0.47 g, 1.75 mmol) in a mixture of DCM and 1,4-dioxane, and the reaction mixture was stirred for 1 h at ambient temperature. The volatiles were removed in vacuo and the crude residue was purified by column chromatography (SiO$_2$; 1:9 MeOH/EtOAc) to give the title compound (0.21 g, 52%) as a clear glass. $\delta_H$ (DMSO-d$_6$) 7.98 (1H, s), 7.35-7.15 (5H, m), 4.23 (1H, dt, J 2.1, 3.9 Hz), 3.89 (2H, d, J 7.4 Hz), 3.63 (1H, m), 3.60 (2H, s), 3.02 (1H, dd, J 6.1, 4.8 Hz), 2.72 (1H, dd, J 6.3, 2.4 Hz), 2.51 (1H, m), 2.45 (1H, t, J 2.3 Hz). LCMS (ES$^+$) 233 (M+H)$^+$, RT 0.86 minutes (pH 10).

Intermediate 72

(4aS,7aR)-Hexahydropyrrolo[3,4-b][1,4]oxazin-3-one

A stirred solution of Intermediate 71 (0.21 g, 0.91 mmol) in EtOH (100 mL) was hydrogenated using 20% Pd/C (100 mg) at atmospheric pressure of hydrogen for 24 h. The catalyst was removed by filtration and the reaction mixture was concentrated in vacuo to give the title compound as a semi-crystalline solid (0.12 g, 94%). $\delta_H$ (DMSO-d$_6$) 8.10 (1H, br s), 4.16 (1H, m), 3.97 (2H, s), 3.50 (1H, m), 3.35 (1H, br s), 3.23 (1H, dd, J 5.6, 7.1 Hz), 3.03 (1H, dd, J 6.83, 3.84 Hz), 2.79 (1H, dd, J 1.3, 11.3 Hz), 2.60 (1H, d, J 8.9 Hz).

Intermediate 73

2-Bromoethyl trifluoromethanesulfonate

Anhydrous pyridine (8.5 mL, 105 mmol) and dry DCM (100 mL) were added to a 3-necked round-bottomed flask under a nitrogen atmosphere. The reaction flask was then cooled to about −20° C. with a dry ice/ethylene glycol bath. Trifluoromethanesulfonic anhydride (17 mL, 100 mmol) was added, whereupon a white/pink precipitate formed immediately. 2-Bromoethanol (7.1 mL, 100 mmol) was added after 5 minutes. The precipitate disappeared and then after a few minutes a new white precipitate formed. The reaction mixture was stirred for 20 minutes during which time it gradually warmed to r.t. The reaction mixture was then filtered through a phase separator and the residue was washed with 1:1 DCM/hexane (2×10 mL). The filtrate was run through a 4 cm silica plug with 1:1 DCM/hexane solution (300 mL). The solvent was removed in vacuo to give the title compound as a brown oil (21.2 g, 87%). $\delta_H$ (CDCl$_3$) 4.76 (2H, t, J 6.4 Hz), 3.62 (2H, t, J 6.4 Hz).

Intermediate 74

(2-Bromoethyl)diphenylsulfonium trifluoromethanesulfonate

A solution of Intermediate 73 (21.1 g, 82.3 mmol) in anhydrous toluene (70 mL) was treated with phenyl sulfide (18.3 g, 98.7 mmol) at r.t. under nitrogen with stirring. The reaction mixture was heated to 100° C. under nitrogen for 5 h. The solution was allowed to cool to ambient temperature and diethyl ether (130 mL) added to precipitate the product which was isolated by filtration as a white powder (22.5 g, 62%). $\delta_H$ (CDCl$_3$) 8.14-8.10 (4H, m), 7.86-7.62 (6H, m), 4.91 (2H, t, J 5.8 Hz), 3.71 (2H, t, J 5.8 Hz).

Intermediate 75

(Diphenyl)(vinyl)sulfonium trifluoromethanesulfonate

Intermediate 74 (11.4 g, 25.7 mmol) was dissolved in THF/H$_2$O (2:1) (42 mL). KHCO$_3$ (3.1 g, 30.9 mmol) was added and the reaction mixture was stirred for 20 minutes at r.t. The solvent was evaporated immediately under reduced pressure (using a rotary evaporator connected to a high vacuum pump and keeping the water-bath temperature below 20° C.). The reaction mixture was then redissolved in DCM (40 mL), dried over MgSO$_4$, filtered and evaporated. The residue was redissolved in DCM (10 mL) and loaded onto a silica bed (4 cm depth and 2.5 cm diameter). The resulting band was covered with 1 cm sand and eluted with DCM (400 mL), followed by 10% MeOH in DCM (200 mL). The product was isolated as a light brown oil (9.53 g, quantitative). $\delta_H$ (CDCl$_3$) 7.90-7.87 (4H, m), 7.79-7.66 (6H, m), 7.53 (1H, dd, J 8.8, 8.8 Hz), 6.69 (1H, dd, J 9.5, 2.5 Hz), 6.55 (1H, dd, J 16.5, 2.5 Hz).

Intermediate 76

2-(Trimethylsilanyl)ethanesulfonic acid[(3S,4R)-1-benzyl-4-hydroxypyrrolidin-3-yl]-amide (−)-cis-(3R,4S)-4-Amino-1-benzylpyrrolidin-3-ol (5 g, 26 mmol) was dissolved in dry DMF (10 mL), cooled to 0° C., and triethylamine (3.6 mL, 26 mmol) was added under nitrogen. The reaction mixture was then treated with a solution of 2-(trimethylsilyl)-ethanesulfonyl chloride (4.93 g, 26 mmol) in DMF (2 mL). After stirring for 24 h at 0° C. to r.t. the solvent was removed in vacuo leaving a crude off-white semi-solid. Purification by chromatography (SiO$_2$; 6:4 hexane/EtOAc) gave the title compound (2 g, 22%) as a pale orange oil. The material was used as such for the subsequent step. LCMS (ES$^+$) 357 (MH)$^+$, RT 1.30 minutes (pH 10).

Intermediate 77

(4aS,7aR)-6-Benzyl-4-[2-(trimethylsilanyl)ethane-sulfonyl]octahydropyrrolo[3,4-b][1,4]oxazine A stirred solution of Intermediate 76 (2.0 g, 5.6 mmol) in DCM (20 mL) was treated with DBU (1.68 mL, 11.2 mmol) at 0° C. under nitrogen. After 10 minutes a solution of Intermediate 75 (2.18 g, 5.89 mmol) was added dropwise and the reaction mixture was stirred for 3 h at 0° C., followed by 24 h at r.t. The reaction was then quenched with saturated ammonium chloride solution (10 mL), extracted with DCM (3×50 mL), washed with brine (20 mL), dried over MgSO$_4$, filtered and concentrated in vacuo. Purification by chromatography (SiO$_2$; 6:4 hexane/EtOAc) gave the title compound (0.55 g, 25%) as a transparent glass. $\delta_H$ (CDCl$_3$) 7.34-7.18 (5H, m), 4.09 (1H, m), 3.95 (1H, t, J 4.4, 4.0 Hz), 3.86 (1H, br d), 3.71 (2H, q, J 14.4, 12.9 Hz), 3.54-3.41 (2H, m), 3.30-3.23 (1H, m), 3.21-3.12 (1H, dd), 2.90-2.77 (4H, m), 2.58 (1H, m), 1.05-0.75 (2H, m), 0.00 (9H, s). LCMS (ES$^+$) 384 (M+H)$^+$, RT 1.54 minutes.

Intermediate 78

(4aS,7aR)-4-[2-(Trimethylsilanyl)ethanesulfonyl] octahydropyrrolo[3,4-b][1,4]oxazine Intermediate 77 (0.55 g, 1.43 mmol) was hydrogenated using Pd(OH)$_2$ (100 mg) under 50 psi of hydrogen at 50° C. for 18 h. The catalyst was filtered off and the filtrate concentrated under vacuum to give the title compound (0.24 g, 57%) as a clear glass. $^1$H NMR analysis indicated loss of the benzyl protecting group and the material was used in the subsequent step without further purification.

Intermediate 79

[2-(2-Fluoro-4-iodophenylamino)thieno[2,3-b]pyridin-3-yl]-{(4aS,7aR)-4-[2-(trimethylsilanyl)ethane-sulfonyl]hexahydropyrrolo[3,4-b][1,4]oxazin-6-yl}-methanone To a stirred solution of Intermediate 78 (0.24 g, 0.82 mmol) in DCM (10 mL) was added DIPEA (0.14 mL, 0.82 mmol) followed by Intermediate 5 (0.34 g, 0.82 mmol), and the reaction mixture was stirred at r.t. for 24 h. Purification by column chromatography (SiO$_2$; 1:1 hexane/EtOAc) gave the title compound (0.4 g, 71%) as a pale orange solid. LCMS (ES$^+$) 689 (M+H)$^+$, RT 1.59 minutes pH 3).

Intermediate 80

(3S,4R)-3-Amino-pyrrolidin-4-ol (3S,4R)-3-Amino-1-benzylpyrrolidin-4-ol (2 g, 10.4 mmol) was dissolved in ethanol (200 mL) and treated with concentrated HCl (1 mL) and palladium hydroxide on carbon (200 mg). The suspension was hydrogenated in a Parr reactor under 50 psi at 50° C. for 18 h. After cooling, the catalyst was filtered off and the filtrate concentrated in vacuo to yield a colourless oil (950 mg). $\delta_H$ (DMSO-d$_6$) 6.17 (5H, br s), 4.12-4.04 (1H, m), 3.41-3.33 (1H, m), 3.23-3.13 (2H, m), 2.98 (1H, dd, J 12.1, 2.8 Hz), 2.79 (1H, dd, J 11.3, 8.3 Hz).

Intermediate 81

[3S,4R)-3-Amino-4-hydroxypyrrolidin-1-yl]-[2-(2-fluoro-4-iodophenylamino)thieno[2,3-b]pyridin-3-yl]-methanone To a solution of Intermediate 80 (100 mg, 0.58 mmol) in DMF (20 mL) was added Intermediate 5 (242 mg, 0.58 mmol) and DIPEA (270 mg, 2.10 mmol) and the mixture was stirred at r.t. for 18 h. After this time the reaction mixture was treated with brine (25 mL) and extracted into ethyl acetate (2×50 mL). After drying (Na$_2$SO$_4$) the solvent was removed in vacuo, leaving a brown residue which was purified by chromatography (SiO$_2$; 15% MeOH in DCM) to afford the title compound as a white powder (142 mg, 49%). $\delta_H$ (DMSO-d$_6$) 8.34 (1H, dd, J 1.6, 4.7 Hz), 7.85 (1H, dd, J 1.5, 8.1 Hz), 7.70 (1H, dd, J 1.9, 10.5 Hz), 7.50 (1H, m), 7.37 (1H, dd, J 4.7, 8.1 Hz), 7.18 (1H, dd, J 8.6, 8.6 Hz), 6.50 (1H, s), 4.15 (1H, m), 3.55 (4H, m). LCMS RT 1.95 minutes, (ES$^+$) 499 (M+H)$^+$.

Intermediate 82

Tetrahydropyrrolo[3,4-c]pyrrole-1,3-dione

A degassed solution of cis-5-(benzyl)tetrahydropyrrolo[3,4-c]pyrrole-1,3-(2H,3H)-dione (250 mg, 1.30 mmol) in methanol (50 mL) was treated with Pd/C (25 mg) and a hydrogen balloon was attached. The mixture was stirred for 48 h before filtering through celite and removal of the solvents in vacuo gave the title compound as a brown solid (125 mg, 88%). $\delta_H$ (DMSO-d$_6$) 11.01 (1H, s) 3.12 (4H, d, J 10.4 Hz), 2.75 (2H, m). LCMS RT 0.19 minutes, (ES$^+$) 141 (M+H)$^+$.

Intermediate 83

(3S,4S)-3-(3-Ethylureido)-4-hydroxypyrrolidine-1-carboxylic acid tert-butyl ester Intermediate 12 (500 mg, 2.49 mmol) in DCM (50 mL) was treated with ethyl isocyanate (177 mg, 2.49 mmol) and the reaction mixture was stirred for 18 h. The solvent was evaporated to afford the title compound (670 mg, 99%) as brown gum. $\delta_H$ (CDCl$_3$) 6.01 (1H, d, J 7.7 Hz), 5.66 (1H, m), 5.21 (1H, d, J 3.7 Hz), 3.88 (1H, m), 3.77 (1H, m), 3.43 (1H, m), 3.32 (1H, m), 3.07 (4H, m), 1.38 (9H, s), 0.96 (3H, t, J 7.2 Hz).

Intermediate 84

1-Ethyl-3-[(3S,4S)-4-hydroxypyrrolidin-3-yl]urea

To a solution of Intermediate 83 (670 mg, 3.9 mmol) in DCM (50 mL) was added 4M HCl in 1,4-dioxane (20 mL) and the reaction mixture was stirred for 3 h. After this time the solvent was evaporated to afford the title compound (542 mg, 81%) as a brown gum. $\delta_H$ (DMSO-d$_6$) 9.39 (1H, m), 9.29 (1H, m), 6.44 (1H, m), 4.12 (1H, m), 3.43 (1H, m), 3.27 (1H, m), 3.07 (4H, m), 0.98 (2H, t, J 7.2 Hz); pyrrolidine proton obscured by broad water peak.

Intermediate 85

1-Ethyl-3-{(3S,4S)-1-[2-(2-fluoro-4-iodophenylamino)thieno[2,3-b]pyridine-3-carbonyl]-4-hydroxypyrrolidin-3-yl}urea To a solution of Intermediate 84 (500 mg, 1.62 mmol) in DMF (25 mL) were added Intermediate 5 (677 mg, 1.62 mmol) and DIPEA (418 mg, 3.24 mmol) and the mixture stirred at r.t. for 1 h. After this time water was added until a beige-coloured precipitate formed. The precipitate was filtered off, and washed with water and diethyl ether to give the title compound as an off-white solid (920 mg, 99%). $\delta_H$ (DMSO-$d_6$) 9.18 (1H, s), 8.35 (1H, d, J 1.5 Hz), 7.82 (1H, m), 7.67 (1H, m), 7.49 (1H, d, J 8.4 Hz), 7.37 (1H, dd, J 4.9, 7.5 Hz), 7.19 (1H, dd, J 8.8, 8.8 Hz), 6.01 (1H, d, J 5.5 Hz), 5.72 (1H, m), 5.30 (1H, m), 3.94 (1H, m), 3.81 (1H, m), 3.68-3.59 (2H, m), 3.18 (2H, m), 2.98 (2H, m), 0.96 (3H, t, J 7.0 Hz). LCMS RT 1.90 minutes, (ES$^+$) 570 (M+H)$^+$.

Intermediate 86

(3S,4S)-3-Amino-4-hydroxypyrrolidine

Intermediate 12 (100 mg, 0.50 mmol) was treated with 4M HCl in 1,4-dioxane (5 mL) and stirred for 4 h. After this time the solvent was evaporated to afford the title compound as a white solid (86 mg, quantitative). $\delta_H$ (DMSO-$d_6$) 9.70-8.30 (4H, m), 6.10 (1H, m), 4.64 (1H, m), 3.62 (1H, m), 3.28 (2H, m), 3.11 (2H, m).

Intermediate 87

[(3S,4S)-3-Amino-4-hydroxypyrrolidin-1-yl]-[2-(2-fluoro-4-iodophenylamino)thieno[2,3-b]pyridin-3-yl]-methanone To a solution of Intermediate 86 (80 mg, 0.47 mmol) in DMF (5 mL) were added DIPEA (180 mg, 1.40 mmol) and Intermediate 5 (195 mg, 0.47 mmol) and the mixture was stirred at r.t. for 1 h. After this time the reaction mixture was treated with water (25 ml), until a white precipitate formed. This was filtered, and washed with water and diethyl ether, to give the title compound as a white solid (37 mg, 16%). $\delta_H$ (DMSO-$d_6$) 8.36 (1H, dd, J 1.5, 4.5 Hz), 7.81 (1H, dd, J 1.5, 8.1 Hz), 7.66 (1H, dd, J 1.7, 10.5 Hz), 7.48 (1H, m), 7.37 (1H, dd, J 4.7, 8.0 Hz), 7.16 (1H, dd, J 8.5, 8.5 Hz), 5.00 (1H, s), 3.76 (1H, m), 3.68-3.55 (3H, m), 3.16 (2H, m). LCMS RT 1.88 minutes, (ES$^+$) 499 (M+H)$^+$.

Intermediate 88

1-{(3S,4S)-1-[2-(2-Fluoro-4-iodophenylamino)thieno[2,3-b]pyridine-3-carbonyl]-4-hydroxypyrrolidin-3-yl}-3-(methyl)thiourea Intermediate 87 (350 mg, 0.71 mmol) in THF (25 mL) was treated with methyl isothiocyanate (52 mg, 0.71 mmol) and the reaction mixture was stirred for 18 h. The solvent was evaporated to afford the title compound (400 mg, 99%) as a brown gum. $\delta_H$ (DMSO-$d_6$) 9.21 (1H, s), 8.35 (1H, dd, J 1.5, 4.7 Hz), 7.82 (1H, m), 7.69 (1H, dd J 1.8, 10.4 Hz), 7.52 (1H, d, J 9.5 Hz), 7.35 (1H, dd, J 4.6, 8.0 Hz), 7.17 (1H, dd, J 8.7, 8.7 Hz), 5.43 (1H, d, J 4.0 Hz), 4.32 (1H, m), 4.03 (1H, m), 3.80 (1H, m), 3.64 (1H, m), 3.27 (2H, m), 2.80 (3H, s). LCMS RT 2.0 minutes, (ES$^+$) 572 (M+H)$^+$.

Intermediate 89

(3S,4S)-3-(tert-Butoxycarbonylamino)-4-(tert-butoxycarbonyloxy)pyrrolidine-1-carboxylic acid tert-butyl ester Intermediate 12 (1.14 g, 5.7 mmol) in THF (20 mL) was cooled in an ice-bath and treated with sodium hydride (0.80 g, 19.9 mmol) and the reaction mixture was stirred for 20 minutes. Di-tert-butyl dicarbonate (4.35 g, 19.9 mmol) was then added and the reaction mixture stirred for 18 h. After this time the reaction mixture was quenched with water (2 mL), diluted with ethyl acetate (50 mL), washed with brine (2×50 mL), dried (Na$_2$SO$_4$), filtered and evaporated in vacuo. The residue was purified by chromatography (SiO$_2$; 20% EtOAc in hexanes) to afford the title compound as a colourless oil (1.86 g, 81%). $\delta_H$ (DMSO-$d_6$) 7.40-7.29 (1H, m), 4.81 (1H, s), 3.98-3.86 (1H, m), 3.66-3.55 (1H, m), 3.52-3.42 (1H, m), 3.28-3.18 (2H, m), 1.43 (9H, m), 1.40 (9H, s), 1.39 (9H, s).

Intermediate 90

(3S,4S)-3-[N-(tert-Butoxycarbonyl)-N-methylamino]-4-(tert-butoxycarbonyloxy)-pyrrolidine-1-carboxylic acid tert-butyl ester To a solution of Intermediate 89 (500 mg, 1.67 mmol) in DMF (5 mL) was added sodium hydride (77 mg, 1.93 mmol) and the reaction mixture was stirred for 5 minutes. Iodomethane (261 mg, 1.8 mmol) was then added and the mixture was stirred for 3 h. After this time the solvent was quenched with water (1 mL), diluted with ethyl acetate (25 mL) and then washed with brine (2×50 mL). After drying (Na$_2$SO$_4$), the solvent was removed in vacuo to afford the title compound (410 mg, 78%) as a colourless oil. $\delta_H$ (DMSO-$d_6$) 5.11 (1H, m), 4.47 (1H, m), 3.73 (1H, m), 3.53 (1H, m), 3.27-3.20 (2H, m), 2.74 (3H, s), 1.41 (27H, m).

Intermediate 91

(3S,4S)-4-(Methylamino)pyrrolidin-3-ol

To a solution of Intermediate 90 (400 mg, 1.27 mmol) in DCM (50 mL) was added 4M HCl in 1,4-dioxane (30 mL) and the reaction mixture was stirred for 4 h. After this time the solvent was evaporated to afford the title compound (180 mg, 79%) as a brown gum. $\delta_H$ (DMSO-$d_6$) 9.70-9.30 (4H, m), 6.14 (1H, m), 4.58 (1H, m), 3.65 (3H, m), 3.17 (2H, m), 2.94 (3H, m).

Intermediate 92

[2-(2-Fluoro-4-iodophenylamino)thieno[2,3-b]pyridin-3-yl]-[(3S,4S)-3-hydroxy-4-(methylamino)pyrrolidin-1-yl]-methanone To a solution of Intermediate 91 (180 mg, 0.97 mmol) in DMF (25 mL) were added Intermediate 5 (400 mg, 0.97 mmol) and DIPEA (375 mg, 2.91 mmol) and the mixture was stirred at r.t. for 1 h. After this time water was added until a beige-coloured precipitate formed. The precipitate was filtered off and purified by chromatography (SiO$_2$; 10% MeOH in DCM) to afford the title compound as an off-white powder (280 mg, 56%). $\delta_H$ (DMSO-$d_6$) 8.36 (1H, dd, J 1.6, 4.7 Hz), 7.80 (1H, dd, J 1.5, 8.5 Hz), 7.68 (1H, dd, J 1.8, 10.5 Hz), 7.50 (1H, d, J 8.4 Hz), 7.37 (1H, dd, J 4.6, 8.1 Hz), 7.15 (1H, dd, J 8.6, 8.6 Hz), 5.07 (1H, m), 3.95 (1H, m), 3.60 (2H, m), 3.23 (2H, m), 2.87 (1H, m), 2.24 (3H, s). LCMS RT 1.12 minutes, (ES$^+$) 513 (M+H)$^+$.

Intermediate 93

1-{(3S,4S)-1-[2-(2-Fluoro-4-iodophenylamino) thieno[2,3-b]pyridine-3-carbonyl]-4-hydroxypyrrolidin-3-yl}-1-methyl-3-(9H-fluoren-9-ylmethoxycarbonyl)thiourea Intermediate 92 (125 mg, 0.24 mmol) in DCM (25 mL) was treated with 9H-fluoren-9-ylmethoxycarbonyl isothiocyanate (82 mg, 0.29 mmol) and the mixture was stirred for 18 h. The volatiles were removed in vacuo to give a yellow oil which was purified by chromatography (SiO$_2$; EtOAc) to give the title compound as a white powder (146 mg, 77%). $\delta_H$ (DMSO-d$_6$) 10.36 (1H, s), 9.26 (1H, s), 8.35 (1H, m), 7.89 (3H, m), 7.74 (2H, m), 7.67 (1H, m), 7.55-7.30 (6H, dd, J 4.6, 8.1 Hz), 7.17 (1H, dd, J 8.7, 8.7 Hz), 4.45-4.24 (4H, m), 3.83 (1H, m), 3.68 (1H, m), 3.25-2.91 (6H, m). LCMS RT 1.56 minutes, (ES$^+$) 794 (M+H)$^+$.

Intermediate 94

{(3aS,6aR)-5-[2-(2-Fluoro-4-iodophenylamino) thieno[2,3-b]pyridine-3-carbonyl]-3-(methyl) hexahydropyrrolo[3,4-d]thiazol-(2E)-ylidene}carbamic acid 9H-fluoren-9-ylmethyl ester To a solution of Intermediate 93 (140 mg, 0.176 mmol) in DCM (25 mL), cooled in an acetone/cardice bath, was added DAST (23 mg, 0.176 mmol) and the mixture was stirred for 60 minutes before being allowed to warm up to r.t. After 3 h the reaction mixture was diluted with DCM (50 mL) and washed with sodium bicarbonate solution (50 mL). After drying (Na$_2$SO$_4$), the organics were evaporated in vacuo to give a yellow oil and then purified by chromatography (SiO$_2$; 20% EtOAc in hexanes) to afford the title compound as an orange-coloured solid (84 mg, 62%). $\delta_H$ (DMSO-d$_6$) 9.23 (1H, s), 8.32 (1H, m), 7.89 (2H, d, J 7.4 Hz), 7.72-7.15 (11H, m), 4.48 (1H, m), 4.41 (2H, m), 4.27 (1H, m), 4.19 (1H, m), 3.82 (2H, m), 3.62 (2H, m), 2.90 (3H, m). LCMS RT 3.144 minutes, (ES$^+$) 776 (M+H)$^+$.

Intermediate 95

(3aS,6aR)-5-(Benzyl)hexahydropyrrolo[3,4-d]oxazol-2-one (3R,4S)-4-Amino-1-benzylpyrrolidin-3-ol (6 g, 31.4 mmol) in DMF (100 mL) was treated with CDI (5 g, 31.4 mmol) and the reaction mixture was stirred at r.t. for 18 h. The reaction was concentrated in vacuo and azeotroped with heptane. The residual oil was chromatographed on silica with a mixture of dichloromethane and methanol (gradient elution 0-10% methanol), yielding a colourless oil (6 g) which crystallized on standing. $\delta_H$ (DMSO-d$_6$) 7.58 (1H, s), 7.29 (5H, m), 4.96 (1H, dd, J 7.9, 4.5 Hz), 4.16 (1H, dd, J 7.7, 4.9 Hz), 3.59 (2H, m), 3.00 (1H, d, J 11.1 Hz), 2.76 (1H, m), 2.19 (1H, dd, J 11.3, 4.5 Hz), 2.08 (1H, dd, J 10.2, 4.9 Hz).

Intermediate 96

(3aS,6aR)-5-(Benzyl)-3-(methyl)hexahydropyrrolo [3,4-d]oxazol-2-one

Intermediate 95 (500 mg, 2.3 mmol) in DMF (5 mL) was treated at r.t. under nitrogen with sodium hydride (110 mg, 2.75 mmol) and the reaction mixture was stirred for 30 minutes. Methyl iodide (327 mg, 2.3 mmol) was added and the reaction heated at 80° C. for 2 h. The reaction mixture was cooled to r.t. and partitioned between DCM and water. The organic phase was separated, dried over sodium carbonate, filtered and concentrated in vacuo, yielding the title compound (580 mg). $\delta_H$ (DMSO-d$_6$) 7.30 (5H, m), 4.90 (1H, dd, J 7.9, 4.7 Hz), 4.16 (1H, dd, J 7.9, 4.9 Hz), 3.61 (2H, m), 3.28 (2H, m), 2.73 (3H, s), 2.23 (1H, dd, J 11.1, 4.7 Hz), 2.05 (1H, dd, J 10.5, 4.7 Hz).

Intermediate 97

(3aS,6aR)-3-(Methyl)hexahydropyrrolo[3,4-d]oxazol-2-one

Intermediate 96 (580 mg, 2.52 mmol) in ethanol was treated with palladium hydroxide on carbon (80 mg) and concentrated HCl (1 mL). The mixture was subjected to hydrogenation under 50 psi at 50° C. for 18 h. Filtration and concentration in vacuo gave the title compound (290 mg). $\delta_H$ (DMSO-d$_6$) 5.15 (1H, m), 4.46 (1H, m), 3.55 (2H, dd, J 25.1, 12.8 Hz), 3.30 (2H, m), 3.08 (1H, dd, J 12.4, 4.7 Hz), 2.74 (3H, s).

Example 1

5-[2-(2-Fluoro-4-iodophenylamino)thieno[2,3-b] pyridine-3-carbonyl]-3-methyl-hexahydropyrrolo[3, 4-d]oxazol-2-one To a solution of Intermediate 10 (140 mg, 0.8 mmol) and DIPEA (0.3 mL, 3 mmol) in DMF (10 mL) was added Intermediate 5 (200 mg, 0.48 mmol). The mixture was stirred for 1 h at room temperature at which time the mixture was evaporated in vacuo. The crude product was purified by chromatography (SiO$_2$; ethyl acetate) to afford the title compound as a white powder (125 mg, 0.23 mmol, 48%). $\delta_H$ (DMSO-d$_6$) 9.25 (1H, s), 8.35 (1H, dd, J 1.5, 4.7 Hz), 7.66 (2H, m), 7.50 (1H, d, J 8.5 Hz), 7.35 (1H, dd, J 4.7, 8.1 Hz), 7.23 (1H, dd, J 8.6 8.6 Hz), 5.02 (1H, m), 4.28 (1H, m), 3.84 (2H, m), 3.46 (1H, m), 3.21 (1H, m), 2.63 (3H, s). LCMS RT 2.39 minutes, (ES$^-$) 537 (M−H)$^-$, (ES$^+$) 539 (M+H)$^+$.

Example 2

(3aS,6aR)-5-[2-(2-Fluoro-4-iodophenylamino)thieno [2,3-b]pyridine-3-carbonyl]-hexahydropyrrolo[3,4-d] oxazol-2-one To a solution of Intermediate 15 (200 mg, 1.22 mmol) and DIPEA (364 mg, 2.83 mmol) in DMF (10 mL) was added Intermediate 5 (400 mg, 0.96 mmol) and the mixture stirred for 18 h. After this time water (10 mL) was added to the reaction mixture and the resulting black precipitate filtered off. The crude product was purified by chromatography (SiO$_2$; 5% MeOH in DCM) to obtain the title compound as a grey powder (87 mg, 14%). $\delta_H$ (DMSO-d$_6$) 9.26 (1H, s), 8.36 (1H, dd, J 1.5, 4.7 Hz), 7.71 (3H, m), 7.53 (1H, d, J 8.2 Hz), 7.37 (1H, dd, J 4.6, 8.4 Hz), 7.19 (1H, dd, J 8.6, 8.6 Hz), 5.08 (1H, m), 4.30 (1H, m), 3.90 (1H, m), 2.72 (1H, m), 3.31 (2H, m). LCMS RT 2.05 minutes, (ES) 523 (M−H)$^-$, (ES$^+$) 525 (M+H)$^+$.

Example 3

(3aR,6aS)-5-[2-(2-Fluoro-4-iodophenylamino)thieno[2,3-b]pyridine-3-carbonyl]-tetrahydro[1,3]dioxolo[4,5-c]pyrrol-2-one To a solution of Intermediate 18 (98 mg, 0.189 mmol) in DMF (5 mL) was added CDI (31 mg, 0.19 mmol) and the mixture stirred for 18 h. After this time the solvent was removed in vacuo, and the crude product was purified by chromatography (SiO$_2$; ethyl acetate) to obtain the title compound as a white powder (28 mg, 28%). $\delta_H$ (DMSO-d$_6$) 9.33 (1H, s), 8.34 (1H, m), 7.75 (1H, m), 7.68 (1H, m), 7.52 (1H, m), 7.35 (1H, s), 7.25 (1H, dd, J 8.4, 8.4 Hz), 5.75 (2H, m), 4.01 (2H, m), 3.46 (2H, m). LCMS RT 2.74 minutes, (ES$^-$) 524 (M−H)$^-$, (ES$^+$) 526 (M+H)$^+$.

Example 4

(3aR,6aS)-5-[2-(2-Fluoro-4-iodophenylamino)thieno[2,3-b]pyridine-3-carbonyl]-hexahydropyrrolo[3,4-d]oxazol-2-one To a solution of Intermediate 25 (100 mg, 0.20 mmol) in DMF (5 mL) was added CDI (49 mg, 0.30 mmol) and the mixture stirred for 3 h. After this time brine (10 mL) was poured onto the mixture and the resulting precipitate filtered off. This crude product was purified by chromatography (SiO$_2$; 5% MeOH in DCM) to obtain the title compound as a white powder (56 mg, 53%). $\delta_H$ (DMSO-d$_6$) 9.28 (1H, s), 8.36 (1H, dd, J 1.5, 4.7 Hz), 7.71 (2H, m), 7.69 (1H, m), 7.51 (1H, d, J 8.4 Hz), 7.36 (1H, dd, J 4.6, 8.4 Hz), 7.19 (1H, dd, J 8.6, 8.6 Hz), 5.08 (1H, m), 4.30 (1H, m), 3.90 (1H, m), 3.70 (1H, s), 3.31 (2H, m). LCMS RT 2.37 minutes, (ES$^-$) 523 (M−H)$^-$, (ES$^+$) 525 (M+H)$^+$.

Example 5

[2-(2-Fluoro-4-iodophenylamino)thieno[2,3-b]pyridin-3-yl]-[3aS,6aR)-2-phenyl-3a,4,6,6a-tetrahydro-pyrrolo[3,4-d]oxazol-5-yl]-methanone Intermediate 28 (225 mg, 1 mmol) in DMF (3 mL) and DIPEA (390 mg, 0.52 mL, 3 mmol) was treated at room temperature with Intermediate 5 (397 mg, 1 mmol) and stirred at room temperature overnight. The DMF was removed in vacuo, the residue was dissolved in DCM and washed with water, and the organic phase was dried over sodium sulphate and concentrated in vacuo. Chromatography (SiO$_2$; DCM/ethyl acetate) yielded the title compound (30 mg). $\delta_H$ (DMSO-d$_6$) 9.00-9.30 (1H, m), 8.22-8.43 (1H, m), 6.86-7.94 (10H, m), 5.26 (1H, dd, J 7.5, 4.7 Hz), 4.83 (1H, t, J 7.2 Hz), 4.03 (1H, d, J 13.8 Hz), 3.82 (1H, d, J 11.9 Hz), 3.35-3.64 (2H, m). LCMS RT 3.04 minutes, (ES$^+$) 585 (M+H)$^+$.

Example 6 cis-(4,7)-6-({2-[(2-Fluoro-4-iodophenyl)amino]thieno[2,3-b]pyridin-3-yl}carbonyl)hexahydropyrrolo[3,4-d][1,3]oxazin-2(1H)-one Intermediate 31 (100 mg, 0.20 mmol) in DMF (2.5 mL) was treated with CDI (35 mg, 0.21 mmol) and stirred at room temperature for 3 h. The reaction mixture was diluted with ethyl acetate, and the organic solution washed with brine, then dried over sodium sulfate and concentrated in vacuo. Chromatography (SiO$_2$; 97:3 DCM/MeOH) yielded the title compound as a white powder (57 mg, 54%). $\delta_H$ (DMSO-d$_6$) 9.12 (1H, s), 8.36 (1H, dd, J 4.5, 1.3 Hz), 7.78-7.81 (1H, m), 7.69 (1H, dd, J 10.5, 1.7 Hz), 7.50-7.53 (1H, m), 7.36 (1H, dd, J 8.1, 4.7 Hz), 7.24 (1H, s), 7.14 (1H, dd, J 8.7, 8.7 Hz), 4.23 (1H, dd, J 11.3, 3.0 Hz), 4.04-4.09 (1H, m), 3.92 (1H, m), 3.49-3.64 (2H, m), 3.37-3.49 (2H, m), 2.62-2.75 (1H, m). LCMS RT 2.09 minutes, (ES$^+$) 539.0 (M+H)$^+$.

Example 7

3-[cis-(1,5)-3,6-Diazabicyclo[3.2.0]hept-3-ylcarbonyl]-N-(2-fluoro-4-iodophenyl)thieno[2,3-b]pyridin-2-amine A solution of Intermediate 32 (199 mg, 0.33 mmol) in DCM (5 mL) was treated with trifluoroacetic acid (3 mL) and stirred at room temperature for 1.5 h. The solvents were removed in vacuo and the residues were dissolved in MeOH, basified to pH 10 with 28% aqueous NH$_3$ and concentrated in vacuo onto SiO$_2$. Chromatography (SiO$_2$; 93:6.3:0.7 DCM/MeOH/28% aqueous NH$_3$) yielded the title compound, which was freeze-dried from acetonitrile/water to a pale yellow powder (138 mg, 83%). $\delta_H$ (DMSO-d$_6$) 8.32 (1H, dd, J 4.5, 1.1 Hz), 7.88 (1H, m), 7.68 (1H, dd, J 10.5, 2.1 Hz), 7.49-7.52 (1H, m), 7.35 (1H, dd, J 8.1, 4.7 Hz), 7.23 (1H, dd, J 8.7, 8.7 Hz), 4.32 (1H, m), 4.05 (1H, m), 3.64-3.71 (2H, m), 3.07-3.20 (3H, m), 2.88-2.94 (1H, m). LCMS RT 1.58 minutes, (ES$^+$) 495.0 (M+H)$^+$.

Example 8 trans-(4,7)-6-({2-[(2-Fluoro-4-iodophenyl)amino]thieno[2,3-b]pyridin-3-yl}carbonyl)hexahydropyrrolo[3,4-d][1,3]oxazin-2(1H)-one Intermediate 35 (38 mg, 0.07 mmol) in DMF (2 mL) was treated with CDI (13 mg, 0.08 mmol) and stirred at room temperature for 4 days. The reaction mixture was diluted with ethyl acetate, and the organic solution washed with brine, then dried over sodium sulfate and concentrated in vacuo. Chromatography (SiO$_2$; 97:3 DCM/MeOH) yielded the title compound, which was freeze-dried from acetonitrile/water to a white powder (18 mg, 44%). $\delta_H$ (DMSO-d$_6$) 9.27 (1H, s), 8.33-8.35 (1H, m), 7.78-7.84 (1H, m), 7.69-7.73 (2H, m), 7.51-7.53 (1H, m), 7.36 (1H, dd, J 7.9, 4.7 Hz), 7.16 (1H, dd, J 8.7, 8.7 Hz), 4.37 (1H, m), 4.16-4.23 (1H, m), 3.38-3.59 (3H, m), 3.09-3.24 (2H, m), 2.18-2.27 (1H, m). LCMS RT 2.18 minutes, (ES$^+$) 539.0 (M+H)$^+$.

Example 9

N-(2-Fluoro-4-iodophenyl)-3-[cis-(3,6)-hexahydropyrrolo[3,4-b]pyrrol-5(1H)-ylcarbonyl]thieno[2,3-b]pyridin-2-amine Intermediate 38 (301 mg, 0.47 mmol) in trifluoroacetic acid was heated to 50° C. for 7.5 h, then cooled to room temperature and concentrated in vacuo. The residue was dissolved in methanol, basified with 28% aqueous NH$_3$, and evaporated onto SiO$_2$ in vacuo. Chromatography (SiO$_2$; 97:3 DCM/MeOH) yielded the title compound, which was freeze-dried from acetonitrile/water to a pale yellow powder (205 mg, 86%). $\delta_H$ (DMSO-d$_6$) 8.35 (1H, dd, J 4.5, 1.5 Hz), 7.81 (1H, dd, J 8.1, 1.3 Hz), 7.68 (1H, dd, J 10.5, 1.9 Hz), 7.49 (1H, ddd, J 8.5, 1.9, 0.9 Hz), 7.35 (1H, dd, J 8.1, 4.7 Hz), 7.16 (1H, dd, J 8.7, 8.7 Hz), 3.63-3.68 (1H, m), 3.43-3.53 (2H, m), 3.26-3.31 (2H, m), 2.75 (2H, t, J 6.6 Hz), 2.65 (1H, m), 1.71-1.82 (1H, m), 1.40-1.50 (1H, m). LCMS RT 1.62 minutes, (ES$^+$) 509.0 (M+H)$^+$.

Example 10 meso-N-(2-Fluoro-4-iodophenyl)-3-[3aR*,6aS*)-tetrahydro-5H-spiro[1,3-dioxolo[4,5-c]pyrrole-2,4'-piperidin]-5-ylcarbonyl]thieno[2,3-b]pyridin-2-amine Intermediate 18 (200 mg, 0.40 mmol) was suspended in anhydrous toluene (5 ml) and tert-butyl 4-oxopiperidine-1-carboxylate (159 mg, 0.8 mmol) and p-toluenesulfonic acid monohydrate (152 mg, 0.8 mmol) were added sequentially. The reaction mixture was refluxed for 4 h and then cooled to r.t. Toluene was removed in vacuo resulting in a pale yellow oil which was partitioned between EtOAc and a saturated solution of NaHCO$_3$. The organic layer was separated, dried (Na$_2$SO$_4$) and the solvent removed to yield an off-white solid. This was stirred in Et$_2$O (5 ml) for 2 h to yield the title compound as a white solid (120 mg, 52%). $\delta_H$ (CDCl$_3$) 8.38-8.34 (1H, m), 7.83 (1H, dd, J 7.9, 1.1 Hz), 7.68 (1H, dd, J 10.1, 1.7 Hz), 7.49 (1H, d, J 8.1 Hz), 7.36 (1H, dd, J 8.1, 4.7 Hz), 7.20 (1H, t, J 8.7 Hz), 4.7 (2H, d, J 1.7 Hz), 3.85-3.72 (2H, m), 3.32-3.20 (4H, m), 2.65-2.58 (2H, m), 2.48 (1H, br s), 1.50-1.42 (4H, m). LCMS RT 1.69 minutes, (ES$^-$) 581 (M−H)$^-$, (ES$^+$) 579 (M+H)$^+$.

Example 11 meso-(3aR*,6aS*)-5-({2-[(2-Fluoro-4-iodophenyl)amino]thieno[2,3-b]pyridin-3-yl}carbonyl)tetrahydro-3aH-[1,3,2]dioxaphospholo[4,5-c]pyrrol-2-ol 2-oxide N,N-Diisopropylethylamine (70 µl, 0.4 mmol) and methyl dichlorophosphate (26 µl, 0.2 mmol) were added sequentially to a solution of Intermediate 18 (100 mg, 0.2 mmol) in THF (2 ml). The reaction mixture was stirred for 3 h at 50° C. and then further methyl dichlorophosphate (26 µl, 0.2 mmol) was added. After 18 h at 50° C., the THF was removed and the remaining oil purified using preparative HPLC. The compound was isolated from the resulting acetonitrile/water mixture by freeze-drying to yield the ammonium salt of the title compound as a fine white powder (15 mg, 13%). $\delta_H$ (CDCl$_3$) 10.90 (1H, br s), 8.27-8.23 (1H, m), 7.75 (1H, br s), 7.70 (1H, dd, J 10.2, 1.7 Hz), 7.57-7.51 (1H, m), 7.34-7.15 (3H, m), 4.80-4.69 (2H, m), 4.77-4.67 (2H, m), 3.41-3.35 (2H, m). LCMS RT 1.56 minutes, (ES$^-$) 560 (M−H)$^-$, (ES$^+$) 562 (M+H)$^+$.

Example 12

N-(2-Fluoro-4-iodophenyl)-3-{[cis-(3,6)-2-methyl-3a,4,6,6a-tetrahydropyrrolo[3,4-d]imidazol-5(1H)-yl]carbonyl}thieno[2,3-b]pyridin-2-amine To a solution of Intermediate 44 (95 mg, 0.75 mmol) and DIPEA (0.39 mL, 2.26 mmol) in DMF (4 mL) was added Intermediate 5 (159 mg, 0.38 mmol) in DMF (2 mL). The mixture was stirred for 18 h at room temperature at which time the mixture was evaporated in vacuo. The residue was diluted with EtOAc (15 mL) and washed with brine (3×15 mL), the aqueous was back-extracted with EtOAc (2×50 mL) and 10% MeOH/DCM (3×30 mL), and the combined organics were dried (Na$_2$SO$_4$) and concentrated in vacuo. The crude product was purified by chromatography (SiO$_2$; 95:4.5:0.5→90:9:1 DCM/MeOH/28% aqueous NH$_3$) to obtain the title compound, which was freeze-dried from acetonitrile/water to give a pale yellow solid (58 mg, 29%). $\delta_H$ (DMSO-d$_6$) 8.35 (1H, dd, J 1.5, 4.7 Hz), 7.74 (1H, dd, J 1.5, 8.1 Hz), 7.68 (1H, dd, J 1.9, 10.5 Hz), 7.50 (1H, ddd, J 0.9, 2.1, 8.5 Hz), 7.36 (1H, dd, J 4.7, 8.1 Hz), 7.16 (1H, dd, J 8.7, 8.7 Hz), 4.27-4.35 (2H, m), 3.55-3.68 (2H, m), 3.34-3.45 (2H, m), 1.72 (3H, s). LCMS RT 1.58 minutes, (ES$^+$) 522 (M+H)$^+$.

Example 13 cis-(3,6)-5-[2-(2-Fluoro-4-iodophenylamino)thieno[2,3-b]pyridine-3-carbonyl]-hexahydropyrrolo[3,4-d]imidazol-2-one To a solution of Intermediate 46 (46 mg, 0.36 mmol) and DIPEA (0.68 mL, 3.87 mmol) in DMF (3 mL) was added Intermediate 5 (150 mg, 0.36 mmol) in DMF (4 mL). The mixture was stirred for 56 h at room temperature at which time the mixture was evaporated in vacuo. The residue was diluted with EtOAc (30 mL) and washed with brine (3×30 mL), the aqueous was back-extracted with EtOAc (100 mL), and the combined organics were dried (Na$_2$SO$_4$) and concentrated in vacuo. The crude product was purified by chromatography (SiO$_2$; 95:4.5:0.5→92.5:6.75:0.75 DCM/MeOH/28% aqueous NH$_3$) to obtain the title compound as a yellow solid (65 mg, 34%). $\delta_H$ (DMSO-d$_6$) 8.88-9.45 (1H, m), 8.36 (1H, dd, J 1.5, 4.7 Hz), 7.80 (1H, dd, J 1.5, 8.1 Hz), 7.69 (1H, dd, J 1.9, 10.4 Hz), 7.49-7.54 (1H, m), 7.36 (1H, dd, J 4.7, 8.1 Hz), 7.16 (1H, dd, J 8.7, 8.7 Hz), 6.41 (2H, s), 4.11-4.19 (2H, m), 3.53-3.71 (2H, m), 3.30-3.45 (2H, m). LCMS RT 1.75 minutes, (ES$^+$) 524 (M+H)$^+$.

Example 14

[3aS,6aR)-2-Amino-3a,4,6,6a-tetrahydropyrrolo[3,4-c]thiazol-5-yl]-[2-(2-fluoro-4-iodo-phenylamino)thieno[2,3-b]pyridin-3-yl]-methanone To a solution of Intermediate 49 (140 mg, 0.383 mmol) in DMF (5 mL) was added DIPEA (60 mg, 0.460 mmol) before being treated with Intermediate 5 (160 mg, 0.38 mmol). After 1 hour, brine was added to the reaction mixture and a yellow precipitate formed. This was filtered off and purified by chromatography (SiO$_2$; 5% MeOH in DCM) to afford the title compound (78 mg, 38%). $\delta_H$ (DMSO-d$_6$) 9.23 (1H, s), 8.35 (1H, d, J 4.5 Hz), 7.80 (1H, m), 7.68 (1H, m), 7.50 (1H, m), 7.35 (1H, dd, J 4.7, 8.0 Hz), 7.17 (1H, dd, J 8.5, 8.5 Hz), 6.42 (2H, s), 4.69 (1H, m), 4.20 (1H, m), 3.84-3.45 (4H, m). LCMS RT 2.27 minutes, (ES$^+$) 540 (M+H)$^+$.

Example 15

[(3aS,6aR)-2-(Cyclopropylamino)-3a,4,6,6a-tetrahydropyrrolo[3,4-d]thiazol-5-yl]-[2-(2-fluoro-4-iodophenylamino)thieno[2,3-b]pyridin-3-yl]-methanone To a solution of Intermediate 52 (73 mg, 0.57 mmol) in DMF (5 mL) was added DIPEA (75 mg, 0.57 mmol) before being treated with Intermediate 5 (200 mg, 0.51 mmol). After 1 hour, brine was added to the reaction mixture and a pale precipitate formed. This was filtered off and purified by chromatography (SiO$_2$; 5% MeOH in DCM) to afford the title compound as a white powder (98 mg, 33%). $\delta_H$ (DMSO-d$_6$) 9.23 (1H, s), 8.35 (1H, d, J 4.7 Hz), 7.80 (1H, d, J 7.9 Hz), 7.68

(1H, m), 7.50 (1H, m), 7.35 (1H, dd, J 4.7, 7.9 Hz), 7.17 (1H, dd, J 8.6, 8.6 Hz), 7.08 (1H, s), 4.71 (1H, m), 4.20 (1H, m), 3.84-3.45 (5H, m), 0.54 (2H, m), 0.37 (2H, m). LCMS RT 2.65 minutes, (ES$^+$) 580 (M+H)$^+$.

Example 16

[(3aS,6aR)-2-Amino-3a,4,6,6a-tetrahydropyrrolo[3,4-d]oxazol-5-yl]-[2-(2-fluoro-4-iodo-phenylamino)thieno[2,3-b]pyridin-3-yl]-methanone To a solution of Intermediate 55 (219 mg, 1.10 mmol) in DMF (5 mL) was added DIPEA (429 mg, 3.33 mmol) before being treated with Intermediate 5 (400 mg, 0.96 mmol). After 18 hours, the reaction mixture was separated between brine and ethyl acetate. The aqueous was extracted with additional ethyl acetate (50 mL) and the organics combined, dried (Na$_2$SO$_4$) and evaporated to give an orange residue. This was purified by flash chromatography (SiO$_2$; 15% MeOH in DCM) to afford the title compound as a white powder (25 mg, 5%). $\delta_H$ (DMSO-d$_6$) 9.23 (1H, s), 8.35 (1H, d, J 4.7 Hz), 7.77 (1H, d, J 7.9 Hz), 7.68 (1H, m), 7.52 (1H, m), 7.36 (1H, dd, J 4.7, 7.9 Hz), 7.18 (1H, m), 5.94 (2H, s), 4.95 (2H, m), 4.42 (1H, m), 3.87 (1H, m), 3.55 (1H, m), 3.32 (2H, m). LCMS RT 1.70 minutes, (ES$^+$) 524.0 (M+H)$^+$.

Example 17

[2-(2-Fluoro-4-iodophenylamino)thieno[2,3-b]pyridin-3-yl][(3aS,6aR)-2-thioxo-hexahydropyrrolo[3,4-d]oxazol-5-yl]-methanone To a solution of Intermediate 57 (98 mg, 0.544 mmol) in DMF (5 mL) was added DIPEA (210 mg, 1.62 mmol) before being treated with Intermediate 5 (285 mg, 0.68 mmol). After 5 hours brine was added to the reaction mixture and a pale precipitate formed. This was filtered off and purified by chromatography (SiO$_2$; 5% MeOH in DCM) to afford the title compound as a white powder (110 mg, 38%). $\delta_H$ (DMSO-d$_6$) 10.02 (1H, s), 9.23 (1H, s), 8.35 (1H, d, J 4.7 Hz), 7.70-7.68 (2H, m), 7.50 (1H, m), 7.35 (1H, dd, J 4.7, 8.0 Hz), 7.20 (1H, dd, J 8.6, 8.6 Hz), 5.42 (1H, m), 4.54 (1H, m), 4.00 (1H, m), 3.77 (1H, m), 3.40 (1H, m), 3.15 (1H, m). LCMS RT 2.47 minutes, (ES$^+$) 541.0 (M+H)$^+$.

Example 18

N-(2-Fluoro-4-iodophenyl)-3-[cis-(4,7)-octahydro-6H-pyrrolo[3,4-b]pyridin-6-ylcarbonyl]thieno[2,3-b]pyridin-2-amine 4M HCl in 1,4-dioxane (5 mL) was added to a solution of Intermediate 58 (133 mg, 0.21 mmol) in MeOH (10 mL) and the reaction was stirred for 5 h at r.t., then concentrated in vacuo. The residue was dissolved in MeOH, basified with 28% aqueous NH$_3$, and evaporated onto SiO$_2$ in vacuo. Chromatography (SiO$_2$; 95:4.5:0.5 DCM/MeOH/28% aqueous NH$_3$) yielded the title compound, which was freeze-dried from acetonitrile/water to afford a cream-coloured powder (88 mg, 79%). $\delta_H$ (DMSO-d$_6$) 9.22 (1H, br s), 8.36 (1H, dd, J 4.5, 1.5 Hz), 7.82 (1H, dd, J 8.1, 1.5 Hz), 7.67 (1H, dd, J 10.5, 1.9 Hz), 7.49 (1H, ddd, J 8.3, 1.9, 0.9 Hz), 7.37 (1H, dd, J 8.1, 4.7 Hz), 7.13 (1H, dd, J 8.7, 8.7 Hz), 3.47-3.13 (5H, m), 2.78-2.74 (1H, m), 2.45-2.39 (1H, m), 2.07 (1H, m), 1.53-1.24 (4H, m). LCMS RT 1.64 minutes, (ES$^+$) 523.0 (M+H)$^+$.

Example 19 cis-(3,6)-5-({2-[2-Fluoro-4-iodophenyl)amino]thieno[2,3-b]pyridin-3-yl}carbonyl)-hexahydropyrrolo[3,4-b]pyrrol-2(1H)-one A mixture of Intermediate 61 (46 mg, 0.37 mmol) and DIPEA (0.1 mL, 0.55 mmol) in DMF (3 mL) was treated with Intermediate 5 (152 mg, 0.37 mmol) and stirred at r.t. for 5 h. The reaction mixture was diluted with ethyl acetate and washed with brine, dried over sodium sulfate and concentrated in vacuo. Chromatography (SiO$_2$; 95:4.5:0.5 DCM/MeOH/28% aqueous NH$_3$) yielded the title compound, which was freeze-dried from acetonitrile/water to afford a white powder (123 mg, 65%). $\delta_H$ (DMSO-d$_6$) 9.20 (1H, br s), 8.35 (1H, dd, J 4.5, 1.5 Hz), 7.79 (1H, dd, J 8.1, 1.5 Hz), 7.68 (1H, dd, J 10.4, 1.9 Hz), 7.64 (1H, s), 7.50 (1H, ddd, J 8.5, 1.9, 0.9 Hz), 7.36 (1H, dd, J 8.1, 1.5 Hz), 7.15 (1H, dd, J 8.7, 8.7 Hz), 4.10-4.06 (1H, m), 3.63-3.56 (1H, m), 3.48 (2H, m), 3.36-3.33 (1H, m), 2.95-2.83 (1H, m), 2.41 (1H, dd, J 17.0, 8.5 Hz), 1.95 (1H, dd, J 17.0, 1.9 Hz). LCMS RT 1.82 minutes, (ES$^+$) 523.0 (M+H)$^+$.

Example 20 cis-(4,7)-6-({2-[(2-Fluoro-4-iodophenyl)amino]thieno[2,3-b]pyridin-3-yl}carbonyl)hexahydropyrrolo[3,4-d][1,3]oxazine-2(1H)-thione Intermediate 31 (91 mg, 0.18 mmol) in DMF (4 mL) was treated with 1,1'-thiocarbonyldiimidazole (35 mg, 0.20 mmol) and stirred at r.t. for 6 h. The reaction mixture was diluted with ethyl acetate, and the organic solution washed with brine, then dried over sodium sulfate and concentrated in vacuo. Purification using preparative HPLC yielded the title compound, which was suspended in acetonitrile/water and freeze-dried to afford a grey powder (33 mg, 33%). $\delta_H$ (DMSO-d$_6$) 9.60 (1H, br s), 8.97 (1H, br s), 8.35 (1H, dd, J 4.5, 1.3 Hz), 7.81-7.78 (1H, m), 7.69 (1H, dd, J 10.4, 1.7 Hz), 7.55-7.51 (1H, m), 7.35 (1H, dd, J 7.9, 4.5 Hz), 7.15 (1H, dd, J 8.7, 8.7 Hz), 4.31 (1H, dd, J 11.5, 3.2 Hz), 4.18-4.14 (1H, m), 3.94-3.89 (1H, m), 3.60-3.54 (3H, m), 3.40-3.35 (1H, m), 2.83-2.80 (1H, m). LCMS RT 1.98 minutes, (ES$^+$) 555.0 (M+H)$^+$.

Example 21

N-(2-Fluoro-4-iodophenyl)-3-[(2-methyl-4,6-dihydropyrrolo[3,4-d]imidazol-5(1H)-yl)carbonyl]thieno[2,3-b]pyridin-2-amine To a solution of Intermediate 63 (47 mg, 0.39 mmol) and DIPEA (0.40 mL, 2.29 mmol) in DMF (4 mL) was added Intermediate 5 (159 mg, 0.38 mmol) in DMF (4 mL). The reaction was stirred for 18 h at r.t. at which time the mixture was evaporated in vacuo. The residue was diluted with EtOAc (30 mL) and washed with brine (3×30 mL). The aqueous was back-extracted with EtOAc (100 mL) and 10% MeOH/DCM (3×100 mL), and the combined organics were dried (Na$_2$SO$_4$) and concentrated in vacuo. The crude product was purified by chromatography (SiO$_2$; 95:4.5:0.5 DCM/MeOH/28% aqueous NH$_3$), and subsequently preparative HPLC, to obtain the title compound, which was freeze-dried from acetonitrile/water to give a white solid (9.4 mg, 5%). $\delta_H$ (DMSO-d$_6$) 11.82-11.66 (1H, m), 8.42-8.37 (1H, m), 8.38-8.34 (1H, m), 7.83 (1H, dd, J 1.5, 8.3 Hz), 7.64 (1H, dd, J 1.9, 10.5 Hz), 7.49-7.44 (1H, m), 7.38-7.32 (1H, m), 7.16 (1H, dd, J 8.7, 8.7 Hz), 4.57-4.27 (4H, m), 2.26 (3H, s). LCMS RT 1.61 minutes, (ES$^+$) 520 (M+H)$^+$.

Example 22

N-(2-Fluoro-4-iodophenyl)-3-{[cis-(3,6)-2-phenyl-3a,4,6,6a-tetrahydropyrrolo[3,4-d]imidazol-5(1H)-yl]carbonyl}thieno[2,3-b]pyridin-2-amine To a solution of Intermediate 65 (52 mg, 0.28 mmol) and DIPEA (0.24 mL, 1.39 mmol) in DMF (4 mL) was added Intermediate 5 (87 mg, 0.21 mmol) in DMF (3 mL). The reaction was stirred for 18 h at r.t. at which time the mixture was evaporated in vacuo. The crude product was purified by chromatography (SiO$_2$; 95:4.5:0.5→92.5:6.75:0.75 DCM/MeOH/28% aqueous NH$_3$) to obtain the title compound, which was freeze-dried from acetonitrile/water to give a pale yellow solid (83 mg, 68%). δ$_H$ (CDCl$_3$) 9.07-8.92 (1H, m), 8.33 (1H, dd, J 1.7, 5.7 Hz), 7.74 (1H, dd, J 1.5, 8.1 Hz), 7.74-7.60 (2H, m), 7.47-7.27 (5H, m), 7.23-7.16 (2H, m), 4.86-4.53 (2H, m), 4.28-3.96 (2H, m), 3.63-3.42 (2H, m). LCMS RT 1.83 minutes, (ES$^+$) 584 (M+H)$^+$.

Example 23

N-(2-Fluoro-4-iodophenyl)-3-{[cis-(3,6)-2-isopropyl-3a,4,6,6a-tetrahydropyrrolo[3,4-d]imidazol-5(1H)-yl]carbonyl}thieno[2,3-b]pyridin-2-amine To a solution of Intermediate 67 (69 mg, 0.45 mmol) and DIPEA (0.24 mL, 1.35 mmol) in DMF (3 mL) was added Intermediate 5 (94 mg, 0.23 mmol) in DMF (3 mL). The reaction was stirred for 18 h at r.t. at which time the mixture was evaporated in vacuo. The crude product was purified by chromatography (SiO$_2$; 95:4.5:0.5→92.5:6.75:0.75 DCM/MeOH/28% aqueous NH$_3$) to obtain the title compound, which was freeze-dried from acetonitrile/water to give a pale yellow solid (85 mg, 69%). δ$_H$ (DMSO-d$_6$) 8.35 (1H, dd, J 1.7, 4.7 Hz), 7.77 (1H, dd, J 1.3, 8.1 Hz), 7.68 (1H, dd, J 1.9, 10.5 Hz), 7.53-7.47 (1H, m), 7.34 (1H, dd, J 4.7, 8.1 Hz), 7.18 (1H, dd, J 8.7, 8.7 Hz), 4.29 (2H, s), 3.73-3.56 (2H, m), 3.44-3.29 (2H, m), 2.38-2.26 (1H, m), 0.99 (3H, s), 0.97 (3H, s). LCMS RT 1.73 minutes, (ES$^+$) 550 (M+H)$^+$.

Example 24

3-{[cis-(3,6)-2-(tert-Butyl)-3a,4,6,6a-tetrahydropyrrolo[3,4-d]imidazol-5(1H)-yl]carbonyl}-N-(2-fluoro-4-iodophenyl)thieno[2,3-b]pyridin-2-amine To a solution of Intermediate 69 (69 mg, 0.39 mmol) and DIPEA (0.20 mL, 1.16 mmol) in DMF (2 mL) was added Intermediate 5 (80 mg, 0.19 mmol) in DMF (3 mL). The reaction was stirred for 18 h at r.t. at which time the mixture was evaporated in vacuo. The crude product was purified by chromatography (SiO$_2$; 95:4.5:0.5→92.5:6.75:0.75 DCM/MeOH/28% aqueous NH$_3$), then further purified by preparative HPLC, to obtain the title compound, which was freeze-dried from acetonitrile/water to give a pale yellow solid (16 mg, 15%). δ$_H$ (DMSO-d$_6$) 9.47-8.87 (1H, m), 8.34 (1H, dd, J 1.5, 4.7 Hz), 7.77 (1H, d, J 7.9 Hz), 7.68 (1H, dd, J 1.9, 10.5 Hz), 7.54-7.48 (1H, m), 7.34 (1H, dd, J 4.7, 8.1 Hz), 7.25-7.14 (1H, m), 4.39-4.21 (2H, m), 3.75-3.55 (2H, m), 3.49-3.29 (2H, m), 1.02 (9H, s). LCMS RT 1.82 minutes, (ES$^+$) 565 (M+H)$^+$.

Example 25

(4aS,7aR)-6-[2-(2-Fluoro-4-iodophenylamino)thieno[2,3-b]pyridine-3-carbonyl]-hexahydropyrrolo[3,4-b][1,4]oxazin-3-one A stirred solution of Intermediate 72 (0.12 g, 0.86 mmol) in DCM (10 mL) was treated with DIPEA (0.15 mL, 0.86 mmol) followed by the addition of Intermediate 5 (0.36 g, 0.86 mmol) and the resulting solution was stirred at room temperature for 18 h. Removal of the volatiles in vacuo followed by purification by column chromatography (SiO$_2$; 97.5:2.5 DCM/MeOH) gave a pale yellow solid. A second purification by column chromatography (SiO$_2$; 85.5:9.5:5 DCM/MeOH/NH$_3$) gave the title compound (0.12 g, 26%) as a pale yellow solid. δ$_H$ (DMSO-d$_6$) 9.27 (1H, s), 8.37 (1H, d, J 3.1 Hz), 8.13 (1H, br s), 7.81 (1H, d, J 7.9 Hz), 7.70 (1H, d, J 1.8 Hz), 7.49 (1H, d, J 8.3 Hz), 7.36 (1H, dd, J 4.7, 3.4 Hz), 7.14 (1H, br t), 4.24 (1H, br s), 4.01 (2H, d, J 2.2 Hz), 3.81-3.77 (2H, m), 3.57 (1H, br s), 3.40-3.22 (2H, m). LCMS (ES$^+$) 539 (M+H)$^+$, RT 1.18 minutes (pH 10).

Example 26

[2-(2-Fluoro-4-iodophenylamino)thieno[2,3-b]pyridin-3-yl]-[(4aS,7aR)-hexahydro-pyrrolo[3,4-b][1,4]oxazin-6-yl]-methanone A stirred solution of Intermediate 79 (0.40 g, 0.58 mmol) in DMF (15 mL) was treated with CsF (0.28 g, 1.86 mmol) and stirred at 95° C. The reaction was monitored by thin layer chromatography (1:1 MeOH/EtOAc). When the reaction was complete, MeOH (1 mL) was added and the mixture concentrated under vacuum. Purification by gradient column chromatography (SiO$_2$; EtOAc→1:1 MeOH/EtOAc) gave a white solid. Purification by preparative HPLC gave the title compound (90 mg). δ$_H$ (DMSO-d$_6$) 9.50-8.70 (1H, br), 8.35 (1H, dd, J 1.5, 3.2 Hz), 7.80 (1H, d, J 6.9 Hz), 7.66 (1H, dd, J 1.8, 8.7 Hz), 7.47 (1H, d, J 8.4 Hz), 7.37 (1H, dd, J 4.7, 3.4 Hz), 7.11 (1H, t, J 8.6 Hz), 3.86 (1H, s), 3.66 (1H, d, J 10.9 Hz), 3.49 (2H, m), 3.48-2.45 (6H, m). LCMS (ES$^+$) 525 (M+H)$^+$, RT 1.632 minutes (pH 3).

Example 27

5-[2-(2-Fluoro-4-iodophenylamino)thieno[2,3-b]pyridine-3-carbonyl]hexahydro-pyrrolo[3,4-c]pyrrole-2-carboxylic acid tert-butyl ester To a solution of Intermediate 5 (977 mg, 2.35 mmol) in DMF (10 mL) were added hexahydropyrrolo[3,4-c]pyrrole-2-carboxylic acid tert-butyl ester (500 mg, 2.35 mmol) and diisopropylamine (410 µL, 2.35 mmol). The mixture was stirred at r.t. for 18 h. The solvents were removed in vacuo and the residue dissolved in ethyl acetate (100 mL) and washed with brine three times. The organic phase was dried over sodium sulphate, filtered and the solvents removed in vacuo. The crude material was purified by column chromatography (SiO$_2$; ethyl acetate/dichloromethane gradient) to give the title compound as a yellow solid (850 mg, 60%). δ$_H$ (DMSO-d$_6$) 9.26 (1H, s), 8.35 (1H, dd, J 1.6, 4.6 Hz), 7.83 (1H, dd, J 1.6, 8.1 Hz), 7.62 (1H, dd, J 1.6, 10.5 Hz), 7.47 (1H, d, J 8.5 Hz), 7.35 (1H, dd, J 4.7, 8.1 Hz), 7.11 (1H, dd, J 8.7, 8.7 Hz), 3.57-3.53 (2H, m), 3.39-3.35 (2H, m), 3.21-3.17 (2H, m), 3.02-2.95 (2H, br m), 2.82-2.78 (2H, m), 1.39 (9H, s). LCMS (ES$^+$) RT 2.69 minutes (pH 3 method), 609 (M+H)$^+$; purity 99% by UV.

Example 28

[2-(2-Fluoro-4-iodophenylamino)thieno[2,3-b]pyridin-3-yl]-(hexahydropyrrolo[3,4-c]pyrrol-2-yl)-methanone dihydrochloride Example 27 (750 mg, 1.23 mmol) was dissolved in MeOH (10 mL) and DCM (10 mL). Anhydrous HCl in 1,4-dioxane (4.0M, 25 mL) was added and the mixture was stirred at r.t. for 18 h. The solvent was removed in vacuo and the resultant sticky yellow solid was re-dissolved in water (5 mL) and lyophilized to afford the title compound as a yellow solid (700 mg, 97%). $\delta_H$ (DMSO-$d_6$) 9.42 (2H, br s), 9.28 (1H, s), 8.35 (1H, dd, J 1.6, 4.7 Hz), 7.86 (1H, dd, J 1.5, 8.1 Hz), 7.70 (1H, dd, J 1.9, 10.4 Hz), 7.52 (1H, dd, J 1.0, 8.4 Hz), 7.38 (1H, dd, J 4.7, 8.1 Hz), 7.21 (1H, dd, J 8.6, 8.6 Hz), 5.30 ($H_3O^+$ exchange), 3.71-3.57 (2H, m), 3.51-3.46 (2H, m), 3.42-3.32 (2H, m), 3.00-2.95 (4H, m). LCMS (ES$^+$) RT 1.56 minutes (pH 3 method), 509 (M+H)$^+$; purity 99.7% by UV.

Example 29

3-[(2,2-Dimethyltetrahydro-5H-[1,3]dioxolo[4,5-c]pyrrol-5-yl)carbonyl]-N-(2-fluoro-4-iodophenyl)thieno[2,3-b]pyridin-2-amine Intermediate 18 (96 mg, 0.18 mmol) was suspended in anhydrous toluene (2 mL), and 2,2-dimethoxypropane (47 mL, 0.40 mmol) and p-toluenesulfonic acid monohydrate (152 mg, 0.8 mmol) were added sequentially. The reaction mixture was stirred under ambient conditions for 4 h, then $Na_2SO_4$ (0.5 g) was added and the reaction mixture was stirred for a further 72 h. The reaction was filtered and the solvent removed to yield a clear oil. Trituration with diethyl ether afforded the title compound as a white solid (90 mg, 92%). $\delta_H$ (DMSO-$d_6$) 9.12 (1H, s), 8.37 (1H, dd, J 4.7, 1.5 Hz), 7.86 (1H, dd, J 7.9, 1.5 Hz), 7.69 (1H, dd, J 10.5, 1.9 Hz), 7.50 (1H, m), 7.38 (1H, dd, J 8.1, 4.5 Hz), 7.20 (1H, t, J 8.7 Hz), 4.70 (2H, d, J 1.7 Hz), 3.83-3.72 (2H, m), 3.30-3.18 (2H, m), 1.27 (3H, s), 1.19 (3H, s). LCMS RT 2.55 minutes, (ES$^-$) 538 (M−H)$^-$, (ES$^+$) 540 (M+H)$^+$.

Example 30

1-{(3aS,6aR)-5-[2-(2-Fluoro-4-iodophenylamino)thieno[2,3-b]pyridine-3-carbonyl]-2,2-(dimethyl)tetrahydropyrrolo[3,4-d]oxazol-3-yl}ethanone Intermediate 81 (263 mg, 0.53 mmol) was dissolved in DCM (10 mL), and DIPEA (92 µl, 0.58 mmol) and acetyl chloride (38 µl, 0.58 mmol) were added sequentially. After 1 h the reaction was quenched by addition of saturated aqueous sodium bicarbonate solution and then extracted into DCM (50 mL). The organic layer was separated, dried with $Na_2SO_4$, filtered and the solvent removed in vacuo to yield a pale yellow solid. The solid was suspended in toluene (10 mL) and heated to 110° C. p-Toluenesulfonic acid monohydrate (catalytic) and 2,2-dimethoxypropane (124.2 µl, 1.1 mmol) were then added and the reaction stirred for 2 h. The toluene was then removed under reduced pressure and the remaining solid partitioned between EtOAc (50 mL) and $NaHCO_3$ (aqueous). The organic layer was separated, dried with $Na_2SO_4$, filtered and the solvent removed under vacuum to yield the crude aminal. Purification using silica gel chromatography yielded the title compound (135 mg, 45%). $\delta_H$ (DMSO-$d_6$) 9.23 (1H, s), 8.37 (1H, dd, J 4.7, 1.5 Hz), 7.84 (1H, dd, J 7.9, 1.3 Hz), 7.68 (1H, dd, J 10.5, 1.9 Hz), 7.52-7.45 (1H, m), 7.37 (1H, dd, J 7.9, 4.5 Hz), 7.18 (1H, t, J 8.7 Hz), 4.70-4.65 (1H, m), 4.59-4.52 (1H, m) 3.85-3.43 (4H, m), 1.93 (3H, s), 1.45 (3H, s), 1.39 (3H, s). LCMS RT 2.24 minutes, (ES) 579 (M−H)$^-$, (ES$^+$) 581 (M+H)$^+$.

Example 31

5-[2-(2-Fluoro-4-iodophenylamino)thieno[2,3-b]pyridine-3-carbonyl]tetrahydro-pyrrolo[3,4-c]pyrrole-1,3-dione To a solution of Intermediate 82 (100 mg, 0.71 mmol) in DMF (20 mL) were added Intermediate 5 (300 mg, 0.72 mmol) and DIPEA (102 mg, 0.79 mmol) and the mixture was stirred at r.t. for 2 h. After this time water (5 mL) was added until a beige-coloured precipitate formed. The precipitate was filtered off, and washed with water and diethyl ether, to give the title compound as a beige solid (135 mg, 35%). $\delta_H$ (DMSO-$d_6$) 11.25 (1H, s), 9.26 (1H, m), 8.34 (1H, dd, J 1.4, 4.5 Hz), 7.68 (2H, m), 7.49 (1H, d, J 8.6 Hz), 7.34 (1H, dd, J 4.7, 8.1 Hz), 7.17 (1H, dd, J 8.6, 8.6 Hz), 3.89 (2H, m), 3.55 (2H, m), 3.40 (2H, m). LCMS RT 1.97 minutes, (ES$^+$) 537 (M+H)$^+$.

Example 32

[(3aS,6aR)-2-(Ethylamino)-3a,4,6,6a-tetrahydropyrrolo[3,4-d]oxazol-5-yl]-[2-(2-fluoro-4-iodophenylamino)thieno[2,3-b]pyridin-3-yl]-methanone To a solution of Intermediate 85 (420 mg, 0.74 mmol) in DCM (50 mL), cooled to −78° C., was added DAST (0.1 mL, 0.74 mmol) and the mixture was stirred for 60 minutes before being allowed to warm up to r.t. After 18 h the reaction mixture was diluted with DCM (50 mL) and washed with saturated sodium bicarbonate solution (50 mL). After drying ($Na_2SO_4$) and filtration the organics were evaporated in vacuo to give a yellow oil which was then subjected to purification by chromatography ($SiO_2$; 5% EtOH in DCM) to afford the title compound as a yellow oil (120 mg, 29%). $\delta_H$ (DMSO-$d_6$) 9.21 (1H, s), 8.35 (1H, dd, J 1.5, 4.6 Hz), 7.70 (2H, m), 7.50 (1H, d, J 8.4 Hz), 7.35 (1H, dd, J 4.7, 8.1 Hz), 7.19 (1H, dd, J 8.7, 8.7 Hz), 6.31 (1H, s), 4.96 (1H, dd, J 4.9, 7.2 Hz), 4.41 (1H, dd, J 6.3, 6.3 Hz), 3.95 (2H, m), 3.55 (2H, m), 2.94 (2H, q, J 6.9 Hz), 0.96 (3H, t, J 6.9 Hz). LCMS RT 2.14 minutes, (ES$^+$) 552 (M+H)$^+$.

Example 33

[2-(2-Fluoro-4-iodophenylamino)thieno[2,3-b]pyridin-3-yl]-[3aS,6aR)-2-(methylamino)-3a,4,6,6a-tetrahydropyrrolo[3,4-d]thiazol-5-yl]-methanone To a solution of Intermediate 88 (400 mg, 0.72 mmol) in DCM (50 mL), cooled in an acetone/cardice bath, was added DAST (0.1 mL, 0.74 mmol) and the mixture was stirred for 60 minutes before being allowed to warm up to r.t. After 18 h the reaction mixture was diluted with DCM (50 mL) and washed with sodium bicarbonate solution (50 mL). After drying ($Na_2SO_4$) the organics were evaporated in vacuo to give a crude yellow oil. Separation by chromatography ($SiO_2$; 5% EtOH in DCM) afforded the title compound as a yellow oil (63 mg, 16%). $\delta_H$ (DMSO-$d_6$) 9.17 (1H, s), 8.35 (1H, dd, J 1.5, 4.6 Hz), 7.80 (1H, dd, J 1.3, 8.0 Hz), 7.66 (1H, dd, J 1.8, 10.5 Hz), 7.48 (1H, d, J 8.5 Hz), 7.35 (1H, dd J 4.7, 8.1 Hz), 7.17 (1H, dd, J 8.6, 8.6 Hz), 6.66 (1H, s), 4.71 (1H, dd, J 7.2, 7.2 Hz), 4.22 (1H, m), 3.70 (2H, m), 3.55 (2H, m), 2.66 (3H, s). LCMS RT 2.14 minutes, (ES$^+$) 554 (M+H)$^+$.

Example 34

[2-(2-Fluoro-4-iodophenylamino)thieno[2,3-b]pyridin-3-yl]-[3aS,6aR)-1-methyl-2-(thioxo)hexahydropyrrolo[3,4-d]imidazol-5-yl]-methanone Obtained as a by-product from the reaction described in Example 33. Separation of the compounds by column chromatography (SiO$_2$; 5% EtOH in DCM) gave the title compound as a yellow oil (44 mg, 12%). δ$_H$ (DMSO-d$_6$) 9.14 (1H, s), 8.35 (1H, dd, J 1.5, 4.6 Hz), 7.72 (1H, s), 7.67 (1H, dd, J 1.9, 10.5 Hz), 7.52 (1H, d, J 9.3 Hz), 7.33 (1H, dd, 4.6, 8.1 Hz), 7.17 (1H, dd, J 8.7, 8.7 Hz), 4.44 (1H, m), 4.33 (1H, m), 3.93 (1H, m), 3.65 (1H, m), 3.32 (2H, m), 2.86 (3H, s). LCMS RT 2.14 minutes, (ES$^+$) 554 (M+H)$^+$.

Example 35

[2-(2-Fluoro-4-iodophenylamino)thieno[2,3-b]pyridin-3-yl]-[(3aS,6aR)-2-imino-3-(methyl)hexahydropyrrolo[3,4-d]thiazol-5-yl]-methanone Intermediate 94 (80 mg, 0.10 mmol) was treated with a solution of 40% morpholine in DCM (10 mL) and stirred overnight at r.t. After this time the reaction mixture was diluted with ethyl acetate (25 mL) and then washed with brine (2×50 mL), dried (Na$_2$SO$_4$), filtered and evaporated in vacuo to afford the title compound as a white powder (39 mg, 70%). δ$_H$(DMSO-d$_6$) 9.24 (1H, s), 8.41 (1H, dd, J 1.4, 4.6 Hz), 7.85 (1H, m), 7.72 (1H, m), 7.52 (1H, d, J 9.3 Hz), 7.41 (1H, dd, J 4.7, 8.1 Hz), 7.21 (1H, dd, J 8.6, 8.6 Hz), 4.28 (1H, m), 4.18 (1H, m), 3.80 (1H, m), 3.66-3.32 (3H, m), 2.73 (3H, s). LCMS RT 2.00 minutes, (ES$^+$) 554 (M+H)$^+$.

Example 36

(3aS,6aR)-5-[2-(2-Fluoro-4-iodophenylamino)thieno [2,3-b]pyridine-3-carbonyl]-3-(morpholin-4-ylmethyl)hexahydropyrrolo[3,4-d]oxazol-2-one Example 2 (280 mg, 0.53 mmol) in ethanol (3 mL) was treated with morpholine (695 mg, 8.0 mmol, 15 eq) and formaldehyde (157 µL, 1.57 mmol, 3 eq), then heated at 100° C. for 3 h. The reaction mixture was concentrated in vacuo and the residue was chromatographed (NH$_2$-silica with a DCM/ethyl acetate gradient elution; 0-100% ethyl acetate) to yield the title compound (15 mg). δ$_H$ (DMSO-d$_6$) 9.37 (1H, s), 8.38 (1H, dd, J 4.7, 1.7 Hz), 7.68 (1H, dd, J 8.1, 1.5 Hz), 7.52 (2H, m), 7.40 (1H, m), 7.33 (1H, dd, J 8.1, 4.7 Hz), 5.08 (1H, m), 4.50 (1H, dd, J 7.3, 5.3 Hz), 4.12 (2H, m), 3.91 (1H, s), 3.69 (5H, m), 3.54 (1H, dd, J 13.8, 5.1 Hz), 3.37 (1H, dd, J 13.4, 5.5 Hz), 2.52 (4H, m). LCMS (ES$^+$) 624 (M+H)$^+$, RT 1.99 minutes (pH 3), 2.00 minutes (pH 10).

Example 37

(3aS,6aR)-5-[2-(2-Fluoro-4-iodophenylamino)thieno [2,3-b]pyridine-3-carbonyl]-3-(methyl)hexahydropyrrolo[3,4-d]oxazol-2-one Intermediate 97 (290 mg, 1.62 mmol) in DMF (5 mL) was treated with Intermediate 5 (734 mg, 1.79 mmol) and DIPEA (460 mg, 3.57 mmol) and stirred at r.t. overnight. The reaction mixture was concentrated in vacuo, azeotroped with heptane, dissolved in DCM, washed with saturated sodium hydrogencarbonate solution, dried (sodium sulphate), filtered and concentrated in vacuo. The crude residue was purified by column chromatography (SiO$_2$; ethyl acetate) to yield the title compound (225 mg). δ$_H$ (DMSO-d$_6$) 9.25 (1H, s), 8.36 (1H, dd, J 4.7, 1.5 Hz), 7.70 (2H, m), 7.51 (1H, ddd, J 8.5, 1.9, 0.9 Hz), 7.36 (1H, dd, J 8.1, 4.7 Hz), 7.21 (1H, t, J 8.7 Hz), 5.03 (1H, m), 4.28 (1H, dd, J 7.5, 4.7 Hz), 3.93 (1H, m), 3.83 (1H, m), 3.83-3.49 (1H, m), 3.25 (1H, m), 2.66 (3H, s). LCMS (ES$^+$) 539 (M+H)$^+$, RT 2.04 minutes (pH 3), 2.05 minutes (pH 10).

The invention claimed is:

1. A compound of formula (I), or a pharmaceutically acceptable salt or N-oxide thereof:

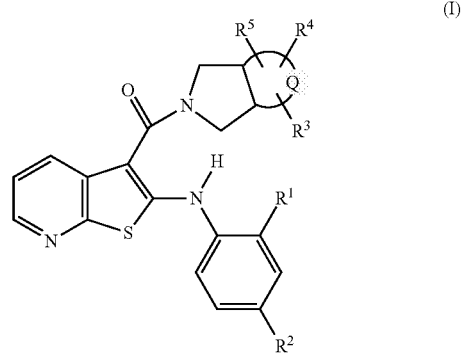

(I)

wherein

Q is a three-, four-, five- or six-membered heterocyclic ring optionally containing one or two double bonds, wherein the heterocyclic ring comprises one, two or three heteroatoms independently selected from oxygen, sulphur, nitrogen and phosphorus;

R$^1$ is hydrogen, halogen, cyano, nitro, C$_{1-6}$ alkyl, trifluoromethyl, C$_{1-6}$ alkoxy, trifluoromethoxy, C$_{1-6}$ alkylthio, C$_{1-6}$ alkylsulphinyl or C$_{1-6}$ alkylsulphonyl;

R$^2$ is halogen, nitro, cyano, C$_{1-6}$ alkyl, C$_{2-6}$ alkynyl, hydroxy(C$_{1-6}$)alkyl or formyl;

R$^3$ and R$^4$ are each independently hydrogen, C$_{1-6}$ alkyl, C$_{1-6}$ alkoxy, C$_{1-6}$ alkylamino(C$_{1-6}$)alkoxy, C$_{1-6}$ alkoxy (C$_{1-6}$)alkyl, C$_{1-6}$ alkylthio, C$_{1-6}$ alkylsulphonyl, hydroxy, hydroxy(C$_{1-6}$)alkyl, amino(C$_{1-6}$)alkyl, nitro (C$_{1-6}$)alkyl, halogen, cyano, trifluoromethyl, aryl, aryl (C$_{1-6}$)alkyl, C$_{3-7}$ heterocycloalkyl(C$_{1-6}$)alkyl, heteroaryl, heteroaryl(C$_{1-6}$)alkyl, oxo, thioxo, imino, C$_{2-6}$ alkylcarbonyl, carboxy, C$_{2-6}$ alkoxycarbonyl, amino, C$_{1-6}$ alkylamino, di(C$_{1-6}$)alkylamino, bis[hydroxy(C$_{1-6}$) alkyl]-amino, C$_{1-6}$ alkylamino(C$_{1-6}$)alkylamino, C$_{3-7}$ cycloalkylamino, arylamino, heteroarylamino, C$_{2-6}$ alkylcarbonylamino, C$_{2-6}$ alkoxycarbonylamino, (C$_{2-6}$) alkoxycarbonyl(C$_{1-6}$)alkylamino, [(C$_{2-6}$)alkoxycarbonyl][(C$_{1-6}$)alkyl]amino, bis[(C$_{2-6}$)alkoxycarbonyl(C$_{1-6}$) alkyl]amino, C$_{2-6}$ alkoxycarbonylamino(C$_{1-6}$)alkyl or aminocarbonyl; or R$^3$ and R$^4$, when taken together with the carbon atom to which they are both attached, form a C$_{3-7}$ cycloalkyl or a C$_{3-7}$ heterocycloalkyl, said C$_{3-7}$ cycloalkyl or said C$_{3-7}$ heterocycloalkyl optionally substituted by one or more substituents independently selected from C$_{1-6}$ alkyl, hydroxy and amino; and R$^5$ is hydrogen or C$_{1-6}$ alkyl.

2. A compound or pharmaceutically acceptable salt or N-oxide thereof according to claim 1 having the following formula (IIA):

(IIA)

wherein
R¹¹ is halogen; and
R¹² is halogen, nitro, cyano, $C_{2-6}$ alkynyl, hydroxy($C_{1-6}$) alkyl or formyl.

3. A compound according to claim 2, wherein R¹¹ is fluoro or chloro.

4. A compound according to claim 2, wherein R¹² is iodo.

5. A compound according to claim 3, wherein R¹² is iodo.

6. A compound according to claim 1, wherein Q is a four-, five- or six-membered heterocyclic ring.

7. A compound according to claim 2, wherein Q is a four-, five- or six-membered heterocyclic ring.

8. A compound according to claim 6 wherein Q is selected from azetidinyl, pyrrolidinyl, dioxolanyl, oxazolidinyl, thiazolidinyl, imidazolidinyl, dioxaphospholanyl, oxazolinyl, thiazolinyl, imidazolinyl, imidazolyl, piperidinyl and tetrahydrooxazinyl.

9. A compound according to claim 7 wherein Q is selected from azetidinyl, pyrrolidinyl, dioxolanyl, oxazolidinyl, thiazolidinyl, imidazolidinyl, dioxaphospholanyl, oxazolinyl, thiazolinyl, imidazolinyl, imidazolyl, piperidinyl and tetrahydrooxazinyl.

10. A compound according to claim 1, wherein R³ and R⁴ are each independently hydrogen, $C_{1-6}$ alkyl, hydroxy, aryl, $C_{3-7}$ heterocycloalkyl($C_{1-6}$)alkyl, oxo, thioxo, imino, $C_{2-6}$ alkylcarbonyl, $C_{2-6}$ alkoxycarbonyl, amino, $C_{1-6}$ alkylamino or $C_{3-7}$ cycloalkylamino.

11. A compound according to claim 2, wherein R³ and R⁴ are each independently hydrogen, $C_{1-6}$ alkyl, hydroxy, aryl, $C_{3-7}$ heterocycloalkyl($C_{1-6}$)alkyl, oxo, thioxo, imino, $C_{2-6}$ alkylcarbonyl, $C_{2-6}$ alkoxycarbonyl, amino, $C_{1-6}$ alkylamino or $C_{3-7}$ cycloalkylamino.

12. A compound according to claim 10 wherein R³ is hydrogen, methyl, isopropyl, tert-butyl, hydroxy, phenyl, morpholinylmethyl, oxo, thioxo, imino, acetyl, tert-butoxycarbonyl, amino, methylamino, ethylamino or cyclopropylamino.

13. A compound according to claim 11 wherein R³ is hydrogen, methyl, isopropyl, tert-butyl, hydroxy, phenyl, morpholinylmethyl, oxo, thioxo, imino, acetyl, tert-butoxycarbonyl, amino, methylamino, ethylamino or cyclopropylamino.

14. A compound according to claim 10, wherein R⁴ is hydrogen, methyl, hydroxy or oxo.

15. A compound according to claim 11, wherein R⁴ is hydrogen, methyl, hydroxy or oxo.

16. A compound according to claim 12, wherein R⁴ is hydrogen, methyl, hydroxy or oxo.

17. A compound according to claim 13, wherein R⁴ is hydrogen, methyl, hydroxy or oxo.

18. A compound according to claim 1, wherein R⁵ is hydrogen.

19. A compound according to claim 2, wherein R⁵ is hydrogen.

20. A compound or pharmaceutically acceptable salt or N-oxide thereof according to claim 1, which is selected from the group consisting of:
5-[2-(2-Fluoro-4-iodophenylamino)thieno[2,3-b]pyridine-3-carbonyl]-3-methyl-hexahydropyrrolo[3,4-d]oxazol-2-one;
(3aS,6aR)-5-[2-(2-Fluoro-4-iodophenylamino)thieno[2,3-b]pyridine-3-carbonyl]-hexahydropyrrolo[3,4-d]oxazol-2-one;
(3aR,6aS)-5-[2-(2-Fluoro-4-iodophenylamino)thieno[2,3-b]pyridine-3-carbonyl]-tetrahydro[1,3]dioxolo[4,5-c]pyrrol-2-one;
(3aR,6aS)-5-[2-(2-Fluoro-4-iodophenylamino)thieno[2,3-b]pyridine-3-carbonyl]-hexahydropyrrolo[3,4-d]oxazol-2-one;
[2-(2-Fluoro-4-iodophenylamino)thieno[2,3-b]pyridin-3-yl]-[(3aS,6aR)-2-phenyl-3a,4,6,6a-tetrahydropyrrolo[3,4-d]oxazol-5-yl]-methanone;
cis-(4,7)-6-({2-[(2-Fluoro-4-iodophenyl)amino]thieno[2,3-b]pyridin-3-yl}carbonyl)hexahydropyrrolo[3,4-d][1,3]oxazin-2(1H)-one;
3-[cis-(1,5)-3,6-Diazabicyclo[3.2.0]hept-3-ylcarbonyl]-N-(2-fluoro-4-iodophenyl)thieno[2,3-b]pyridin-2-amine;
trans-(4,7)-6-({2-[(2-Fluoro-4-iodophenyl)amino]thieno[2,3-b]pyridin-3-yl}carbonyl)hexahydropyrrolo[3,4-d][1,3]oxazin-2(1H)-one;
N-(2-Fluoro-4-iodophenyl)-3-[cis-(3,6)-hexahydropyrrolo[3,4-b]pyrrol-5(1H)-ylcarbonyl]thieno[2,3-b]pyridin-2-amine;
meso-N-(2-Fluoro-4-iodophenyl)-3-[(3aR*,6aS*)-tetrahydro-5H-spiro[1,3-dioxolo[4,5-c]pyrrole-2,4'-piperidin]-5-ylcarbonyl]thieno[2,3-b]pyridin-2-amine;
meso-(3aR*,6aS*)-5-({2-[(2-Fluoro-4-iodophenyl)amino]thieno[2,3-b]pyridin-3-yl}carbonyl)tetrahydro-3aH-[1,3,2]dioxaphospholo[4,5-c]pyrrol-2-ol 2-oxide;
N-(2-Fluoro-4-iodophenyl)-3-{[cis-(3,6)-2-methyl-3a,4,6,6a-tetrahydropyrrolo[3,4-d]imidazol-5(1H)-yl]carbonyl}thieno[2,3-b]pyridin-2-amine;
cis-(3,6)-5-[2-(2-Fluoro-4-iodophenylamino)thieno[2,3-b]pyridine-3-carbonyl]-hexahydropyrrolo[3,4-d]imidazol-2-one;
[(3aS,6aR)-2-Amino-3a,4,6,6a-tetrahydropyrrolo[3,4-d]thiazol-5-yl]-[2-(2-fluoro-4-iodo-phenylamino)thieno[2,3-b]pyridin-3-yl]-methanone;
[(3aS,6aR)-2-(Cyclopropylamino)-3a,4,6,6a-tetrahydropyrrolo[3,4-d]thiazol-5-yl]-[2-(2-fluoro-4-iodophenylamino)thieno[2,3-b]pyridin-3-yl]-methanone;
[(3aS,6aR)-2-Amino-3a,4,6,6a-tetrahydropyrrolo[3,4-d]oxazol-5-yl]-[2-(2-fluoro-4-iodo-phenylamino)thieno[2,3-b]pyridin-3-yl]-methanone;
[2-(2-Fluoro-4-iodophenylamino)thieno[2,3-b]pyridin-3-yl]-[(3aS,6aR)-2-thioxo-hexahydropyrrolo[3,4-d]oxazol-5-yl]-methanone;
N-(2-Fluoro-4-iodophenyl)-3-[cis-(4,7)-octahydro-6H-pyrrolo[3,4-b]pyridin-6-ylcarbonyl]thieno[2,3-b]pyridin-2-amine;
cis-(3,6)-5-({2-[(2-Fluoro-4-iodophenyl)amino]thieno[2,3-b]pyridin-3-yl}carbonyl)-hexahydropyrrolo[3,4-b]pyrrol-2(1H)-one;
cis-(4,7)-6-({2-[(2-Fluoro-4-iodophenyl)amino]thieno[2,3-b]pyridin-3-yl}carbonyl)hexahydropyrrolo[3,4-d][1,3]oxazine-2(1H)-thione;

N-(2-Fluoro-4-iodophenyl)-3-[(2-methyl-4,6-dihydropyrrolo[3,4-d]imidazol-5(1H)-yl)carbonyl]thieno[2,3-b]pyridin-2-amine;

N-(2-Fluoro-4-iodophenyl)-3-{[cis-(3,6)-2-phenyl-3a,4,6,6a-tetrahydropyrrolo[3,4-d]imidazol-5(1H)-yl]carbonyl}thieno[2,3-b]pyridin-2-amine;

N-(2-Fluoro-4-iodophenyl)-3-{[cis-(3,6)-2-isopropyl-3a,4,6,6a-tetrahydropyrrolo[3,4-d]imidazol-5(1H)-yl]carbonyl}thieno[2,3-b]pyridin-2-amine;

3-{[cis-(3,6)-2-(tert-Butyl)-3a,4,6,6a-tetrahydropyrrolo[3,4-d]imidazol-5(1H)-yl]carbonyl}-N-(2-fluoro-4-iodophenyl)thieno[2,3-b]pyridin-2-amine;

(4aS,7aR)-6-[2-(2-Fluoro-4-iodophenylamino)thieno[2,3-b]pyridine-3-carbonyl]-hexahydropyrrolo[3,4-b][1,4]oxazin-3-one;

[2-(2-Fluoro-4-iodophenylamino)thieno[2,3-b]pyridin-3-yl]-[(4aS,7aR)-hexahydro-pyrrolo[3,4-b][1,4]oxazin-6-yl]-methanone;

5-[2-(2-Fluoro-4-iodophenylamino)thieno[2,3-b]pyridine-3-carbonyl]hexahydro-pyrrolo[3,4-c]pyrrole-2-carboxylic acid tert-butyl ester; and

[2-(2-Fluoro-4-iodophenylamino)thieno[2,3-b]pyridin-3-yl]-(hexahydropyrrolo[3,4-c]pyrrol-2-yl)-methanone dihydrochloride.

21. A pharmaceutical composition comprising a compound of formula (I), or a pharmaceutically acceptable salt or N oxide thereof according to claim 1, and a pharmaceutically acceptable carrier.

\* \* \* \* \*